(12) United States Patent
Stern et al.

(10) Patent No.: US 12,203,124 B2
(45) Date of Patent: Jan. 21, 2025

(54) METHODS FOR IMPROVED RAPID ANTIMICROBIAL SUSCEPTIBILITY TESTING

(71) Applicant: SELUX DIAGNOSTICS, INC., Charlestown, MA (US)

(72) Inventors: Eric Stern, Charlestown, MA (US); Aleksandar Vacic, Charlestown, MA (US); Kelly Flentie, Charlestown, MA (US); Benjamin Spears, Charlestown, MA (US); Felicia Chen, Charlestown, MA (US)

(73) Assignee: SELUX DIAGNOSTICS, INC., Charlestown, MA (US)

( * ) Notice: Subject to any disclaimer, the term of this patent is extended or adjusted under 35 U.S.C. 154(b) by 1044 days.

(21) Appl. No.: 16/472,714

(22) PCT Filed: Dec. 22, 2017

(86) PCT No.: PCT/US2017/068306
§ 371 (c)(1),
(2) Date: Jun. 21, 2019

(87) PCT Pub. No.: WO2018/119439
PCT Pub. Date: Jun. 28, 2018

(65) Prior Publication Data
US 2020/0149086 A1 May 14, 2020

Related U.S. Application Data

(60) Provisional application No. 62/535,106, filed on Jul. 20, 2017, provisional application No. 62/488,454, filed on Apr. 21, 2017, provisional application No. 62/438,780, filed on Dec. 23, 2016.

(51) Int. Cl.
| | |
|---|---|
| C12Q 1/18 | (2006.01) |
| C07D 257/04 | (2006.01) |
| C07D 403/10 | (2006.01) |
| C07D 417/04 | (2006.01) |
| C07F 5/00 | (2006.01) |
| G01N 21/64 | (2006.01) |

(52) U.S. Cl.
CPC ............. *C12Q 1/18* (2013.01); *C07D 257/04* (2013.01); *C07D 403/10* (2013.01); *C07D 417/04* (2013.01); *C07F 5/003* (2013.01); *G01N 21/6408* (2013.01)

(58) Field of Classification Search
CPC ....... C12Q 1/18; C07F 5/003; G01N 21/6408; C07D 257/04; C07D 403/10; C07D 417/04
USPC ......................................................... 435/33
See application file for complete search history.

(56) References Cited

U.S. PATENT DOCUMENTS

| | | |
|---|---|---|
| 5,501,959 A | 3/1996 | Lancaster et al. |
| 7,897,331 B2 | 3/2011 | Albarella et al. |
| 2004/0063168 A1 | 4/2004 | Wiles et al. |
| 2005/0095665 A1 | 5/2005 | Williams et al. |
| 2016/0123958 A1* | 5/2016 | Quake ................. F16K 99/0051 506/10 |

FOREIGN PATENT DOCUMENTS

| | | |
|---|---|---|
| EP | 1160564 A2 | 12/2001 |
| JP | 2002125697 A | 5/2002 |
| WO | 2017127684 A1 | 7/2017 |
| WO | 2017185012 A1 | 10/2017 |

OTHER PUBLICATIONS

Marriott et al., Time-Resolved Delayed Luminescence Image Microscopy Using an Europium Ion Chelate Complex, Biophysical Journal, vol. 67, (1994), pp. 957-965.*
Johnson, I., and Spence, M., (eds.), The Molecular Probes Handbook: A Guide to Fluorescent Probes and Labeling Technologies, 11th Ed. Life Technologies, 2010. Abstract.
Riss TL, et al. "Cell Viability Assays. Assay Guidance Manual" Bethesda (MD) Assay Guidance Manual [online] [retrieved on Jun. 15, 2021] Retrieved from Internet URL: https://www.ncbi.nlm.nih.gov/books/NBK144065/?report=reader (2013) 15 pages.
International Search Report and Written Opinion for International application No. PCT/US2017/068306, mailed on Apr. 26, 2018, 24 pages.
Waites, K. B., et al., "Standardized Methods and Quality Control Limits for Agar and Broth Microdilution Susceptibility Testing of Mycoplasma pneumoniae, Mycoplasma hominis, and Ureaplasma urealyticum", Journal of Clinical Microbiology, 50(11):3542-3547 (2012).
Waites, K. B., et al., "Broth Microdilution Procedure—Online Supplementary material of Waites et al. 2012", Journal of Clinical Microbiology [online], Aug. 2012 [retrieved on Apr. 9, 2020]. Retrieved from Internet URL: https://jcm.asm.org/content/suppl/2012/10/10/JCM.01439-12.DCSupplemental/zjm999092020so3.pdf, 4 pages.
Leipold, M.D., et al., "Development of mass cytometry methods for bacterial discrimination", Analytical Biochemistry, 419(1):1-8 (2011).
Rahman, M., et al., "Evaluation of a Scanner-Assisted Colorimetric MIC Method for Susceptibility Testing of Gram-Negative Fermentative Bacteria", Applied and Environmental Microbiology, 70(4):2398-2403 (2004).
Ambriz-Avina, V., et al., "Applications of Flow Cytometry to Characterize Bacterial Physiological Respones", vol. 2014:1-14 (2014).

* cited by examiner

*Primary Examiner* — Jennifer M. H. Tichy
(74) *Attorney, Agent, or Firm* — Goodwin Procter LLP

(57) ABSTRACT

The present invention provides for improved antimicrobial susceptibility testing and more specifically for improved rapid antimicrobial susceptibility testing of clinical samples for efficient and versatile analysis and reliable results.

14 Claims, 32 Drawing Sheets

K PNEUMONIAE PERCENT CORRECT, ESSENTIAL AGREEMENT

| ANTIBIOTIC | METABOLIC ASSAY | SURFACE BINDING ASSAY |
|---|---|---|
| PEN | 86 | 94 |
| CRO | 100 | 98 |
| SXT | 98 | 94 |
| GEN | 83 | 95 |

Figure 29A

S AUREUS PERCENT CORRECT, ESSENTIAL AGREEMENT

| ANTIBIOTIC | METABOLIC ASSAY | SURFACE BINDING ASSAY |
|---|---|---|
| CIP | 94 | 87 |
| PEN | 86 | 94 |
| LZD | 96 | 100 |
| RIF | 94 | 98 |
| TET | 92 | 90 |

Figure 29B

METHODS FOR IMPROVED RAPID ANTIMICROBIAL SUSCEPTIBILITY TESTING

REFERENCE TO RELATED APPLICATIONS

This application is a national phase filing claiming the benefit of and priority to International Patent Application No. PCT/US2017/068306, filed on Dec. 22, 2017, which claims priority to U.S. Provisional Application Ser. No. 62/438,780, filed Dec. 23, 2016 and U.S. Provisional Application Ser. No. 62/488,454, filed Apr. 21, 2017, and U.S. Provisional Application Ser. No. 62/535,106, filed Jul. 20, 2017, the disclosures of which are hereby incorporated by reference.

FIELD

The present invention relates generally to antimicrobial susceptibility testing and more specifically to rapid antimicrobial susceptibility testing of clinical samples.

BACKGROUND

Antimicrobial-resistant microbial infections are associated with poor clinical outcomes including increased morbidity, mortality, and healthcare costs among infected patients. The prevalence of these organisms in such facilities in the United States has steadily increased over the last 30 years. Phenotypic antimicrobial susceptibility testing (AST) of microorganisms is critical for informing physicians of appropriate therapeutic regimens. Using current methods, AST determination typically requires a minimum of eight hours, rendering it an overnight process due to shift work in many clinical microbiology laboratories. While awaiting a determination from current AST methods, patients are often administered broad-spectrum antimicrobials which often have significant detrimental effects on patient health and/or contribute to the growing antimicrobial resistance epidemic. Furthermore, this time delay obtaining accurate antimicrobial treatment information increases patient stays in hospitals, thereby increasing costs and inconvenience to the patient.

Long times to obtain an AST determination result in incomplete information being delivered to physicians. The length of time involved results in end-point determination which often prevents the identification of rates of antimicrobial efficacy, or kill kinetics. Accuracy and reliability of any short term or intermittent data generation, if available, are questionable because of lack of adequate quality control assays either historically available or run in parallel.

The government and healthcare industry are proposing rules for promoting better antimicrobial stewardship in hospitals, and many industry experts are expecting financial incentives to be implemented in the coming two years. Accordingly, a need exists for a method that rapidly determines antimicrobial susceptibility of a microbial infection. The methods described here are advantageous in that they address this need in a cost-effective manner and can be compatible with existing assay hardware components.

SUMMARY

The present invention is based, in part, on the discovery that methods described herein provide improved rapid determinations of antibiotic susceptibility of microbial infections. The present invention is also based, in part on the surprising discovery that effectiveness and reliability of a rapid Antibiotic Susceptibility Testing (AST) method are greatly increased by accommodating for variability of several factors including the nature and function of a microorganism or antimicrobials, or a combination thereof, thereby generating a versatile, modular and robust platform assay system of the invention.

It is understood that any of the aspects and embodiments described below can be combined in any desired way, and that any embodiment or combination of embodiments can be applied to each of the aspects described below, unless the context indicates otherwise.

In one aspect, the invention provides a method for determining antimicrobial susceptibility of one or more microorganisms comprising performing a plurality of different assays sharing an incubation period, wherein each assay comprises a microorganism growth assay in the presence of one or more antimicrobials, and determining antimicrobial susceptibility of the one or more microorganisms based on relative microorganism growth.

Provided herein are methods of improving the quality of assays for determining antimicrobial susceptibility of one or more microorganisms, by increasing the growth efficiency of the microorganisms for a achieving a suitable threshold level for the assay's performance, whereas, at the same time preventing increase in incubation time for the growth of the microorganisms.

Also provided herein are methods of improving the quality, accuracy and reliability of the assays for determining antimicrobial susceptibility of one or more microorganisms, by preparing and running additional assays simultaneously, without increasing the time required starting from obtaining a sample comprising microorganisms to determining the antimicrobial susceptibility of the microorganisms.

In some embodiments, determining antimicrobial susceptibility of the one or more microorganisms comprises determining a minimum inhibitory concentration (MIC) or a qualitative susceptibility result (QSR) for the one or more antimicrobials.

In some aspects, the invention provides a method for determining antimicrobial susceptibility of one or more microorganisms comprising: performing a plurality of different growth assays sharing an initial incubation period of at least 1.5 hours, wherein one or more probes are added after the completion of the initial incubation period, each assay comprising a microorganism growth assay in the presence of one or more antimicrobials; and determining antimicrobial susceptibility of the one or more microorganisms to one or more antimicrobials based on relative microorganism growth, and a minimum inhibitory concentration (MIC) and/or a qualitative susceptibility result (QSR) can be obtained.

In some aspects, a method of the invention comprises the following steps:
  introducing suspensions of one or more microorganisms to a cartridge comprising a plurality of chambers, wherein a plurality of chambers comprise one or more antimicrobial agents;
  incubating the cartridge under conditions promoting microorganism growth for an initial incubation period;
  performing in a subset of the cartridge chambers, one or more checkpoint assays to determine if microorganism growth has achieved a threshold value; and
(a) if the threshold value is achieved, performing a plurality of different growth assays in a plurality of the cartridge chambers to determine the microorganism's susceptibility to the one or more antimicrobials, and obtaining a minimum inhibitory concentration (MIC) and/or a qualitative susceptibility result (QSR); or (b) if the threshold value is not achieved, performing one or more additional incubation periods under conditions promoting microorganism growth until (i) the threshold value is achieved, and thereafter performing step (a); or (ii) a maximum of 18 hours has transpired without the threshold value being achieved and no further assays are performed.

In one aspect, a method of determining antimicrobial susceptibility of one or more microorganisms is provided, where the method comprises performing a growth assay comprising: incubating a suspension of a microorganism in the presence of one or more antimicrobials without a metabolic probe present; introducing a metabolic probe in an aqueous-miscible solvent after the incubation of the one or more microorganisms; and determining antimicrobial susceptibility of the one or more microorganisms based on relative microorganism growth.

In some embodiments, the method for determining antimicrobial susceptibility of one or more microorganisms comprises incubating a suspension of microorganisms in a plurality of chambers in a cartridge comprising antimicrobial agents for an initial time period to promote microorganism growth, performing one or more checkpoint assays in a subset of the cartridge chambers to determine if relative microorganism growth achieved a threshold value, wherein achieving the threshold value indicates a sufficient growth for the assay system to provide MIC or QSR data for the microorganism, then performing the assay for obtaining the MIC or QSR data.

In some embodiments, the one or more microorganisms are incubated in presence or absence of one or more antimicrobials, under conditions that promote microbial growth for assaying antimicrobial susceptibility of the microorganism.

In some aspects, the invention provides a method for promoting microorganism growth comprising: incubating a suspension of one or more microorganisms in the presence of one or more antimicrobials in a cartridge under conditions promoting microorganism growth; and agitating the cartridge at a frequency and/or an orbital shaking radius insufficient to achieve solution mixing.

In some aspects, the invention provides a method for promoting microorganism growth comprising: preheating a cartridge comprising a suspension of microorganisms to a temperature from about 30° C. to about 45° C.; and incubating the preheated cartridge comprising the suspension of microorganisms in the presence of one or more antimicrobials under conditions promoting microorganism growth.

In some embodiments, the minimum inhibitory concentration (MIC) or the qualitative susceptibility result (QSR) for the one or more antimicrobials is determined from a plurality of assays.

In some embodiments, the number of assays used to determine the minimum inhibitory concentration (MIC) or the qualitative susceptibility result (QSR) for the one or more antimicrobials is smaller than the number of assays performed.

In some embodiments, the number of assays used to determine the minimum inhibitory concentration (MIC) or the qualitative susceptibility result (QSR) for the antimicrobial is equal to the number of assays performed.

In some embodiments, the method further comprises determining whether an assay is appropriate for determining the one or more microorganism's susceptibility to the one or more antimicrobials.

In some embodiments, the method further comprises determining whether an assay is appropriate for determining the one or more microorganism's susceptibility to the one or more antimicrobials.

In some embodiments, different assays are used for different antimicrobial-microorganism combinations. In some embodiments, one or more different assays are used for different microorganism species.

In some embodiments, at least one assay is selected from the group consisting of: a metabolic probe assay, a surface-binding probe assay, a chemical probe assay, a biochemical probe assay, an enzymatic biochemical probe assay, an ATP assay, a nucleic acid probe assay, a double-stranded nucleic acid probe assay, an optical density assay, a visual assay, and a pH molecular probe assay.

In some embodiments, the plurality of growth assays comprises a metabolic assay and a surface-binding assay.

In some embodiments, the metabolic growth assay comprises:

(a) addition of a metabolic probe to a plurality of chambers;

(b) an assay incubation period under conditions promoting microbial growth; and (c) obtaining of one or more of an absorbance, fluorescent, luminescent, electrochemical signal measurement.

In some embodiments, the initial incubation period is from about 2 to 18 hours. In some embodiments, the initial incubation period is from about 2 to 6 hours. In some embodiments, the initial incubation period is about 3 hours.

In some embodiments, the additional time period is between 1 and 18 hours. In some embodiments, the additional incubation period is from about 1 to 4 hours. In some embodiments, the additional incubation period is from about 1 to 2 hours.

In some embodiments, the assay incubation period is from about 30 minutes to 2 hours. In some embodiments, the incubation period is about 3 hours.

In some embodiments, <50%, <25%, <10%, <5%, <2% of the cartridge chambers are used for checkpoint assays.

In some embodiments, one or more checkpoint assay chambers do not comprise antimicrobials. In some embodiments, one or more checkpoint assay chambers comprise one or more antimicrobials.

In some embodiments, a metabolic probe assay is performed before subsequent growth assays. In some embodiments, a metabolic probe assay is performed prior to a surface-binding probe assay.

In some embodiments, the metabolic probe comprises 7-hydroxy-10-oxidophenoxazin-10-ium-3-one (resazurin).

the metabolic probe has a structure according to Formula (I), $$\begin{array}{c} \text{(I)} \\ R^1 \diagup \overset{N}{\underset{N}{\Longleftarrow}} \overset{\overset{\oplus}{\underset{|}{N}} \diagdown ^X}{\underset{N}{\underset{|}{N}}} R^3, \\ \end{array}$$

wherein

R¹ is independently CN, optionally substituted $C_6$-$C_{10}$ aryl, or optionally substituted 5- to 10-membered heteroaryl;

R² is independently optionally substituted $C_6$-$C_{10}$ aryl or optionally substituted 5- to 10-membered heteroaryl;

R³ is independently optionally substituted $C_6$-$C_{10}$ aryl, optionally substituted 5- to 10-membered heteroaryl, or Substructure A;

Substructure A is

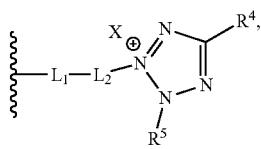

wherein
$L_1$ is independently optionally substituted $C_6$-$C_{10}$ aryl or optionally substituted 5- to 10-membered heteroaryl;

$L_2$ is independently a covalent bond, optionally substituted $C_6$-$C_{10}$ aryl, or optionally substituted 5- to 10-membered heteroaryl;

R⁴ is independently CN, optionally substituted $C_6$-$C_{10}$ aryl, or optionally substituted 5- to 10-membered heteroaryl;

R⁵ is independently optionally substituted $C_6$-$C_{10}$ aryl or optionally substituted 5- to 10-membered heteroaryl;

each X is independently absent or a monovalent anion.

In some embodiments, the metabolic probe comprises 2-(4-Iodophenyl)-3-(4-nitrophenyl)-5-phenyl-2H-tetrazolium chloride (INT), (2-(4-Iodophenyl)-3-(4-nitrophenyl)-5-(2,4-disulfophenyl)-2H-tetrazolium sodium salt (WST-1), 4-[3-(4-Iodophenyl)-2-(2,4-dinitrophenyl)-2H-5-tetrazolio]-1,3-benzene disulfonate (WST-3), or 5-(2,4-disulfophenyl)-3-(2-methoxy-4-nitrophenyl)-2-(4-nitrophenyl)-2H-tetrazolium, inner salt, monosodium salt (WST-8).

In some embodiments, the metabolic probe comprises 2-(4-Iodophenyl)-3-)4-nitrophenyl)-5-phenyl-2H-tetrazolium chloride (INT).

In some embodiments, the surface-binding probe comprises a coordination complex of a lanthanide with diethylenetriaminetetraacetic acid or a cryptate ligand.

In some embodiments, the surface-binding probe comprises

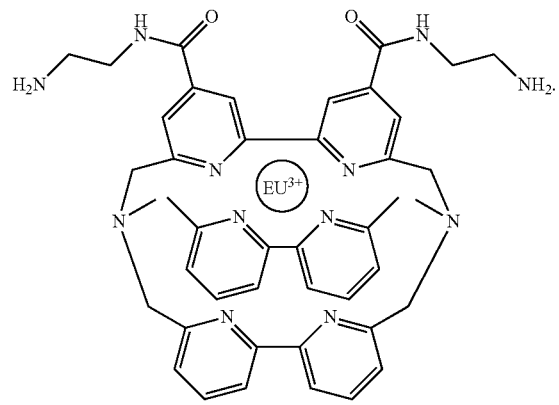

In some embodiments, the indicator comprises europium, strontium, terbium, samarium, and dysprosium, or a combination thereof.

In some embodiments, one or more growth indicators comprise a chemical or biochemical group capable of binding a microorganism cell membrane, cell wall, cell envelope, plasma membrane, cell capsule; within a cell wall, cell envelope, cilium, pilus, flagellum, organelle, transmembrane proteins, cell-wall proteins, extracellular proteins, intracellular proteins, extracellular-associated polysaccharides, intracellular-associated polysaccharides, lipids, extracellular lipids, intracellular lipids, membrane lipids, cell-wall lipids, polysaccharides, and/or lipids integral to or associated with a cell envelop protein, or an organelle, or nucleic acid.

In some embodiments, wherein the assay for determining microorganism growth comprises using an amplifier selected from a group consisting of an enzyme, a catalyst, and a nanoparticle, and a combination thereof.

In some embodiments, the assay for determining microorganism growth comprises an indicator for quantifying double-stranded DNA concentration. In some embodiments, the indicator is ethidium bromide, propidium iodide, SYTOX green, phenanthridines, acridines, indoles, imidazoles, and cyanine, including TOTO, TO-PRO, and SYTO, or a combination thereof. In some embodiments, the assay for determining microorganism growth comprises nucleic acid amplification. In some embodiments, the assay for determining microorganism growth comprises nucleic acid sequencing. In some embodiments, the assay for determining microorganism growth comprises use of adenosine triphosphate.

In some embodiments, the assay for determining microorganism growth comprises light scattering.

In some embodiments, an assay for microorganism growth is based or an absorbance measurement or nephelometric measurement of microorganisms.

In some embodiments, a plurality of different assays are performed in different cartridge chambers.

In some embodiments, a plurality of different assays are performed in the same cartridge chamber.

In some embodiments, a plurality of different assays are performed sequentially.

In some embodiments, a plurality of chambers comprise one or more antimicrobials suspended in a medium.

In some embodiments, a plurality of chambers comprise one or more antimicrobials in the form of an antimicrobial film prior to the introduction of the suspension of microorganisms.

In some embodiments, a plurality of chambers comprises one or more antimicrobials in solid form prior to the introduction of the suspension of microorganisms.

In some embodiments, the one or more antimicrobials are lyophilized or dried.

In some embodiments, the method further comprises determining which antimicrobial or antimicrobial combination is most effective against the one or more microorganisms. Determination of the most effective antimicrobial is a determination of which antimicrobial or combination yields maximal inhibition of the microbial growth in the assay.

In some embodiments, the method further comprises generating a recommendation for treatment of an infection caused by the one or more microorganisms.

In some embodiments, the cartridge is at a temperature of about 35° C. when the assay is performed.

In some embodiments, the metabolic probe is a redox active probe.

In some embodiments, the redox active probe comprises 7-hydroxy-10-oxidophenoxazin-10-ium-3-one (resazurin), 3-(4,5-dimethylthiazol-2-yl)-2,5-diphenyltetrazolium bromide (MTT), 3-(4,5-dimethylthiazol-2-yl)-5-(3-carboxymethoxyphenyl)-2-(4-sulfophenyl)-2H-tetrazolium (MTS), 3,3'-(3,3'-Dimethoxy-4,4'-biphenylene)bis[2,5-bis(p-nitrophenyl)-2H-tetrazolium chloride] (TNBT), 2,3-bis-(2-methoxy-4-nitro-5-sulfophenyl)-2H-tetrazolium-5-carboxanilide (XTT), water-soluble tetrazolium salts (WSTs), (2-(4-Iodophenyl)-3-(4-nitrophenyl)-5-(2,4-disulfophenyl)-2H-tetrazolium sodium salt (WST-1), 4-[3-(4-Iodophenyl)-2-(2,4-dinitrophenyl)-2H-5-tetrazolio]-1,3-benzene disulfonate (WST-3), 2,2'-Dibenzothiazolyl-5,5'-bis[4-di(2-sulfoethyl)carbamoylphenyl]-3,3'-(3,3'-dimethoxy 4,4'-biphenylene)ditetrazolium, disodium salt (WST-5), 5-(2,4-disulfophenyl)-3-(2-methoxy-4-nitrophenyl)-2-(4-nitrophenyl)-2H-tetrazolium, inner salt, monosodium salt (WST-8), 2,3,5-triphenyl-tetrazolium chloride (TTC), 5-cyano-2,3-di(p-tolyl)tetrazolium chloride (CTC), 3,3'(3,3'-dimethoxy-[1,1'-biphenyl]-4,4'-diyl)bis(2-(4-nitrophenyl)-5-phenyl-2H-tetrazol-3-ium) (DBNPT), 3-(naphthalen-1-yl)-2,5-diphenyl-2H-tetrazol-3-ium (NDT), Thiazolyl Blue Tetrazolium Bromide (TBTB), 2-(4-Iodophenyl)-3-(4-nitrophenyl)-5-phenyl-2H-tetrazolium chloride (INT), phenazine methyl sulfate (PMS), phenazine ethyl sulfate (PES), glycylphenylalanyl-aminofluorocoumarin (GF-AFC), 2,2'-bis(4-Nitrophenyl)-5,5'-diphenyl-3,3'-(3,3'-dimethoxy-4,4'-diphenylene)ditetrazolium chloride (NBT), 2,5-Diphenyl-3-(1-naphthyl)tetrazolium chloride (TV), 3,3'-(3,3'-Dimethoxy[1,1'-biphenyl]-4,4'-diyl)-bis(2,5-diphenyl-2H-tetrazolium) dichloride (BTC), 5-Cyano-2,3-bis(4-methylphenyl)-2H-tetrazolium chloride (CTC), 2,3-Bis(2-methoxy-4-nitro-5-sulfophenyl)-2H-tetrazolium-5-carboxanilide inner salt (XTT), RealTime-Glo™, Caspase-Glo®, acetoxymethyl ester of BATDA, ferrocene, dodecylresazurin, dihydrorhodamine 123, dihydrofluorescein, 6-carboxy-2',7'-dichlorodihydro fluorescein diacetate and its acetoxymethyl ester, 2',7'-dichlorodihydrofluorescein diacetate, 5-carboxy-2',7'-dichlorodihydrofluorescein diacetate and its acetoxymethyl ester, chloromethyl-2',7'-dichlorodihydrofluorescein diacetate acetyl ester, dihydrocalcein AM, dihydroethidium, luminol, or 2,3,4,5,6-pentafuorotetramethyldihy droros amine.

In some embodiments, the redox active probe comprises 7-hydroxy-10-oxidophenoxazin-10-ium-3-one (resazurin).

In some embodiments, the redox active probe comprises 2-(4-Iodophenyl)-3-)4-nitrophenyl)-5-phenyl-2H-tetrazolium chloride (INT).

In some embodiments, the redox active probe comprises (2-(4-Iodophenyl)-3-(4-nitrophenyl)-5-(2,4-disulfophenyl)-2H-tetrazolium sodium salt (WST-1), 4-[3-(4-Iodophenyl)-2-(2,4-dinitrophenyl)-2H-5-tetrazolio]-1,3-benzene disulfonate (WST-3), or 5-(2,4-disulfophenyl)-3-(2-methoxy-4-nitrophenyl)-2-(4-nitrophenyl)-2H-tetrazolium, inner salt, monosodium salt (WST-8).

In another aspect, the invention provides for a method for determining antimicrobial susceptibility of one or more microorganisms comprising incubating a suspension of one or more microorganisms and one or more growth indicators for an initial time period to promote microorganism growth and performing one or more checkpoint assays to determine if relative microorganism growth has reached a threshold value, and if the threshold value is reached, performing one or more assays for determining minimum inhibitory concentration (MIC) or qualitative susceptibility result (QSR) for the one or more microorganisms to the one or more antimicrobials; or if the threshold value is not reached, incubating the suspension of one or more microorganisms and the one or more growth indicators for an additional time period if the concentration of the one or more microorganisms has not reached the threshold value and then performing one or more assays for determining minimum inhibitory concentration (MIC) or qualitative susceptibility result (QSR) for the In some embodiments, the one or more checkpoint assays are performed in one or more chambers without a microorganism.

In some embodiments, the one or more checkpoint assays are performed in one or more chambers with one or more antimicrobials of known efficacy against the one or more microorganisms.

In some embodiments, the threshold value is determined by a ratio of a positive control to a background control.

In some embodiments, the positive control comprises a suspension of microorganisms and one or more growth indicators incubated without an antimicrobial.

In some embodiments, the background control comprises a medium and one or more growth indicators incubated without microorganisms.

In some embodiments, the ratio of the positive control to the background control is at least 1.15.

In some embodiments, the incubation of the suspension of microorganisms and the one or more growth indicators for the initial time period occurs prior to performing the one or more checkpoint assays.

In some embodiments, the one or more growth indicators are optically or electrically active during the one or more checkpoint assays.

In some embodiments, the optical signal of the one or more growth indicators comprises fluorescence, time-resolved fluorescence, absorbance or luminescence.

In some embodiments, the electrical signal of the one or more growth indicators is voltammetric or potentiometric.

In some embodiments, the one or more growth indicators are responsive to pH during the checkpoint assay.

In some embodiments, the one or more growth indicators comprise fluorescein, carboxyfluorescein, Eosin Y, 8-hydroxypyrene-1,3,6-trisulfonic acid (pyranine), seminaphthorhodafluors, carboxy SNARFs, alizarin yellow, brilliant yellow, bromocresols, bromophenol blue, bromothymol blue, congo red, o-cresolphthalein, m-cresol purple, cresol red, 2,5-dinitrophenol, ethyl orange, metanil yellow, methyl orange, methyl red, mordant orange, neutral red, phenolphthalein, phenol red, quinaldine red, p-rosolic acid, thymol blue, thymolphthalein, tropaeolin, or xylenol blue.

In some embodiments, the one or more checkpoint assays comprise microscopy or mass spectrometry.

In some embodiments, the method further comprises introducing a suspension of microorganisms to a cartridge comprising a plurality of chambers comprising the one or more antimicrobials.

In some embodiments, the cartridge comprises at least 24 chambers.

In some embodiments, the cartridge comprises 96 or 384 chambers.

In another aspect, the invention provides for a method for promoting microorganism growth comprising incubating a suspension of one or more microorganisms in the presence of one or more antimicrobials in a cartridge under conditions promoting microorganism growth and agitating the cartridge at a frequency or a radius insufficient to achieve solution mixing.

In some embodiments, the cartridge comprises at least 96 chambers.

In some embodiments, the cartridge chambers each have a lateral dimension of less than 12 mm.

In some embodiments, the cartridge is agitated by means of mechanical agitation, acoustic agitation, or magnetic agitation.

In some embodiments, the mechanical agitation is orbital shaking.

In some embodiments, the orbital shaking occurs at a frequency of greater than 50 revolutions per minute.

In some embodiments, the orbital shaking occurs at a frequency of greater than 350 revolutions per minute.

In some embodiments, the orbital shaking occurs at a frequency of less than 750 revolutions per minute.

In some embodiments, the orbital shaking occurs at a frequency of about 150 revolutions per minute.

In some embodiments, the radius is greater than 2 mm.

In some embodiments, the radius is 25 mm.

In some embodiments, agitating the cartridge at a frequency or a radius insufficient to achieve solution mixing results in a greater growth ratio between microorganism growth with agitation of the cartridge as compared to microorganism growth without agitation of the cartridge.

In some embodiments, the growth ratio is greater than 1 and less than 1.5.

In another aspect, the invention provides for a method for promoting microorganism growth comprising preheating a cartridge comprising a suspension of microorganisms to a temperature from about 30° to about 45° C. and incubating the preheated cartridge comprising the suspension of microorganisms in the presence of one or more antimicrobials under conditions promoting microorganism growth.

In some embodiments, the cartridge comprises at least 96 chambers.

In some embodiments, preheating the cartridge to the temperature from between about 30° C. to about 45° C. results in substantially uniform heating of the at least 96 chambers.

In some embodiments, the cartridge is preheated for less than 15 minutes.

In some embodiments, the cartridge is preheated for 1, 2, 5, 10, or 15 minutes.

In some embodiments, the cartridge is preheated by radiative heating, conduction heating, or convection heating.

In some embodiments, the radiative heating is infrared radiative heating.

In some embodiments, the cartridge is preheated by conduction and convection heating.

In some embodiments, one or more heating surfaces perform the conduction and convection heating.

In some embodiments, the cartridge is preheated by both radiative heating and conduction and convection heating.

In some embodiments, the cartridge is not preheated by convection heating alone.

In some embodiments, the cartridge is preheated by an addition of one or more fluids at a temperature of at least 25° C. to the cartridge.

In some embodiments, the incubation of the microorganisms in the presence of one or more antimicrobials occurs within 30 minutes after preheating the cartridge.

In some embodiments, the method further comprises preheating the cartridge prior to loading the cartridge into an automated platform for performing antimicrobial susceptibility testing.

In some embodiments, a variation of temperature across the cartridge is less than 5%.

In some embodiments, the temperature difference in ° C. between the highest-temperature chamber and the lowest-temperature chamber is less than 5%.

In another aspect, the invention provides a method for determining antimicrobial susceptibility of a microorganism comprising introducing a suspension of one or more microorganisms to a cartridge comprising a plurality of chambers comprising one or more antimicrobials, incubating the cartridge under conditions promoting microorganism growth for an initial time period, performing one or more checkpoint assays to determine if the relative microorganism concentration has reached a threshold value, and performing a plurality of different growth assays to determine the one or more microorganism's susceptibility to the one or more antimicrobials.

In some embodiments, the method further comprises incubating the cartridge for an additional time period if relative microorganism growth has not reached the threshold value.

In some embodiments, the threshold value may be a specific value dependent on a microorganism. In some embodiments, the threshold value may be a specific value dependent on the antimicrobial. In some embodiments the threshold value may be a specific value dependent on the microorganism and the antimicrobial.

In some embodiments, the media is liquid, solid, or semi-solid.

In some embodiments, the cartridge comprises at least 2, 4, 6, 8, 12, 24, 48, 96, 192, 384 or 1536 chambers.

In some embodiments, the cartridge further comprises at least one control chamber that does not comprise an antimicrobial or comprises an antimicrobial to which the one or more microorganisms are not susceptible.

In some embodiments, the cartridge is incubated at a temperature of at least 25° C. and not greater than 45° C.

In some embodiments, one or more growth indicators comprise a chemical or biochemical group capable of binding a microorganism cell membrane, cell wall, cell envelope, protein, saccharide, polysaccharide, lipid, organelle, or nucleic acid.

In some embodiments, one or more growth indicators are redox active.

In some embodiments, the growth assays impact microorganism growth or viability.

In some embodiments, a plurality of growth assays are performed in parallel or serially in different chambers.

In some embodiments, the one or more microorganisms derive from a clinical sample.

In some embodiments, the clinical sample comprises blood, cerebrospinal fluid, urine, stool, vaginal, sputum, bronchoalveolar lavage, throat, nasal swabs, wound swab or a combination thereof.

In some embodiments, the one or more microorganisms are selected from the group consisting of: *Enterococcus* spp., *Staphylococcus* spp., *Klebsiella* spp., *Acinetobacter* spp., *Pseudomonas* spp., *Enterobacter* spp., *Streptococcus* spp., *Proteus* spp., *Aerococcus* spp., *Actinomyces* spp., *Bacillus* spp., *Bartonella* spp., *Bordetella* spp., *Brucella* spp., *Campylobacter* spp., *Chlamydia* spp., *Chlamydophila* spp., *Clostridium* spp., *Corynebacterium* spp., *Ehrlichia* spp., *Francisella* spp., *Gardenerella* spp., *Haemophilius* spp., *Helicobacter* spp., *Lactobacillus* spp., *Legionella* spp., *Leptospira* spp., *Listeria* spp., *Mycobacterium* spp., *Mycoplasma* spp., *Neisseria* spp., *Nocardia* spp., *Pasteurella* spp., *Rickettsia* spp., *Salmonella* spp., *Shigella* spp., *Stenotrophomonas* spp., *Treponema* spp., *Ureaplasma* spp., *Vibrio* spp., *Yersinia* spp., *Candida* spp., *Issatchenkia* spp., *Blastomyces* spp., *Coccidioides* spp., *Aspergillus* spp., *Cryptococcus* spp., *Histoplasma* spp., *Pneumocystis* spp., *Stachybotrys* spp.,

*Sporothrix, Exserohilum, Cladosporium,* ringworm, mucormycetes, and a combination thereof.

In some embodiments, the conditions that promote microorganism growth comprise ambient air, anaerobic conditions, or up to 10% $CO_2$.

In some embodiments, the bottom of the cartridge chamber is flat, round, or V-shaped.

In some embodiments, the cartridge is one or more of optically clear, white, or black.

In some embodiments, the microorganism suspension medium comprises at least one nutrient.

In some embodiments, the one or more chambers comprise different liquid constituents.

In some embodiments, the threshold value is determined using background correction.

In some embodiments, the background correction is based on a measurement from one or more chambers.

In some embodiments, a background correction chamber comprises no microorganisms or comprises nonviable microorganisms.

In some embodiments, the plurality of assays determining microorganism growth comprises time-resolved fluorescence measurement of an indicator.

In some embodiments, conditions that promote microorganism growth comprise an incubation period at 31° C.-41° C.

In some embodiments, the checkpoint growth time impacts the determination of the minimum inhibitory concentrations or quantitative susceptibility results.

In some embodiments, different assays measure fluorescence emission from probes that emit light at different wavelengths.

In some aspect, the invention provides a kit comprising all components for performing an assay described in the invention.

Other features and advantages of the invention will be apparent from the drawings and the following detailed description and claims.

BRIEF DESCRIPTION OF THE DRAWINGS

The above and further features will be more clearly appreciated from the following detailed description when taken in conjunction with the accompanying drawings. The drawings however are for illustration purposes only; not for limitation.

FIG. 1 shows that although resazurin can speed the time to AST results when included in the wells during incubation, it can have an inhibitory effects on microbe growth due to resazurin's detrimental effect on bacterial growth.

FIG. 3 shows the differences in growth rates among various clinical samples; clinical bacterial strains can have vastly different growth rates.

FIGS. 4A and 4B show that a growth indicator provides a measurable signal from the checkpoint test wells that can be used as a proxy for growth measured by an endpoint assay. FIGS. 4A and 4B show that resazurin can be used as a checkpoint to determine if bacterial growth has occurred.

FIG. 5 demonstrates the impact of growth rate on resulting AST determinations. A ratio of alamarBlue® (resazurin) signal in an inoculated well to an uninoculated well was used as a growth checkpoint to determine if the AST assay was ready to be processed.

FIGS. 9A and 9B demonstrates that bacteria-specific induction of resazurin fluorescent signal is improved by adding resazurin after bacterial growth.

FIG. 10A shows a graph, where 96-well plates were preheated by radiative heating and reached growth-promoting temperatures in less than 2 minutes. FIG. 10B demonstrates that a single 96-well microplate (with a lid) reached growth-promoting temperatures after about 20 minutes of standard convection heating, and stacked 96-well microplates required a heating time of about 40 minutes to reach these temperatures.

FIG. 11 demonstrates that there was a significant radial distribution of well temperatures that was magnified for the central plates of a 4-plate stack.

FIG. 12A shows data on *E. coli* cultures and FIG. 12B on *P. aeruginosa*, both cultured on 384 well plates.

FIG. 15A shows optical density data on growth of bacteria under shaking and static (not-shaking) conditions. FIG. 15B shows measurement bacterial ATP content of *S. aureus* growth under different shaking speeds of 150 rpm, 250 rpm and 500 rpm as indicated in the figure.

FIGS. 29A and B depicts dual assays determining MICs for each antibiotic, showing comparison of percent correct with values based on algorithmically called MICs. A. Results for *K. pneumoniae*; B. Results for *S. aureus*. Results show more accuracy of either metabolic assays or surface binding assays, depending on the antibiotic.

DEFINITIONS

Figure 1:
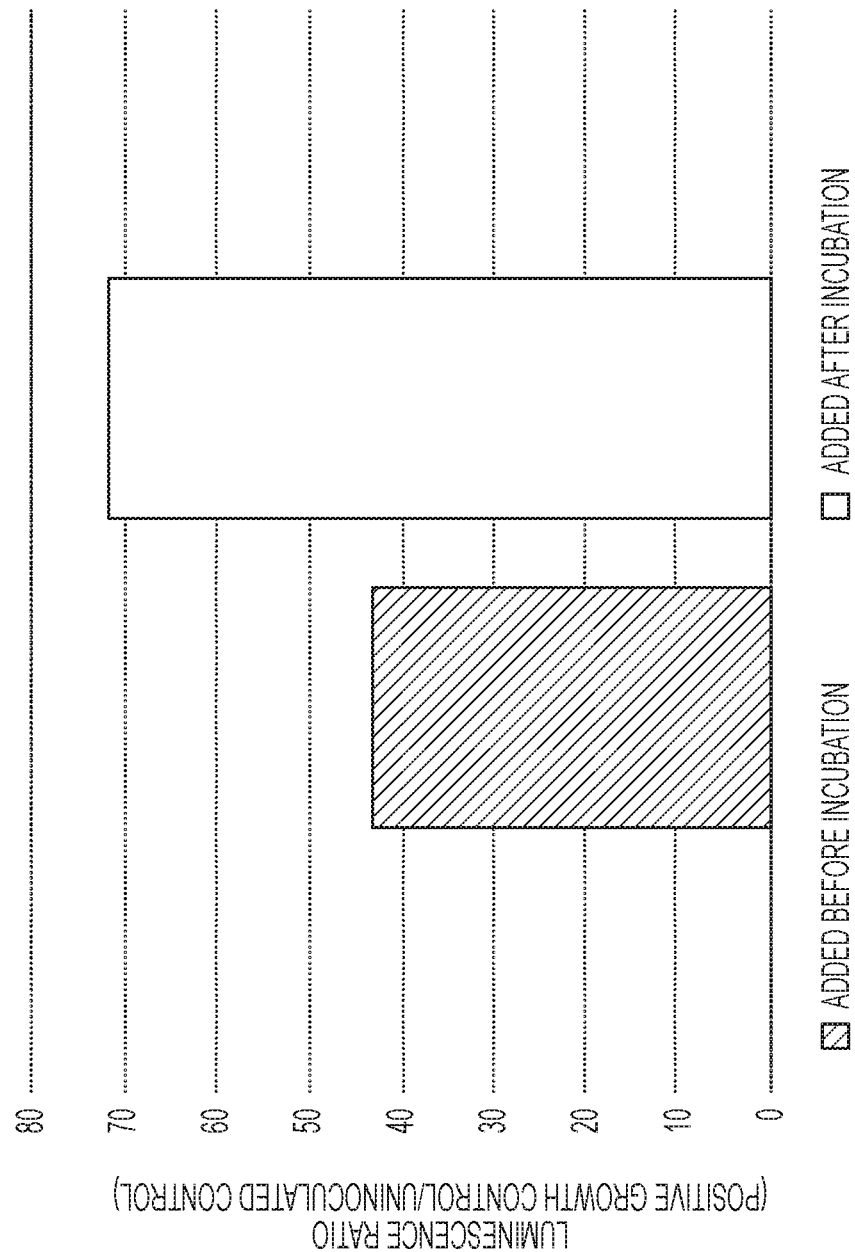
FIG. 1 illustrates growth luminescence ratios post-incubation of microogranisms, where resazurin was introduced to one group of microorganisms before the initial incubation period and the other group was introduced to resazurin after the initial incubation period.

The patent and scientific literature referred to herein establishes knowledge that is available to those of skill in the art. The issued U.S. patents, allowed applications, published U.S. and foreign applications, and references that are cited herein are hereby incorporated by reference to the same extent as if each was specifically and individually indicated to be incorporated by reference.

As used herein, the recitation of a numerical range for a variable is intended to convey that the invention can be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values $>0$ and $<2$ if the variable is inherently continuous.

As used herein, unless specifically indicated otherwise, the word "or" is used in the inclusive sense of "and/or" and not the exclusive sense of "either/or."

As used herein, the term "about" means within +10% of the value it modifies. For example, "about 1" means "0.9 to 1.1", "about 2%" means "1.8% to 2.2%", "about 2% to 3%" means "1.8% to 3.3%", and "about 3% to about 4%" means "2.7% to 4.4%." Unless otherwise clear from the context, all numerical values provided herein are modified by the term "about".

As used herein, the singular forms "a," "an" and "the" include plural referents unless the context clearly dictates otherwise.

The terms "one or more", "at least one", "more than one", and the like are understood to include but not be limited to at least 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149 or 150, 200, 300, 400, 500, 600, 700, 800, 900, 1000, 2000, 3000, 4000, 5000 or more and any number in between.

As used herein, the term "growth assay" refers to an assay that is used to measure microorganism growth or viability. Examples of a growth assay include a checkpoint assay and an endpoint assay.

As used herein, the term "checkpoint assay" refers to an assay that is used to ascertain microbial growth without interfering with it. Typically, a checkpoint assay does not interfere with growth or viability of the microorganism. A checkpoint assay can be performed prior to or concurrently with an endpoint assay.

As used herein, the term "endpoint assay" refers to an assay that is used to determine a microorganism's growth or viability in the presence of an antimicrobial or to determine the microorganism's susceptibility to an antimicrobial. Typically, an endpoint assay interferes with growth or viability of the microorganism. An endpoint assay can be performed concurrently or after the checkpoint assay.

As used herein, the term "growth indicator" refers to a substance that can be used to measure microorganism growth. Typically, a growth indicator is used to measure microorganism growth in the absence of an antimicrobial.

As used herein, unless specifically indicated otherwise, the term "aqueous-miscible solvent" refers to a solvent miscible with water in substantially all proportions.

The term "aliphatic" or "aliphatic group", as used herein, means an optionally substituted straight-chain or branched $C_{1-12}$ hydrocarbon which is completely saturated or which contains one or more units of unsaturation. For example, suitable aliphatic groups include optionally substituted linear or branched alkyl, alkenyl, and alkynyl groups. Unless otherwise specified, in various embodiments, aliphatic groups have 1-12, 1-10, 1-8, 1-6, 1-4, 1-3, or 1-2 carbon atoms. It is apparent to a skilled person in the art that in some embodiments, the "aliphatic" group described herein can be bivalent. The term "alkyl", used alone or as part of a larger moiety, refers to a saturated, optionally substituted straight or branched chain hydrocarbon group having 1-12, 1-10, 1-8, 1-6, 1-4, 1-3, or 1-2 carbon atoms.

The term "alkoxy" refers to a group having the structure —OR, where R is an alkyl group as described herein.

The term "aryl" refers to an optionally substituted $C_{6-14}$ aromatic hydrocarbon moiety comprising one to three aromatic rings. For example, the aryl group is a $C_{6-10}$aryl group (i.e., phenyl and naphthyl). Aryl groups include, without limitation, optionally substituted phenyl, naphthyl, or anthracenyl. The terms "aryl" and "ar-", as used herein, also include groups in which an aryl ring is fused to one or more cycloaliphatic rings to form an optionally substituted cyclic structure such as a tetrahydronaphthyl, indenyl, or indanyl ring. The term "aryl" may be used interchangeably with the terms "aryl group", "aryl ring", and "aromatic ring".

The term "cycloaliphatic" refers to an optionally substituted saturated or partially unsaturated cyclic aliphatic ring system having from 3 to about 14 ring carbon atoms. Cycloaliphatic groups include, without limitation, optionally substituted cyclopropyl, cyclobutyl, cyclopentyl, cyclopentenyl, cyclohexyl, cyclohexenyl, cycloheptyl, cycloheptenyl, cyclooctyl, cyclooctenyl, or cyclooctadienyl.

The term "halogen" or "halo" means F, Cl, Br, or I.

The term "heteroaryl" refers to groups having 5 to 14 ring atoms, preferably 5, 6, 9, or 10 ring atoms; having 6, 10, or 14 □ electrons shared in a cyclic array; and having, in addition to carbon atoms, from one to five heteroatoms. A heteroaryl group may be mono-, bi-, tri-, or polycyclic, for example, mono-, bi-, or tricyclic (e.g., mono- or bicyclic). The term "heteroatom" refers to nitrogen, oxygen, or sulfur, and includes any oxidized form of nitrogen or sulfur, and any quaternized form of a basic nitrogen. For example, a nitrogen atom of a heteroaryl may be a basic nitrogen atom and may also be optionally oxidized to the corresponding N-oxide. When a heteroaryl is substituted by a hydroxy group, it also includes its corresponding tautomer. The terms "heteroaryl" and "heteroar-", as used herein, also include groups in which a heteroaromatic ring is fused to one or more aryl, cycloaliphatic, or heterocycloaliphatic rings. Nonlimiting examples of heteroaryl groups include thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, pteridinyl, indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. The term "heteroaryl" may be used interchangeably with the terms "heteroaryl ring", "heteroaryl group", or "heteroaromatic", any of which terms include rings that are optionally substituted.

As used herein, the terms "heterocycle", "heterocyclyl", "heterocyclic radical", and "heterocyclic ring" are used interchangeably and refer to a stable 3- to 8-membered monocyclic or 7-10-membered bicyclic heterocyclic moiety that is either saturated or partially unsaturated, and having, in addition to carbon atoms, one or more, such as one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $NR^+$ (as in N-substituted pyrrolidinyl).

Affixing the suffix "-ene" to a group indicates the group is a divalent moiety, e.g., arylene is the divalent moiety of aryl, and heteroarylene is the divalent moiety of heteroaryl.

The phrase "one or more substituents", as used herein, refers to a number of substituents that equals from one to the maximum number of substituents possible based on the number of available bonding sites, provided that the above conditions of stability and chemical feasibility are met.

An aryl (including aralkyl, aralkoxy, aryloxyalkyl and the like), heteroaryl (including heteroaralkyl and heteroarylalkoxy and the like) group may contain one or more substituents and thus may be "optionally substituted". In addition to the substituents defined above and herein, suitable substituents on the unsaturated carbon atom of an aryl group (e.g., phenyl or naphthyl) or heteroaryl group (e.g., pyridyl) also include and are generally selected from -halo, $-NO_2$, $-CN$, $-R^+$, $-C(R^+)=C(R^+)_2$, $-C\equiv C-R^+$, $-OR^+$, $-SR^\circ$, $-S(O)R^\circ$, $-SO_2R^\circ$, $-SO_3R^+$, $-SO_2N(R^+)_2$, $-N(R^+)_2$, $-NR^+C(O)R^+$, $-NR^+C(S)R^+$, $-NR^+C(O)N(R^+)_2$, $-NR^+C(S)N(R^+)_2$, $-N(R^+)C(=NR^+)-N(R^+)_2$, $-N(R^+)C(=NR^+)-R^\circ$, $-NR^+CO_2R^+$, $-NR^+SO_2R^\circ$, $-NR^+SO_2N(R^+)_2$, $-O-C(O)R^+$, $-O-CO_2R^+$, $-OC(O)N(R^+)_2$, $-C(O)R^+$, $-C(S)R^\circ$, $-CO_2R^+$, $-C(O)-C(O)R^+$, $-C(O)N(R^+)_2$, $-C(S)N(R^+)_2$, $-C(O)N(R^+)-OR^+$, $-C(O)N(R^+)C(=NR^+)-N(R^+)_2$, $-N(R^+)C(=NR^+)-N(R^+)-C(O)R^+$, $-C(=NR^+)-N(R^+)_2$, $-C(=NR^+)-OR^+$, $-N(R^+)-N(R^+)_2$, $-C(=NR^+)-N(R^+)-OR^+$, $-C(R^\circ)=N-OR^+$, $-P(O)(R^+)_2$, $-P(O)(OR^+)_2$, $-O-P(O)-OR^+$, and $-P(O)(NR^+)-N(R^+)_2$, wherein $R^+$, independently, is hydrogen or an optionally substituted aliphatic, aryl, heteroaryl, cycloaliphatic, or heterocyclyl group. Each $R^\circ$ is an optionally substituted aliphatic, aryl, heteroaryl, cycloaliphatic, or heterocyclyl group.

An alkyl or alkoxy group may contain one or more substituents and thus may be "optionally substituted". Unless otherwise defined above and herein, suitable substituents on the saturated carbon of an alkyl or alkoxy group are selected from those listed above for the unsaturated carbon of an aryl or heteroaryl group and additionally include the following: $=O$, $=S$, $=C(R^*)_2$, $=N-N(R^*)_2$, $=N-OR^*$, $=N-NHC(O)R^*$, $=N-NHCO_2R^\circ=N-NHSO_2R^\circ$ or $=N-R^*$ where $R^\circ$ is defined above, and each $R^*$ is independently selected from hydrogen or an optionally substituted $C_{1-6}$ aliphatic group.

For the purposes of the surface binding assay, "surface binding probe" may be used interchangeably with "signaling agent."

Binding of the surface binding probe may comprise one or more of ionic bonds, covalent bonds, dative bonds, electrostatic interaction, hydrogen bonds, and van der Waal bonds.

The term "growth assay" may be used interchangeably with "viability assay," in particular in the case of metabolic probe assays.

For surface binding probes comprising lanthanide chelates, the term "time resolved fluorescence" is defined herein to be interchangeable with "time-gated luminescence." The units for these measurements may therefore be defined to be any of the following: relative fluorescence units, relative light units, relative luminescence units, relative luminescence intensity (arbitrary units), relative light intensity (arbitrary units).

For the purposes of agitation, mixing is defined as turbulent mixing, in which random structures produced by fluid instability at high Renolds number stretch and fold fluid elements.

As used herein, absorbance measurement indicates measurement of the optical density of the microorganism culture. Optical density is measured by the absorbance of a certain frequency of incident light, such that the absorbance is proportional to the number of microorganisms present in the culture over a certain range. As used herein, nephelometric studies indicate determining the amount of cloudiness, or turbidity, in a solution based upon measurement of the effect of this turbidity upon the transmission and scattering of light.

As used herein, shaking and agitating are used interchangeably in the context of a microbial culture cartridge or assay cartridge. Shaking of the microbial culture or assay plates can be performed in a rotator shaker or a platform, an orbital shaker.

Unless otherwise defined, all technical and scientific terms used herein have the same meaning as commonly understood by one of ordinary skill in the art to which this application belongs and as commonly used in the art to which this application belongs; such art is incorporated by reference in its entirety. In the case of conflict, the present Specification, including definitions, will control.

DETAILED DESCRIPTION

The rapid AST methods described herein can provide accurate results that are consistent with results obtained using the Clinical Laboratory Standards Institute (CLSI) reference methods when tested with multiple antimicrobials and on a plurality of microorganisms; however, these methods can require significantly less time to provide results than the CLSI methods. The methods described herein, in a greatly reduced amount of time and expense, relative to standard methods, can provide a patient with an appropriate treatment regimen, i.e., a specific antimicrobial and at a particular dosage. Thus, the methods described herein can improve patient outcomes, lower hospital costs, and help reduce further evolution of antimicrobial resistant microorganisms; thus, the methods described herein represent a significant breakthrough in the AST field.

The methods provided by the present application are, in one aspect, intended to be performed in conjunction with rapid AST methods, such as those described in PCT/US17/14343 and devices such as those described in PCT/US17/28906, which are incorporated by reference herein in their entirety.

For example, a rapid AST method can provide for introducing a suspension of microorganisms to a cartridge comprising a plurality of chambers comprising antimicrobials at pre-determined antimicrobial concentrations. A cartridge can be a multi-well plate. A cartridge comprises one or more reservoirs of wells. In some embodiments, the cartridge is a microplate. The cartridge can comprise at least 2, 4, 6, 8, 12, 24, 48, 96, 192, 384, or 1536 chambers. Further, cartridge chambers can be wells or reservoirs on a microplate. The suspension of microorganisms can comprise medium that comprises at least one nutrient.

Further, a rapid AST method can include incubating the cartridge for a time period under conditions promoting microorganism growth. The incubation time period can occur for about 1 hour, 2 hours, 3 hours, 4 hours, 5 hours, or 6 hours. The initial incubation, in some embodiments, occurs for a time period from about 1 to 2 hours, from about 1 to 3 hours, from about 1 to 4 hours, from about 1 to 5 hours, from about 1 to 6 hours, from about 2 to 3 hours, from about 2 to 4 hours, from about 2 to 5 hours, from about 2 to 6 hours, from about 3 to 4 hours, from about 3 to 5 hours, from about 3 to 6 hours, from about 4 to 5 hours, from about 4 to 6 hours, or from about 5 to 6 hours. In some embodiments, the initial incubation period is about 3 hours.

Finally, a rapid AST method can provide for performing a growth assay in order to determine a microorganism's susceptibility to an antimicrobial. Growth assays can be viability assays. Non-limiting examples of growth assays can include a metabolic probe assay, a surface-binding probe assay, a chemical probe assay, a biochemical probe assay, an ATP assay, a nucleic acid probe assay, a double-stranded nucleic acid probe assay, an optical density assay, a visual assay, or a pH molecular probe assay.

As is known to those skilled in the art, AST platforms can yield minimum inhibitory concentration (MIC) results and/or qualitative susceptibility results (QSRs) for each antimicrobial tested. According to CLSI Microbiology standards, an MIC of a given antibiotic for a given species and strain of a microorganism can be defined as the lowest concentration of the antibiotic in two-fold dilution series that inhibits growth of the microorganism and can provide physicians with dosing information. QSRs can also provide physicians with similar dosing information but cannot provide a numerical MIC.

AST assays can be predominantly configured to test multiple antimicrobials in parallel for each obtained biological sample. In order to produce MIC or QSR results, dilution series can be required for each antimicrobial. Thus, for liquid-based ASTs, termed "broth microdilution" by the CLSI, assays are commonly performed in cartridges and/or microplates, which enable parallel testing of different antimicrobials at different concentrations. These MICs, along with the microorganism species and antimicrobial, are used to determine the Clinical & Laboratory Standards Institute (CLSI) breakpoint interpretation to provide the clinical AST result for each combination of microorganism species and antimicrobial. Such results take the form of Susceptible (S), Intermediate (I), Resistant (R), Not Susceptible (NS), and No Interpretation (NI) per CLSI publication M-100S.

As disclosed, (e.g., in the Examples), the methods described herein have been shown to deliver equivalent results to the gold-standard for a broad range of microorganism species, including all six (*Enterococcus faecium, Staphylococcus aureus, Klebsiella pneumoniae, Acinetobacter baumannii, Pseudomonas aeruginosa*, and *Enterobacter* species) ("ESKAPE") pathogens. The methods described herein can be easily and cheaply adapted to new microorganism species strains and diagnostic tests.

In some embodiments, the method provides for determining antimicrobial susceptibility of a microorganism by introducing a suspension of microorganisms to a cartridge comprising a plurality of chambers comprising an antimicrobial; incubating the cartridge under conditions promoting microorganism growth for an initial time period; performing a checkpoint assay to determine if the relative microorganism concentration has reached a threshold value; and performing a plurality of different growth assays to determine the microorganism's susceptibility to the antimicrobial.

In some embodiments, the methods described herein are performed in an automated platform for antimicrobial susceptibility testing.

Plurality of Different Assays

AST methods can perform assays that can be useful for determining MICs or QSRs in certain bacterial strains. Instances occur where one type of assay is more effective for particular strains of microorganisms over others in determining the microorganism's susceptibility to an antimicrobial. The methods described herein provide for a way to determine which of the plurality of different assays, if any, can be appropriate for determining a microorganism's susceptibility to an antimicrobial. In some embodiments, the method uses a different assay for a different antimicrobial-antibiotic combination.

Each growth assay can be selected from a group of endpoint assays such as a metabolic probe assay, a surface-binding probe assay, a chemical probe assay, a biochemical probe assay, an ATP assay, a nucleic acid probe assay, a double-stranded nucleic acid probe assay, an optical density assay, measurement for microorganism mass, a visual assay, or a pH molecular probe assay.

The plurality of different assays can be performed in parallel, where the growth assay (e.g., an endpoint assay) provides a determination of antimicrobial susceptibility for a given microorganism. The AST method can be run on a cartridge as described above. In some embodiments, the plurality of different assays is performed in different cartridge chambers. In some embodiments, the same assay is performed in a particular row or column of chambers on a cartridge.

In some embodiments, a plurality of different assays run in parallel means that the assays share an incubation period for microorganism growth. In some embodiments, the assays run in parallel are performed sequentially. In some embodiments, the assays run in parallel are performed in the same cartridge chamber. In some embodiments, the assays run in parallel overlap.

In some embodiments, the invention provides for performing a metabolic probe assay and a surface-binding probe assay in order to enable accurate rapid determination of a microorganism's susceptibility to an antimicrobial in less than 3, 3.5, 4, 4.5, 5, 5.5, 6, 6.5, 7, 7.5, or 8 hours, as compared to the Clinical Laboratory Standards Institute (CLSI) overnight reference method. In some embodiments, the metabolic probe assay is performed before the surface-binding probe assay. Cumulatively, data from these two assays can enable accurate determination of the antimicrobial's MICs; thus, in some embodiments, the invention, in a greatly reduced amount of time relative to standard methods, provides a patient with an appropriate treatment regimen, e.g., a specific antimicrobial and at a particular dosage.

The metabolic probe assay can utilize a metabolic probe that is present in an aqueous-miscible solvent. Thus, in some embodiments, the introduction of the metabolic probe does not result in an emulsion. Introducing a probe in an emulsion can be inconvenient in small chambers and can lead to inconsistent results. In some embodiments, the metabolic probe is hydrophilic or substantially hydrophilic. In some embodiments, the metabolic probe assay uses a metabolic probe that is a redox active probe. Non-limiting examples of redox active probes that can be introduced during the metabolic probe assay can include 7-hydroxy-10-oxidophenoxazin-10-ium-3-one (resazurin), 3-(4,5-dimethylthiazol-2-yl)-2,5-diphenyltetrazolium bromide (MTT), 3-(4,5-dimethylthiazol-2-yl)-5-(3-carboxymethoxyphenyl)-2-(4-sulfophenyl)-2H-tetrazolium (MTS), 3,3'-(3,3'-Dimethoxy-4,4'-biphenylene)bis[2,5-bis(p-nitrophenyl)-2H-tetrazolium chloride] (TNBT), 2,3-bis-(2-methoxy-4-nitro-5-sulfophenyl)-2H-tetrazolium-5-carboxanilide (XTT), water-soluble tetrazolium salts (WSTs), (2-(4-Iodophenyl)-3-(4-nitrophenyl)-5-(2,4-disulfophenyl)-2H-tetrazolium sodium salt (WST-1), 4-[3-(4-Iodophenyl)-2-(2,4-dinitrophenyl)-2H-5-tetrazolio]-1,3-benzene disulfonate (WST-3), 2,2'-Dibenzothiazolyl-5,5'-bis[4-di(2-sulfoethyl)carbamoylphenyl]-3,3'-(3,3'-dimethoxy 4,4'-biphenylene)ditetrazolium, disodium salt (WST-5), 5-(2,4-disulfophenyl)-3-(2-methoxy-4-nitrophenyl)-2-(4-nitrophenyl)-2H-tetrazolium, inner salt, monosodium salt (WST-8), 2,3,5-triphenyl-tetrazolium chloride (TTC), 5-cyano-2,3-di(p-tolyl)tetrazolium chloride (CTC), 3,3'(3,3'-dimethoxy-[1,1'-biphenyl]-4,4'-diyl)bis(2-(4-nitrophenyl)-5-phenyl-2H-tetrazol-3-ium)(DBNPT), 3-(naphthalen-1-yl)-2,5-diphenyl-2H-tetrazol-3-ium (NDT), Thiazolyl Blue Tetrazolium Bromide (TBTB), 2-(4-Iodophenyl)-3-(4-nitrophenyl)-5-phenyl-2H-tetrazolium chloride (INT), phenazine methyl sulfate (PMS), phenazine ethyl sulfate (PES), glycylphenylalanyl-aminofluorocoumarin (GF-AFC), 2,2'-bis(4-Nitrophenyl)-5,5'-diphenyl-3,3'-(3,3'-dimethoxy-4,4'-diphenylene)ditetrazolium chloride (NBT), 2,5-Diphenyl-3-(1-naphthyl)tetrazolium chloride (TV), 3,3'-(3,3'-Dimethoxy[1,1'-biphenyl]-4,4'-diyl)-bis(2,5-diphenyl-2H-tetrazolium) dichloride (BTC), 5-Cyano-2,3-bis(4-methylphenyl)-2H-tetrazolium chloride (CTC), 2,3-Bis(2-methoxy-4-nitro-5-sulfophenyl)-2H-tetrazolium-5-carboxanilide inner salt (XTT), RealTime-Glo™, Caspase-Glo®, acetoxymethyl ester of BATDA, ferrocene, dodecylresazurin, dihydrorhodamine 123, dihydrofluorescein, 6-carboxy-2',7'-dichlorodihydro fluorescein diacetate and its acetoxymethyl ester, 2',7'-dichlorodihydrofluorescein diacetate, 5-carboxy-2',7'-dichlorodihydrofluorescein diacetate and its acetoxymethyl ester, chloromethyl-2',7'-dichlorodihydrofluorescein diacetate acetyl ester, dihydrocalcein AM, dihydroethidium, luminol, or 2,3,4,5,6-pentafuorotetramethyldihy droros amine.

In some embodiments, suitable metabolic probes are well known to those skilled in the art and are described in *The Molecular Probes® Handbook: A Guide to Fluorescent Probes and Labeling Technologies*, 11$^{th}$ Ed. (2010) (see, e.g., Chapter 15, "Assays for Cell Viability, Proliferation and Function") and Riss T L, Moravec R A, Niles A L, et al. Cell Viability Assays. 2013 May 1 [Updated 2016 Jul. 1]. In: Sittampalam G S, Coussens N P, Nelson H, et al., editors. Assay Guidance Manual [Internet]. Bethesda (Md.): Eli Lilly & Company and the National Center for Advancing Translational Sciences; 2004-. and U.S. Pat. No. 7,897,331, which are herein incorporated by reference in their entirety.

In some embodiments, the redox active probe has a structure according to Formula (I),

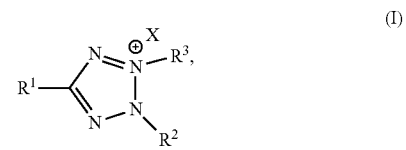

wherein

R$^1$ is independently CN, optionally substituted C$_6$-C$_{10}$ aryl, or optionally substituted 5- to 10-membered heteroaryl;

R² is independently optionally substituted C₆-C₁₀ aryl or optionally substituted 5- to 10-membered heteroaryl;

R³ is independently optionally substituted C₆-C₁₀ aryl, optionally substituted 5- to 10-membered heteroaryl, or Substructure A;

Substructure A is

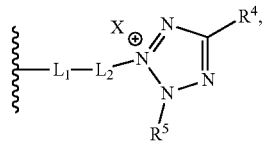

wherein

L₁ is independently optionally substituted C₆-C₁₀ aryl or optionally substituted 5- to 10-membered heteroaryl;

L₂ is independently a covalent bond, optionally substituted C₆-C₁₀ aryl, or optionally substituted 5- to 10-membered heteroaryl;

R⁴ is independently CN, optionally substituted C₆-C₁₀ aryl, or optionally substituted 5- to 10-membered heteroaryl;

R⁵ is independently optionally substituted C₆-C₁₀ aryl or optionally substituted 5- to 10-membered heteroaryl;

each X is independently absent or a monovalent anion.

In some embodiments, R¹ is independently CN or optionally substituted C₆-C₁₀ aryl (e.g., phenyl substituted by 0, 1, 2, 3, 4, or 5 substituent groups). In some embodiments, R¹ is independently CN. In some embodiments, R¹ is independently unsubstituted phenyl or unsubstituted naphthyl. In some embodiments, R¹ is independently substituted C₆-C₁₀ aryl (e.g., phenyl substituted by 1, 2, 3, 4, or 5 substituent groups). In some embodiments, R¹ is independently a C₆-C₁₀ aryl (e.g., phenyl) having 1, 2, 3, 4, or 5 substituent groups independently selected from: C₁₋₆ alkyl (e.g., methyl, ethyl, n-propyl, or isopropyl); C₁₋₆ alkoxy (e.g., methoxy, ethoxy, n-propyloxy, or isopropyloxy); halogen (e.g., F, Cl, Br, or I); —CN; nitro; and sulfonic acid or an ionized form thereof (e.g., —SO₃H or —SO₃Na). In some embodiments, R¹ is independently a C₆-C₁₀ aryl (e.g., phenyl) having 1, 2, 3, 4, or 5 substituent groups independently selected from: C₁₋₆ alkyl (e.g., methyl, ethyl, n-propyl, or isopropyl); C₁₋₆ alkoxy (e.g., methoxy, ethoxy, n-propyloxy, or isopropyloxy); halogen (e.g., F, Cl, Br, or I); —CN; and nitro.

In some embodiments, R² is independently optionally substituted C₆-C₁₀ aryl (e.g., phenyl substituted by 0, 1, 2, 3, 4, or 5 substituent groups). In some embodiments, R² is independently unsubstituted phenyl or unsubstituted naphthyl. In some embodiments, R² is independently substituted C₆-C₁₀ aryl (e.g., phenyl substituted by 1, 2, 3, 4, or 5 substituent groups). In some embodiments, R² is independently a C₆-C₁₀ aryl (e.g., phenyl) having 1, 2, 3, 4, or 5 substituent groups independently selected from: C₁₋₆ alkyl (e.g., methyl, ethyl, n-propyl, or isopropyl); C₁₋₆ alkoxy (e.g., methoxy, ethoxy, n-propyloxy, or isopropyloxy); halogen (e.g., F, Cl, Br, or I); —CN; and nitro.

In some embodiments, R³ is independently optionally substituted C₆-C₁₀ aryl (e.g., phenyl substituted by 0, 1, 2, 3, 4, or 5 substituent groups). In some embodiments, R³ is independently unsubstituted phenyl or unsubstituted naphthyl. In some embodiments, R³ is independently substituted C₆-C₁₀ aryl (e.g., phenyl substituted by 1, 2, 3, 4, or 5 substituent groups). In some embodiments, R³ is independently a C₆-C₁₀ aryl (e.g., phenyl) having 1, 2, 3, 4, or 5 substituent groups independently selected from: C₁₋₆ alkyl (e.g., methyl, ethyl, n-propyl, or isopropyl); C₁₋₆ alkoxy (e.g., methoxy, ethoxy, n-propyloxy, or isopropyloxy); halogen (e.g., F, Cl, Br, or I); —CN; and nitro.

In some embodiments, X is a monovalent anion (e.g., Cl⁻ or Br⁻). In further embodiments, R¹ is independently CN or optionally substituted C₆-C₁₀ aryl (e.g., phenyl substituted by 1, 2, 3, 4, or 5 substituent groups selected from: C₁₋₆ alkyl (e.g., methyl, ethyl, n-propyl, or isopropyl); C₁₋₆ alkoxy (e.g., methoxy, ethoxy, n-propyloxy, or isopropyloxy); halogen (e.g., F, Cl, Br, or I); —CN; and nitro).

In some embodiments, X is absent. In further embodiments, R¹ is independently substituted C₆-C₁₀ aryl comprising a substituent that is an ionized sulfonic acid group.

In some embodiments, R³ is Substructure A, and the compound has a structure according to Formula (II):

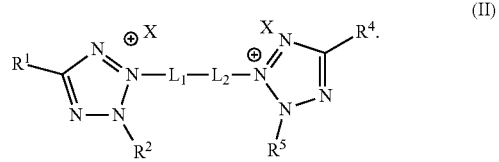

(II)

In embodiments, L₁ is optionally substituted C₆-C₁₀ arylene, and L₂ is a covalent bond.

In embodiments, each of L₁ and L₂ is independently optionally substituted C₆-C₁₀ arylene. In embodiments, each of L₁ and L₂ is independently optionally substituted phenylene. In embodiments, each of L₁ and L₂ is unsubstituted phenylene. In embodiments, each of L₁ and L₂ is independently substituted phenylene having 1, 2, 3, or 4 substituent groups independently selected from: C₁₋₆ alkyl (e.g., methyl, ethyl, n-propyl, or isopropyl); C₁₋₆ alkoxy (e.g., methoxy, ethoxy, n-propyloxy, or isopropyloxy); halogen (e.g., F, Cl, Br, or I); —CN; and nitro. In embodiments, each of L₁ and L₂ is independently substituted phenylene comprising a C₁₋₆ alkoxy (e.g., methoxy, ethoxy, n-propyloxy, or isopropyloxy).

In some embodiments, R⁴ is independently CN or optionally substituted C₆-C₁₀ aryl (e.g., phenyl substituted by 0, 1, 2, 3, 4, or 5 substituent groups). In some embodiments, R⁴ is independently CN. In some embodiments, R⁴ is independently unsubstituted phenyl or unsubstituted naphthyl. In some embodiments, R⁴ is independently substituted C₆-C₁₀ aryl (e.g., phenyl substituted by 1, 2, 3, 4, or 5 substituent groups). In some embodiments, R⁴ is independently a C₆-C₁₀ aryl (e.g., phenyl) having 1, 2, 3, 4, or 5 substituent groups independently selected from: C₁₋₆ alkyl (e.g., methyl, ethyl, n-propyl, or isopropyl); C₁₋₆ alkoxy (e.g., methoxy, ethoxy, n-propyloxy, or isopropyloxy); halogen (e.g., F, Cl, Br, or I); —CN; nitro; and sulfonic acid or an ionized form thereof (e.g., —SO₃H or —SO₃Na). In some embodiments, R⁴ is independently a C₆-C₁₀ aryl (e.g., phenyl) having 1, 2, 3, 4, or 5 substituent groups independently selected from: C₁₋₆ alkyl (e.g., methyl, ethyl, n-propyl, or isopropyl); C₁₋₆ alkoxy (e.g., methoxy, ethoxy, n-propyloxy, or isopropyloxy); halogen (e.g., F, Cl, Br, or I); —CN; and nitro.

In some embodiments, R¹ and R⁴ are the same group. In some embodiments, each of R¹ and R⁴ is a C₆-C₁₀ aryl (e.g., phenyl) having 0, 1, 2, 3, 4, or 5 substituent groups independently selected from: C₁₋₆ alkyl (e.g., methyl, ethyl, n-propyl, or isopropyl); C₁₋₆ alkoxy (e.g., methoxy, ethoxy, n-propyloxy, or isopropyloxy); halogen (e.g., F, Cl, Br, or I); —CN; nitro; and sulfonic acid or an ionized form thereof (e.g., —SO₃H or —SO₃Na). In some embodiments, each of R¹ and R⁴ is a $C_6$-$C_{10}$ aryl (e.g., phenyl) having 0, 1, 2, 3, 4, or 5 substituent groups independently selected from: $C_{1-6}$ alkyl (e.g., methyl, ethyl, n-propyl, or isopropyl); $C_{1-6}$ alkoxy (e.g., methoxy, ethoxy, n-propyloxy, or isopropyloxy); halogen (e.g., F, Cl, Br, or I); —CN; and nitro.

In some embodiments, $R^5$ is independently optionally substituted $C_6$-$C_{10}$ aryl (e.g., phenyl substituted by 0, 1, 2, 3, 4, or 5 substituent groups). In some embodiments, $R^5$ is independently unsubstituted phenyl or unsubstituted naphthyl. In some embodiments, $R^5$ is independently substituted $C_6$-$C_{10}$ aryl (e.g., phenyl substituted by 1, 2, 3, 4, or 5 substituent groups). In some embodiments, $R^5$ is independently a $C_6$-$C_{10}$ aryl (e.g., phenyl) having 1, 2, 3, 4, or 5 substituent groups independently selected from: $C_{1-6}$ alkyl (e.g., methyl, ethyl, n-propyl, or isopropyl); $C_{1-6}$ alkoxy (e.g., methoxy, ethoxy, n-propyloxy, or isopropyloxy); halogen (e.g., F, Cl, Br, or I); —CN; and nitro.

In some embodiments, $R^2$ and $R^5$ are the same group. In some embodiments, each of $R^2$ and $R^5$ is a $C_6$-$C_{10}$ aryl (e.g., phenyl) having 0, 1, 2, 3, 4, or 5 substituent groups independently selected from: $C_{1-6}$ alkyl (e.g., methyl, ethyl, n-propyl, or isopropyl); $C_{1-6}$ alkoxy (e.g., methoxy, ethoxy, n-propyloxy, or isopropyloxy); halogen (e.g., F, Cl, Br, or I); —CN; nitro; and sulfonic acid or an ionized form thereof (e.g., —$SO_3H$ or —$SO_3Na$). In some embodiments, each of $R^2$ and $R^5$ is a $C_6$-$C_{10}$ aryl (e.g., phenyl) having 0, 1, 2, 3, 4, or 5 substituent groups independently selected from: $C_{1-6}$ alkyl (e.g., methyl, ethyl, n-propyl, or isopropyl); $C_{1-6}$ alkoxy (e.g., methoxy, ethoxy, n-propyloxy, or isopropyloxy); halogen (e.g., F, Cl, Br, or I); —CN; and nitro.

In some embodiments, each X is a monovalent anion (e.g., each X is independently Cl⁻ or Br⁻). In further embodiments, each $R^1$ and $R^4$ is independently CN or optionally substituted $C_6$-$C_{10}$ aryl (e.g., phenyl substituted by 1, 2, 3, 4, or 5 substituent groups selected from: $C_{1-6}$ alkyl (e.g., methyl, ethyl, n-propyl, or isopropyl); $C_{1-6}$ alkoxy (e.g., methoxy, ethoxy, n-propyloxy, or isopropyloxy); halogen (e.g., F, Cl, Br, or I); —CN; and nitro). In some embodiments, $R^1$ and $R^4$ are the same group.

Exemplary compounds of Formula (I) are listed in Table 1.

TABLE 1

Exemplary Compounds of Formula (I)

| No. | Abbreviation | Chemical Structure and Name |
|---|---|---|
| (1) | TTC | 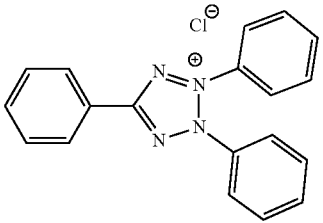 [SMILES: c1ccc(-c2nn(-c3ccccc3)[n+](-c3ccccc3)n2)cc1 ; [Cl-]]<br>2,3,5-triphenyl-tetrazolium chloride |
| (2) | CTC | 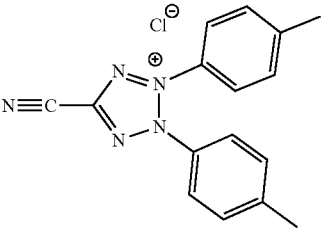 [SMILES: Cc1ccc(-n2nc(C#N)n[n+]2-c2ccc(C)cc2)cc1 ; [Cl-]]<br>5-cyano-2,3-di(p-tolyl)tetrazolium chloride |
| (3) | DBNPT | 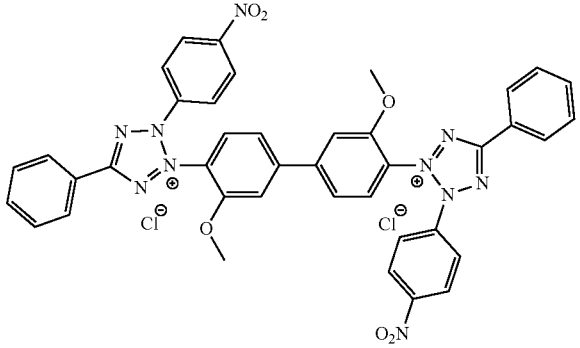 [SMILES: COc1cc(-c2ccc(-[n+]3nc(-c4ccccc4)nn3-c3ccc([N+](=O)[O-])cc3)c(OC)c2)ccc1-[n+]1nc(-c2ccccc2)nn1-c1ccc([N+](=O)[O-])cc1 ; [Cl-] ; [Cl-]]<br>3,3'-(3,3'-dimethoxy-[1,1'-biphenyl]-4,4'-diyl)bis(2-(4-nitrophenyl)-5-phenyl-2H-tetrazol-3-ium) |

TABLE 1-continued

Exemplary Compounds of Formula (I)

| No. | Abbreviation | Chemical Structure and Name |
|-----|--------------|------------------------------|
| (4) | NDT | 3-(naphthalene-1-yl)-2,5-diphenyl-2H-tetrazol-3-ium |
| (5) | TBTB | Thiazolyl Blue Tetrazolium Bromide |
| (6) | INT | 2-(4-iodophenyl)-3-(4-nitrophenyl)-5-phenyl-2H-tetrazolium chloride |
| (7) | WST-1 | (2-(4-Iodophenyl)-3-(4-nitrophenyl)-5-(2,4-disulfophenyl)-2H-tetrazolium sodium salt |
| (8) | WST-3 | |

TABLE 1-continued

Exemplary Compounds of Formula (I)

| No. | Abbreviation | Chemical Structure and Name |
|---|---|---|
| (9) | WST-8 | 4-[3-(4-Iodophenyl)-2-(2,4-dinitrophenyl)-2H-5-tetrazolio]-1,3-benzene disulfonate 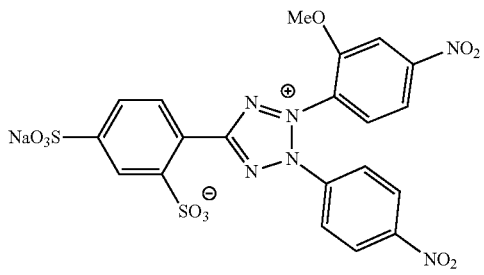 5-(2,4-disulfophenyl)-3-(2-methoxy-4-nitrophenyl)-2-(4-nitrophenyl)-2H-tetrazolium, inner salt, monosodium salt |

In some embodiments, the compound of Formula (I) is INT.

In some embodiments, the metabolic probe that is introduced during the metabolic probe assay is water insoluble. In further embodiments, the metabolic probe does not require the addition of an intermediate electron carrier in order for the molecule to be reduced efficiently by microorganisms.

In some embodiments, the metabolic probe that is introduced during the metabolic probe assay is 7-hydroxy-10-oxidophenoxazin-10-ium-3-one (resazurin). In some embodiments, the methods described herein use the commercially-available alamarBlue indicator dye (ThermoFisher Scientific, Waltham, MA) as the metabolic probe that comprises resazurin. Resazurin can undergo a reduction reaction in metabolically active cells, where the resazurin is converted to resorufin, a fluorescent molecule, via reduction reactions of metabolically active cells. The fluorescence emission produced by resorufin can be measured by a plate reader, a fluorescence spectrophotometer, and/or a UV-Vis spectrophotometer. In some cases where resazurin is used, excitation filters can be used to excite the sample with light at a wavelength of about 560 nm and emission filters can be used to detect light emitted from the sample at about 590 nm (e.g., after reduction to resorufin). In some embodiments, different assays utilize fluorescent probes with different emission wavelengths to avoid any interference in detection of the probes' fluorescent signals. For example, a metabolic probe assay and a surface binding probe assay can use florescence probes with different emission wavelengths, which allows for an accurate detection of their signals. An example of such combination of fluorescent probes is resazurin (which converts to resorufin) and europium cryptate.

In some embodiments, the metabolic probe is not enzymatically hydrolyzable by the microorganism. Introducing enzymatically hydrolyzable probes can be problematic for a metabolic assay because different microorganisms can have different enzymes. Examples of probes that are enzymatically hydrolyzable by the microorganism include a mixture of 4-methylumbelliferyl phosphate and 4-methylumbelliferyl fatty acid ester such as the hexanoate, octanoate or nonanoate, or other fatty acid ester for example within the chain length range C6-C16; a mixture of 4-methylumbelliferyl ester, e.g., phosphate, and a 7(N)-aminoacyl-4-methyl-7-amino coumarin, e.g., 7(N)-alanyl-4-methyl-7-amino-coumarin, the corresponding leucine derivative instead of the alanine derivative; 4-methylumbelliferyl nonanoate (MUN); 4-methylumbelliferyl phosphate (MUP); or 4-methyl-7-amino-coumarin-7-N-alanyl peptide; or corresponding fluorogenic derivatives of other coumarins.

Non-limiting examples of enzymatic biochemical probes that can be introduced during the enzymatic biochemical probe assay can include synthetic enzyme substrates containing coumarin derivatives of 4-methylumbelliferone or 7-amino-4-methyl coumarin; synthetic enzyme substrates containing esters of o-nitrophenol, p-nitrophenol, indoxyl, 5-bromo-4-chloro-3-indolyl, or 4-methylumbelliferone; aryl peptide derivatives of p-nitroaniline and 7-amino-4-methyl-coumarin. For example, derivatives of the following enzymes may be utilized: β-D-glucuronidase (substrates including but not limited to phenolphthalein-mono-β-D-glucuronide, p-nitrophenol-β-D-glucuronide, 5-bromo-4-chloro-3-indolyl-β-D-glucuronide, 4-methylumbelliferyl-β-D-glucuronide); β-D-galactosidase (substrates including but not limited to o-nitrophenyl-β-D-galactopyranoside, p-nitrophenyl-β-D-galactopyranoside, 6-bromo-2-naphthyl-β-D-galactopyranoside, 4-methylumbelliferyl-β-D-galactopyranoside, 5-bromo-4-chloro-3-indolyl-β-D-galactopyranoside); 6-phospho-β-D-galactoside 6-phosphogalactohydrolase (substrates including but not limited to o¬-nitrophenol-β-D-galactopyranoside-6-phosphate, o-nitrophenol-β-D-galactopyranoside); α-D-galactosidase (substrates including but not limited to 4-methylumbelliferyl-α-D-galactoside); β-D-glucosidase (substrates including but not limited to 4-methylumbelliferyl-β-D-glucoside); α-amylase (substrates including but not limited to p-nitrophenol derivates of penta-, hexa-, and hepta-maltose); neuraminidase (substrates including but not limited to o-nitrophenol and 4-methylumbelliferyl derivatives of β-D-galactosamine, β-D-glucosamine, 2-D-N-acetylneuraminic acid, β-D-N',N'-diacetylchitobiose); esterases (substrates including but not limited to 4-methylumbelliferyl-butyrate); DNAses (substrates including but not limited to 5-bromo-4-chloro-3-indolyl-thymidine-3-phosphate, thymidine-5-monophosphate-p-nitrophenol ester, phosphate ester of 5-bromo-4-chloro-3-indole); phosphates (substrates including but not limited to derivates of phenolphthalein, phenol, α- or β-naphthol, 5-bromo-4-chloro-3-indoxyl, p-nitrophenol, 4-methylumbelliferyl); pyroglutamyl aminopeptidase (substrates including but not limited to L-pyrrolidonyl-β-naphthylamide, L-pyroglutamyl-p-nitroanilide, L-pyroglutamyl-7-amido-4-methylcoumarin); L-alanine aminopeptidase (substrates including but not limited to p-nitroanilide-L-alanine); endopeptidase (substrates including but not limited to nitroanilide derivatives); or coagulase (substrates including but not limited to chromozym TH, D-Phe-Pro-Arg-β-naphthylamide HCl).

In some embodiments, changes in pH caused by specific enzymatic active, such as that caused by ureases, are detected.

Non-limiting examples of biochemical probes that can be introduced during the biochemical probe assay can include fluorescent glucose analogs including but not limited to 2-(N-(7-Nitrobenz-2-oxa-1,3-diazol-4-yl)Amino)-2-Deoxyglucose; fluorescent antibiotics, such as fluorescent polymyxin B analogs (including but not limited to BODIPY®, Oregon Green®, and dansyl derivatives), fluorescent penicillin analogs (including but not limited to BOCILLIN™ FL and BOCILLIN™ 650/665), or fluorescent vancomycin analogs (including, but not limited to, BODIPY®).

Non-limiting examples of nucleic acid probes that can be introduced during the nucleic acid probe assay can include acridine orange, 4,6-diamino-2-phenylindole, Hoechst 33258, ethidium bromide, ethidium homodimer, ethidium monoazide, hexidium iodide, mithramycin, propidium iodide, SYTOX® family of dyes, SYTO® family of dyes, TOTO® family of dyes (including POPO™, BOBO™, YOYO®, JOJO™, POPO™, LOLO™), TO-PRO® family of dyes (including YO-PRO®), or 7-aminoactinomycin D.

In some embodiments, these probes may be used directly or after cell lysis.

When used prior to cell lysis, nucleic acid probes that cannot effectively penetrate intact cell membranes may give a decreasing signal for increasing cell growth. Assays that give inverse signals can then be compared with assays that give increasing signals for increasing growth, such as metabolic (redox) probes, biochemical probes, etc.

Non-limiting examples of RNA probes that can be introduced during an RNA probe assay can include SYTO® RNASelect™ family of dyes.

Non-limiting examples of protein probes that can be introduced during a protein probe assay can include 8-anilino-1-naphthalene sulfonic acid or FUN® 1 cell stain.

Any optical device (e.g., microscope, microplate reader) with a number of varying features can detect a signal that is emitted according to methods described herein. For instance: broad spectrum lamp (e.g., xenon), narrow spectrum lamps, laser, LED, multi-photon, confocal or total-internal reflection illumination can be used for excitation. Cameras (single or multiple), single or arrays (1D or 2D) of photodiodes, avalanche photodiodes, CMOS or CCD sensors, solid-state photomultipliers (e.g. silicon photomultipliers), and/or Photomultiplier tube (single or multiple) with either filter-based or grating-based spectral resolution (a spectrally resolved emission wavelengths) are possible on the detection side.

In some embodiments, the methods described herein use an optical system that includes an optical excitation source (e.g., xenon lamp, light emitting diode (LED)), a set of optical filters (e.g., discrete filters, monochromators) with desired characteristics (e.g., band-pass, band-stop, central wavelength, full width half max (FWHM)), and an optical detector (e.g., photomultiplier tube). The optical systems can also include data acquisition and processing electronics used to collect and process data. In some cases, the optical system can include one or more components, such as fiber optics and collection optics, nested in, or otherwise disposed within or on, a robotic arm used to move cartridges throughout the system. Such a configuration can help achieve faster sample processing and results readout. These optical systems can carry a signal from cartridges to the detector and data processing electronics.

In some embodiments, the metabolic probe assay is used by itself to determine a MIC or a QSR for an antimicrobial.

Certain embodiments include separation steps between the metabolic probe assay and the surface-binding probe assay. Potential separation techniques can include, but are not limited to, filtering (e.g., via a filter having pores smaller than or equal to 0.45 microns, or smaller than or equal to 0.2 microns), centrifugation (e.g., with a g-force >500×g), electrophoresis, dielectrophoresis, and magnetic capture. These techniques can be employed to separate probes from one assay that are associated with microorganisms, which are stuck in a filter, pelleted in a centrifuge, and/or separated electrophoretically and/or magnetically, from those free in solution. Free probes pass through a filter ("filtrate"), remain in solution after centrifugation or magnetic separation ("supernatant"), and/or run separately electrophoretically. Centrifugation can be standard, density gradient, or differential centrifugation. Magnetic separation can require the addition of magnetic particles specifically targeted to associate with or bind to microorganisms. These can be added prior to or concurrently with probe addition.

In order to maximize separation efficiency, i.e., minimize the number of free probes from an assay that are remaining, a washing step can be performed. These can be discrete, as in the cases of centrifugation or magnetic capture and/or continuous, as in the cases of filtering, magnetic capture, or electrophoresis.

A wash can be performed before surface-binding probes from the surface-binding probe assay are added to the microorganisms. These washes can, for example, remove interfering species present in the liquid in which the microorganisms were suspended during incubation. In some embodiments, no wash is performed.

Certain embodiments of the methods described herein include an addition of a detergent solution comprising ethylenediaminetetraacetic acid and/or cetyl trimethylammonium bromide (CTAB). In some embodiments, detergent solutions comprise one or more of Tweens, Tritons, CTAB, Spans, Brijs, tetraammonium compounds, cationic polymers, pluronics, sulfates, CPC, sulfonates, BAC, phosphates, BZT, carboxylates, DODAB, docusate, fatty/high carbon alcohols, CHAPS, phospholipids, and/or glucosides.

The surface-binding probe assay can introduce a surface-binding probe that comprises a coordination complex of a lanthanide with diethylenetriaminetraacetic acid or a cryptate ligand. In certain embodiments, the surface-binding probe assay includes an amplifier such as a europium, strontium, terbium, samarium, and dysprosium, or a combination thereof. In some embodiments, the amplifier is a europium signaling agent comprising:

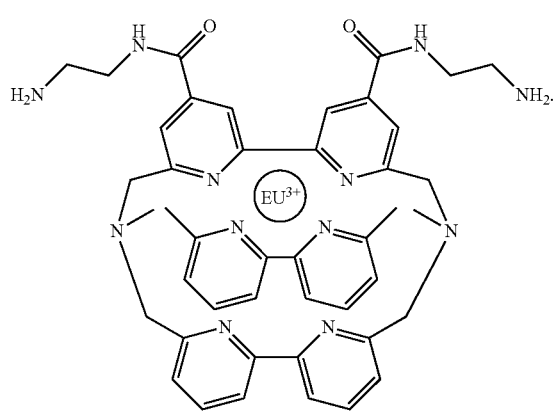

In the methods described herein, a surface can be an external surface of cell wall, cell envelope, plasma membrane, or cell capsule; internal surface of cell wall, cell envelope, plasma membrane, or cell capsule; or within a cell wall, cell envelope, plasma membrane, or cell capsule. The surface can include structures of the cell projecting extracellularly, including but not limited to cilium, pilus, and flagellum. The surface can include an organelle. The surface can include transmembrane proteins, cell-wall proteins, extracellular proteins, intracellular proteins, extracellular-associated polysaccharides, intracellular-associated polysaccharides, extracellular lipids, intracellular lipids, membrane lipids, cell-wall lipids, proteins, polysaccharides, and/or lipids integral to or associated with a cell envelop. The surface can include a nucleic acid.

The surface can include a biomolecule to which the signaling agent binds or associates. Non-limiting examples of biomolecules can include peptidoglycans, mureins, mannoproteins, porins, beta-glucans, chitin, glycoproteins, polysaccharides, lipopolysaccharides, lipooligosaccharides, lipoproteins, endotoxins, lipoteichoic acids, teichoic acids, lipid A, carbohydrate binding domains, efflux pumps, other cell-wall and/or cell-membrane associated proteins, other anionic phospholipids, and a combination thereof.

Signal development of the surface-binding probe assay can require the addition of a development solution. For signaling agents comprising catalysts, the development solution can comprise a signal precursor that can be converted to an optically and/or electrically active signaling molecule. At a specified time after addition of the development solution, a colorimetric and/or electrochemical signal can be measured. Such signals can include, but are not limited to, absorbance, fluorescence, time-resolved fluorescence, chemiluminescence, electrochemiluminescence, amperometric, voltammetric, impedance, and/or impedance spectroscopy. The data can then be compared to determine ASTs and MICs, similar to conventional AST protocols.

In some embodiments, in cases where lanthanide-based amplifiers are used, time-resolved fluorescence (TRF) or time-gated luminescence (TGL) is used. In certain embodiments, in cases where Europium (e.g., europium cryptate) is used, excitation filters are used to excite the sample with light at a wavelength of about 330 nm (e.g., with band of 80 nm) and emission filters are used to detect light emitted from the sample at about 615 nm (e.g., bandwidth of 10 nm). Excitation and detector are typically synchronized since TGL uses short pulses and delayed time windows for measurement due to long lifetime of lanthanide reporter molecules. For example, for Europium, a delay of 100-200 microsecond (s) can be used between extinction of the excitation light source and the start of measuring the light emitted by the sample. For example, a 200-600 s period of measuring the light emitted by the sample (i.e., integration window) can be used.

In some embodiments, determining signal levels includes measuring the signal levels associated with intact microorganisms. Alternately or additionally, determining signal levels includes measuring the signal levels not associated with intact microorganisms.

These processes can be performed directly from cultures, sub-cultures, positive blood cultures, samples. Treatments to concentrate microorganisms and/or remove potential interfering species can be performed prior to AST or prior to signaling agent addition.

MIC and/or QSR output data can be interpreted by a user directly from the data produced by the assays described herein. Alternatively, these data can be processed by an algorithm to yield MICs and/or QSRs. Reported MIC and/or QSR values can be derived from an assay described herein.

In some embodiments, the number of different assays that determine the MIC or QSR for an antimicrobial can be smaller than the number of assays performed. In some embodiments, the number of different assays that determine the MIC or QSR for an antimicrobial can be equal to the number of assays performed.

Checkpoint Assays

Checkpoint assays can be performed to ascertain microorganism growth. For example, in order to obtain accurate AST determinations, the assay can account for slow-growing strains of bacteria, and thus, the methods herein can provide for a checkpoint assay that occurs after an initial incubation period in order to ascertain whether sufficient microorganism growth has occurred. Growth, as in growth of microorganisms, can include a proliferation in number, an increase in length, an increase in volume, and/or an increase in nucleic acid and/or protein content of the microorganisms.

Although various endpoint measurements, such as ATP, DNA, RNA and surface-binding measurements, have previously been shown to be applicable to AST determinations, these assays have failed to date commercially due to their inability to account for slow-growing strains of microorganisms, such as the vancomycin-intermediate *Staphylococcus aureus* that can have significantly slower growth kinetics than other *S. aureus* strains, including methicillin-resistant and methicillin-susceptible strains.

Conventional AST methods can be performed on automated instruments that utilize a broth microdilution procedure in a microplate, where a growth indicator is included in the broth during inoculation and incubation in order to determine AST results by measuring indicator signals with respect to time. It was found, however, that these growth indicators, such as resazurin, can, in fact, be harmful to the microorganisms when they are added during the incubation period.

Although some growth indicators can suppress microbial growth, they can serve as a proxy for uninhibited growth through their incorporation in a growth threshold checkpoint well during microbial incubation. In order to address the slow-growing bacteria limitation, a checkpoint assay using a growth indicator can be first performed to measure that sufficient microorganism growth has reached a threshold, and then a final measurement of relative microorganism concentrations can be performed in separate wells to determine AST results (e.g. MIC or QSR). If the checkpoint assay shows that the microorganism growth has failed to reach the threshold, the microplate can be allowed to incubate for a further period of time and does not commence to the final measurement of relative microorganism concentrations until the growth threshold has been reached. In some embodiments, the additional incubation time period is performed between 1 and 20 hours, between 2 and 20 hours, between 3 and 20 hours, between 4 and 20 hours, between 5 and 20 hours, between 6 and 20 hours, between 8 and 20 hours, between 9 and 20 hours, between 10 and 20 hours, between 11 and 20 hours, between 12 and 20 hours, between 13 and 20 hours, between 14 and 20 hours, between 15 and 20 hours, between 16 and 20 hours, between 17 and 20 hours, between 18 and 20 hours, or between 19 and 20 hours. In some embodiments, the incubation period is between 2 and 19 hours, or between 3 and 18 hours, between 4 and 16 hours, between 3 and 14 hours, 3 and 12 hours or every possible time intervals in between.

In some embodiments, the threshold value is a ratio between a positive control and a background control. In some embodiments, the positive control comprises a suspension of microorganisms and a growth indicator incubated without an antimicrobial. In some embodiments, the background control comprises a medium and a growth indicator incubated without microorganisms. In some embodiments, a signal to noise ratio is measured by determining a ratio of a growth indicator signal such as alamar blue signal in an inoculated versus an uninoculated well. In certain embodiments, the ratio of the positive control to the background control is 1.1, 1.2, 1.3, 1.4, 1.5, 1.6, 1.7, 1.8, 1.9, 2.0, 2.1, 2.2, 2.3, 2.4, 2.5, or greater. In some embodiments, the signal to noise ratio is measured by determining the signal from a surface binding agent in an inoculated versus uninoculated well.

In some embodiments, the wells of the microplate used for these checkpoint assays do not comprise antimicrobials, nor are they utilized for the final measurements to determine an antimicrobial's efficacy. In certain embodiments, the checkpoint assay is performed in a chamber without an antimicrobial. In some embodiments, the checkpoint assay is performed in a chamber without one or more microorganisms. In some embodiments, the checkpoint assay is performed in a chamber with one or more antimicrobials of known efficacy against the microorganism.

When the threshold checkpoint assays indicate sufficient growth to initiate the AST growth assay, a plurality of different assays can be performed. AST growth assays, as previously discussed, can be utilized, such as assays for ATP, such as BacTiter-Glo®, RealTime-Glo™, Caspase-Glo®; DNA stains, such as ethidium bromide, propidium iodide, SYTOX green, phenanthridines, acridines, indoles, imidazoles, and cyanine, including TOTO, TO-PRO, SYTO; and binding assays, such as enzyme-linked immunosorbent assays, antibody assays, lectin-based assays, polymyxin B-based assays, and chemical probe-based assays.

In some embodiments, the checkpoint assay comprises nucleic acid amplification or nucleic acid sequencing. In some embodiments, the checkpoint assay comprises microscopy or mass spectrometry. In some embodiments, the checkpoint assay comprises measuring microorganism mass.

Growth Indicators

As described above, a growth indicator can be used in the checkpoint assay to ascertain sufficient microorganism growth before performing an AST growth assay. As shown below, various growth indicators can be utilized.

In some embodiments, the growth indicator is optically or electrically active during the checkpoint assay. Further, in some embodiments, the optical signal of the growth indicator comprises fluorescence, time-resolved fluorescence, absorbance or luminescence. The electrical signal of the growth indicator can be voltammetic or potentiometric.

In certain embodiments, the growth indicator undergoes a chemical or biochemical reaction during the checkpoint assay. In some embodiments, the growth indicator is a chemical or biochemical group capable of binding a microorganism cell membrane, cell wall, cell envelope, protein, saccharide, polysaccharide, lipid, organelle, or nucleic acid. Further still, the growth indicator can be responsive to pH during the checkpoint assay.

In some embodiments, the growth indicator described herein comprises 7-hydroxy-10-oxidophenoxazin-10-ium-3-one (resazurin), 3-(4,5-dimethylthiazol-2-yl)-2,5-diphenyltetrazolium bromide (MTT), 3-(4,5-dimethylthiazol-2-yl)-5-(3-carboxymethoxyphenyl)-2-(4-sulfophenyl)-2H-tetrazolium (MTS), 3,3'-(3,3'-Dimethoxy-4,4'-biphenylene)bis[2,5-bis(p-nitrophenyl)-2H-tetrazolium chloride] (TNBT), 2,3-bis-(2-methoxy-4-nitro-5-sulfophenyl)-2H-tetrazolium-5-carboxanilide (XTT), water-soluble tetrazolium salts (WSTs), (2-(4-Iodophenyl)-3-(4-nitrophenyl)-5-(2,4-disulfophenyl)-2H-tetrazolium sodium salt (WST-1), 4-[3-(4-Iodophenyl)-2-(2,4-dinitrophenyl)-2H-5-tetrazolio]-1,3-benzene disulfonate (WST-3), 2,2'-Dibenzothiazolyl-5,5'-bis[4-di(2-sulfoethyl)carbamoylphenyl]-3,3'-(3,3'-dimethoxy 4,4'-biphenylene)ditetrazolium, disodium salt (WST-5), 5-(2,4-disulfophenyl)-3-(2-methoxy-4-nitrophenyl)-2-(4-nitrophenyl)-2H-tetrazolium, inner salt, monosodium salt (WST-8), 2,3,5-triphenyl-tetrazolium chloride (TTC), 5-cyano-2,3-di(p-tolyl)tetrazolium chloride (CTC), 3,3'(3,3'-dimethoxy-[1,1'-biphenyl]-4,4'-diyl)bis(2-(4-nitrophenyl)-5-phenyl-2H-tetrazol-3-ium)(DBNPT), 3-(naphthalen-1-yl)-2,5-diphenyl-2H-tetrazol-3-ium (NDT), Thiazolyl Blue Tetrazolium Bromide (TBTB), 2-(4-Iodophenyl)-3-(4-nitrophenyl)-5-phenyl-2H-tetrazolium chloride (INT), phenazine methyl sulfate (PMS), phenazine ethyl sulfate (PES), glycylphenylalanyl-aminofluorocoumarin (GF-AFC), 2,2'-bis(4-Nitrophenyl)-5,5'-diphenyl-3,3'-(3,3'-dimethoxy-4,4'-diphenylene)ditetrazolium chloride (NBT), 2,5-Diphenyl-3-(1-naphthyl)tetrazolium chloride (TV), 3,3'-(3,3'-Dimethoxy[1,1'-biphenyl]-4,4'-diyl)-bis(2,5-diphenyl-2H-tetrazolium) dichloride (BTC), 5-Cyano-2,3-bis(4-methylphenyl)-2H-tetrazolium chloride (CTC), 2,3-Bis(2-methoxy-4-nitro-5-sulfophenyl)-2H-tetrazolium-5-carboxanilide inner salt (XTT), RealTime-Glo™, Caspase-Glo®, acetoxymethyl ester of BATDA, ferrocene, dodecylresazurin; dihydrorhodamine 123; dihydrofluorescein; 6-carboxy-2',7'-dichlorodihydro fluorescein diacetate and its acetoxymethyl ester; 2',7'-dichlorodihydrofluorescein diacetate; 5-carboxy-2',7'-dichlorodihydrofluorescein diacetate and its acetoxymethyl ester; chloromethyl-2',7'-dichlorodihydrofluorescein diacetate acetyl ester; dihydrocalcein AM; dihydroethidium; luminol; or 2,3,4,5,6-pentafuorotetramethyldihydroros amine.

In some embodiments, the growth indicator has a structure according to Formula (I),

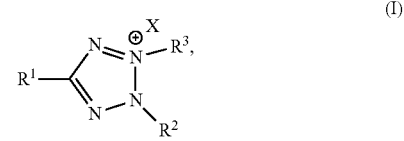

wherein

R¹ is independently CN, optionally substituted $C_6$-$C_{10}$ aryl, or optionally substituted 5- to 10-membered heteroaryl;

R² is independently optionally substituted $C_6$-$C_{10}$ aryl or optionally substituted 5- to 10-membered heteroaryl;

R³ is independently optionally substituted $C_6$-$C_{10}$ aryl, optionally substituted 5- to 10-membered heteroaryl, or Substructure A;

Substructure A is

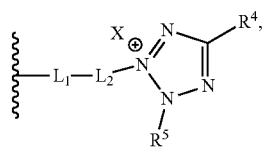

wherein $L_1$ is independently optionally substituted $C_6$-$C_{10}$ aryl or optionally substituted 5- to 10-membered heteroaryl;

$L_2$ is independently a covalent bond, optionally substituted $C_6$-$C_{10}$ aryl, or optionally substituted 5- to 10-membered heteroaryl;

R⁴ is independently CN, optionally substituted $C_6$-$C_{10}$ aryl, or optionally substituted 5- to 10-membered heteroaryl;

R⁵ is independently optionally substituted $C_6$-$C_{10}$ aryl or optionally substituted 5- to 10-membered heteroaryl;

each X is independently absent or a monovalent anion.

In some embodiments, R¹ is independently CN or optionally substituted $C_6$-$C_{10}$ aryl (e.g., phenyl substituted by 0, 1, 2, 3, 4, or 5 substituent groups). In some embodiments, R¹ is independently CN. In some embodiments, R¹ is independently unsubstituted phenyl or unsubstituted naphthyl. In some embodiments, R¹ is independently substituted $C_6$-$C_{10}$ aryl (e.g., phenyl substituted by 1, 2, 3, 4, or 5 substituent groups). In some embodiments, R¹ is independently a $C_6$-$C_{10}$ aryl (e.g., phenyl) having 1, 2, 3, 4, or 5 substituent groups independently selected from: $C_{1-6}$ alkyl (e.g., methyl, ethyl, n-propyl, or isopropyl); $C_{1-6}$ alkoxy (e.g., methoxy, ethoxy, n-propyloxy, or isopropyloxy); halogen (e.g., F, Cl, Br, or I); —CN; nitro; and sulfonic acid or an ionized form thereof (e.g., —SO₃H or —SO₃Na). In some embodiments, R¹ is independently a $C_6$-$C_{10}$ aryl (e.g., phenyl) having 1, 2, 3, 4, or 5 substituent groups independently selected from: $C_{1-6}$ alkyl (e.g., methyl, ethyl, n-propyl, or isopropyl); $C_{1-6}$ alkoxy (e.g., methoxy, ethoxy, n-propyloxy, or isopropyloxy); halogen (e.g., F, Cl, Br, or I); —CN; and nitro.

In some embodiments, R² is independently optionally substituted $C_6$-$C_{10}$ aryl (e.g., phenyl substituted by 0, 1, 2, 3, 4, or 5 substituent groups). In some embodiments, R² is independently unsubstituted phenyl or unsubstituted naphthyl. In some embodiments, R² is independently substituted $C_6$-$C_{10}$ aryl (e.g., phenyl substituted by 1, 2, 3, 4, or 5 substituent groups). In some embodiments, R² is independently a $C_6$-$C_{10}$ aryl (e.g., phenyl) having 1, 2, 3, 4, or 5 substituent groups independently selected from: $C_{1-6}$ alkyl (e.g., methyl, ethyl, n-propyl, or isopropyl); $C_{1-6}$ alkoxy (e.g., methoxy, ethoxy, n-propyloxy, or isopropyloxy); halogen (e.g., F, Cl, Br, or I); —CN; and nitro.

In some embodiments, R³ is independently optionally substituted $C_6$-$C_{10}$ aryl (e.g., phenyl substituted by 0, 1, 2, 3, 4, or 5 substituent groups). In some embodiments, R³ is independently unsubstituted phenyl or unsubstituted naphthyl. In some embodiments, R³ is independently substituted $C_6$-$C_{10}$ aryl (e.g., phenyl substituted by 1, 2, 3, 4, or 5 substituent groups). In some embodiments, R³ is independently a $C_6$-$C_{10}$ aryl (e.g., phenyl) having 1, 2, 3, 4, or 5 substituent groups independently selected from: $C_{1-6}$ alkyl (e.g., methyl, ethyl, n-propyl, or isopropyl); $C_{1-6}$ alkoxy (e.g., methoxy, ethoxy, n-propyloxy, or isopropyloxy); halogen (e.g., F, Cl, Br, or I); —CN; and nitro.

In some embodiments, X is a monovalent anion (e.g., Cl⁻ or Br⁻). In further embodiments, R¹ is independently CN or optionally substituted $C_6$-$C_{10}$ aryl (e.g., phenyl substituted by 1, 2, 3, 4, or 5 substituent groups selected from: $C_{1-6}$ alkyl (e.g., methyl, ethyl, n-propyl, or isopropyl); $C_{1-6}$ alkoxy (e.g., methoxy, ethoxy, n-propyloxy, or isopropyloxy); halogen (e.g., F, Cl, Br, or I); —CN; and nitro).

In some embodiments, X is absent. In further embodiments, R¹ is independently substituted $C_6$-$C_{10}$ aryl comprising a substituent that is an ionized sulfonic acid group.

In some embodiments, R³ is Substructure A, and the compound has a structure according to Formula (II):

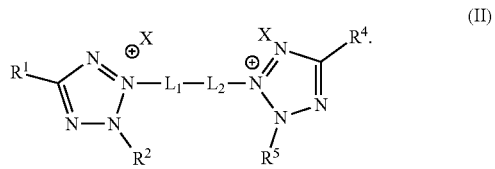

In embodiments, $L_1$ is optionally substituted $C_6$-$C_{10}$ arylene, and $L_2$ is a covalent bond.

In embodiments, each of $L_1$ and $L_2$ is independently optionally substituted $C_6$-$C_{10}$ arylene. In embodiments, each of $L_1$ and $L_2$ is independently optionally substituted phenylene. In embodiments, each of $L_1$ and $L_2$ is unsubstituted phenylene. In embodiments, each of $L_1$ and $L_2$ is independently substituted phenylene having 1, 2, 3, or 4 substituent groups independently selected from: $C_{1-6}$ alkyl (e.g., methyl, ethyl, n-propyl, or isopropyl); $C_{1-6}$ alkoxy (e.g., methoxy, ethoxy, n-propyloxy, or isopropyloxy); halogen (e.g., F, Cl, Br, or I); —CN; and nitro. In embodiments, each of $L_1$ and $L_2$ is independently substituted phenylene comprising a $C_{1-6}$ alkoxy (e.g., methoxy, ethoxy, n-propyloxy, or isopropyloxy).

In some embodiments, R⁴ is independently CN or optionally substituted $C_6$-$C_{10}$ aryl (e.g., phenyl substituted by 0, 1, 2, 3, 4, or 5 substituent groups). In some embodiments, R⁴ is independently CN. In some embodiments, R⁴ is independently unsubstituted phenyl or unsubstituted naphthyl. In some embodiments, R⁴ is independently substituted $C_6$-$C_{10}$ aryl (e.g., phenyl substituted by 1, 2, 3, 4, or 5 substituent groups). In some embodiments, R⁴ is independently a $C_6$-$C_{10}$ aryl (e.g., phenyl) having 1, 2, 3, 4, or 5 substituent groups independently selected from: $C_{1-6}$ alkyl (e.g., methyl, ethyl, n-propyl, or isopropyl); $C_{1-6}$ alkoxy (e.g., methoxy, ethoxy, n-propyloxy, or isopropyloxy); halogen (e.g., F, Cl, Br, or I); —CN; nitro; and sulfonic acid or an ionized form thereof (e.g., —SO₃H or —SO₃Na). In some embodiments, R⁴ is independently a $C_6$-$C_{10}$ aryl (e.g., phenyl) having 1, 2, 3, 4, or 5 substituent groups independently selected from: $C_{1-6}$ alkyl (e.g., methyl, ethyl, n-propyl, or isopropyl); $C_{1-6}$ alkoxy (e.g., methoxy, ethoxy, n-propyloxy, or isopropyloxy); halogen (e.g., F, Cl, Br, or I); —CN; and nitro.

In some embodiments, R¹ and R⁴ are the same group. In some embodiments, each of R¹ and R⁴ is a $C_6$-$C_{10}$ aryl (e.g., phenyl) having 0, 1, 2, 3, 4, or 5 substituent groups independently selected from: $C_{1-6}$ alkyl (e.g., methyl, ethyl, n-propyl, or isopropyl); $C_{1-6}$ alkoxy (e.g., methoxy, ethoxy, n-propyloxy, or isopropyloxy); halogen (e.g., F, Cl, Br, or I); —CN; nitro; and sulfonic acid or an ionized form thereof (e.g., —$SO_3H$ or —$SO_3Na$). In some embodiments, each of $R^1$ and $R^4$ is a $C_6$-$C_{10}$ aryl (e.g., phenyl) having 0, 1, 2, 3, 4, or 5 substituent groups independently selected from: $C_{1-6}$ alkyl (e.g., methyl, ethyl, n-propyl, or isopropyl); $C_{1-6}$ alkoxy (e.g., methoxy, ethoxy, n-propyloxy, or isopropyloxy); halogen (e.g., F, Cl, Br, or I); —CN; and nitro.

In some embodiments, $R^5$ is independently optionally substituted $C_6$-$C_{10}$ aryl (e.g., phenyl substituted by 0, 1, 2, 3, 4, or 5 substituent groups). In some embodiments, $R^5$ is independently unsubstituted phenyl or unsubstituted naphthyl. In some embodiments, $R^5$ is independently substituted $C_6$-$C_{10}$ aryl (e.g., phenyl substituted by 1, 2, 3, 4, or 5 substituent groups). In some embodiments, $R^5$ is independently a $C_6$-$C_{10}$ aryl (e.g., phenyl) having 1, 2, 3, 4, or 5 substituent groups independently selected from: $C_{1-6}$ alkyl (e.g., methyl, ethyl, n-propyl, or isopropyl); $C_{1-6}$ alkoxy (e.g., methoxy, ethoxy, n-propyloxy, or isopropyloxy); halogen (e.g., F, Cl, Br, or I); —CN; and nitro.

In some embodiments, $R^2$ and $R^5$ are the same group. In some embodiments, each of $R^2$ and $R^5$ is a $C_6$-$C_{10}$ aryl (e.g., phenyl) having 0, 1, 2, 3, 4, or 5 substituent groups independently selected from: $C_{1-6}$ alkyl (e.g., methyl, ethyl, n-propyl, or isopropyl); $C_{1-6}$ alkoxy (e.g., methoxy, ethoxy, n-propyloxy, or isopropyloxy); halogen (e.g., F, Cl, Br, or I); —CN; nitro; and sulfonic acid or an ionized form thereof (e.g., —$SO_3H$ or —$SO_3Na$). In some embodiments, each of $R^2$ and $R^5$ is a $C_6$-$C_{10}$ aryl (e.g., phenyl) having 0, 1, 2, 3, 4, or 5 substituent groups independently selected from: $C_{1-6}$ alkyl (e.g., methyl, ethyl, n-propyl, or isopropyl); $C_{1-6}$ alkoxy (e.g., methoxy, ethoxy, n-propyloxy, or isopropyloxy); halogen (e.g., F, Cl, Br, or I); —CN; and nitro.

In some embodiments, each X is a monovalent anion (e.g., each X is independently $Cl^-$ or $Br^-$). In further embodiments, each $R^1$ and $R^4$ is independently CN or optionally substituted $C_6$-$C_{10}$ aryl (e.g., phenyl substituted by 1, 2, 3, 4, or 5 substituent groups selected from: $C_{1-6}$ alkyl (e.g., methyl, ethyl, n-propyl, or isopropyl); $C_{1-6}$ alkoxy (e.g., methoxy, ethoxy, n-propyloxy, or isopropyloxy); halogen (e.g., F, Cl, Br, or I); —CN; and nitro). In some embodiments, $R^1$ and $R^4$ are the same group.

Exemplary compounds of Formula (I) are listed in Table 2.

TABLE 2

Exemplary Compounds of Formula (I)

| No. | Abbreviation | Chemical Structure and Name |
|---|---|---|
| (1) | TTC | 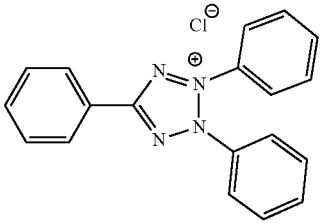 [SMILES: c1ccc(-c2nn(-c3ccccc3)[n+](-c3ccccc3)n2)cc1 ; [Cl-]]<br>2,3,5-triphenyl-tetrazolium chloride |
| (2) | CTC | 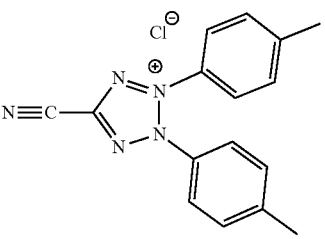 [SMILES: Cc1ccc(-n2nc(C#N)n[n+]2-c2ccc(C)cc2)cc1 ; [Cl-]]<br>5-cyano-2,3-di(p-tolyl)tetrazolium chloride |
| (3) | DBNPT | 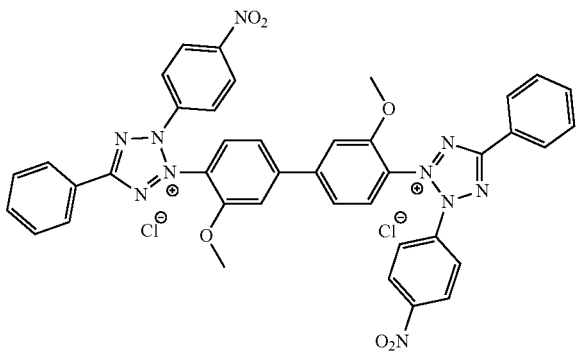 [SMILES: COc1cc(-c2ccc(-[n+]3nc(-c4ccccc4)nn3-c3ccc([N+](=O)[O-])cc3)c(OC)c2)ccc1-[n+]1nc(-c2ccccc2)nn1-c1ccc([N+](=O)[O-])cc1 ; [Cl-] ; [Cl-]]<br>3,3'-(3,3'-dimethoxy-[1,1'-biphenyl]-4,4'-diyl)bis(2-(4-nitrophenyl)-5-phenyl-2H-tetrazol-3-ium) |

TABLE 2-continued

Exemplary Compounds of Formula (I)

| No. | Abbreviation | Chemical Structure and Name |
|---|---|---|
| (4) | NDT | 3-(naphthalene-1-yl)-2,5-diphenyl-2H-tetrazol-3-ium |
| (5) | TBTB | Thiazolyl Blue Tetrazolium Bromide |
| (6) | INT | 2-(4-iodophenyl)-3-(4-nitrophenyl)-5-phenyl-2H-tetrazolium chloride |
| (7) | WST-1 | (2-(4-Iodophenyl)-3-(4-nitrophenyl)-5-(2,4-disulfophenyl)-2H-tetrazolium sodium salt |
| (8) | WST-3 | |

TABLE 2-continued

Exemplary Compounds of Formula (I)

| No. | Abbreviation | Chemical Structure and Name |
|---|---|---|
| (9) | WST-8 | 4-[3-(4-Iodophenyl)-2-(2,4-dinitrophenyl)-2H-5-tetrazolio]-1,3-benzene disulfonate 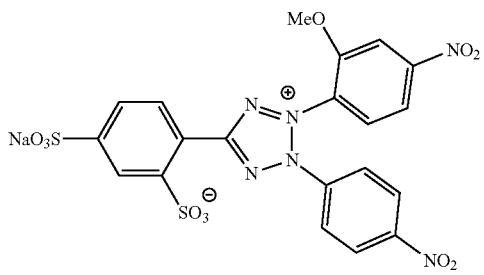 5-(2,4-disulfophenyl)-3-(2-methoxy-4-nitrophenyl)-2-(4-nitrophenyl)-2H-tetrazolium, inner salt, monosodium salt |

In some embodiments, the compound of Formula (I) is INT.

In some embodiments, suitable growth indicators are metabolic probes that are well known to those skilled in the art and are described in *The Molecular Probes® Handbook: A Guide to Fluorescent Probes and Labeling Technologies*, 11$^{th}$ Ed. (2010) (see, e.g., Chapter 15, "Assays for Cell Viability, Proliferation and Function") and Riss T L, Moravec R A, Niles A L, et al. Cell Viability Assays. 2013 May 1 [Updated 2016 Jul. 1]. In: Sittampalam G S, Coussens N P, Nelson H, et al., editors. Assay Guidance Manual [Internet]. Bethesda (Md.): Eli Lilly & Company and the National Center for Advancing Translational Sciences; 2004-. and U.S. Pat. No. 7,897,331, which are herein incorporated by reference in their entirety.

In some embodiments, the growth indicator is 7-hydroxy-10-oxidophenoxazin-10-ium-3-one (resazurin). In some embodiments, the methods described herein use the commercially-available alamarBlue® as the growth indicator that comprises resazurin. In some embodiments, resazurin undergoes a reduction reaction in metabolically active cells, where the resazurin is converted to resorufin, a fluorescent molecule. In some embodiments, the fluorescence emission produced by resorufin is measured by a plate reader, a fluorescence spectrophotometer, and/or a UV-Vis spectrophotometer. In some embodiments, the growth indicator is introduced to pre-determined checkpoint assay chambers during introduction of the suspension of microorganisms to the cartridge chambers or at the beginning of the incubation period.

A time gated luminescence (e.g., time resolved fluorescence) can be utilized to measure an optical signal from the growth indicator. In some cases, methods allow excitation of an amplifier molecule and detection of emitted light, which can be separated both temporally (e.g., detection can be delayed and occurs after excitation when all auto fluorescence has died out) and spectrally (e.g., wavelength of excitation can be more than 100 nm apart from emission which allows usage of less expensive band pass filters). In some embodiments, amplification is achieved by the addition of a substrate that is catalytically modified by the bound molecule and optical output can be measured. This optical signal can include absorbance signals, fluorescence signals, and/or chemiluminescence signals. In some embodiments, the signal includes electrochemiluminescence (ECL).

Cartridges

A cartridge can be a container that is capable of holding and allowing growth of a liquid suspension of microorganisms. Non-limiting examples of a cartridge can include a culture flask, a culture dish, a petri dish, a bioassay dish, a culture tube, a test tube, a microfuge tube, a bottle, a microchamber plate, a multi-chamber plate, a microtiter plate, a microplate. The cartridge can comprise one chamber. The cartridge can include a plurality of chambers, each chamber being a space capable of holding a liquid suspension in physical isolation from another space; an example of a chamber is a chamber in a multiwall plate. The cartridge can comprise 1, 2, 3, 4, 5, 6, 7, 8, 9, 10, 11, 12, 24, 48, 96, 192, 384, 1536, or more chambers, and any number of chambers in between. The bottom of the cartridge chamber can be flat, round, or V-shaped.

Antimicrobials present within a plurality of chambers on the cartridge can be suspended in a medium. In some embodiments, the antimicrobial is present in the form of antimicrobial film. In certain embodiments, the antimicrobial is in solid form. In some embodiments, the solid antimicrobial is lyophilized and/or dried. Certain embodiments provide for one or more antimicrobials present in one or more cartridge chambers as antimicrobial films, in solid form, lyophilized, or dried prior to introduction of a suspension of microorganisms.

An antimicrobial dilution series can be frozen, lyophilized, or prepared fresh prior to plate inoculation with microorganisms. In some cases, inoculation of cartridges can be performed either by hand or using an automated system. In some examples, such as in cases of fresh antimicrobial plates, an automated liquid handling system can be used to prepare the cartridge with antimicrobial dilution series. Inoculation processes can include any of various processes that can be known in the art.

As described herein, cartridges can be used to contain various combinations of fluids in order to carry out multiple testing sequences, such as a check point assay and a plurality of different growth assays. In some embodiments, a cartridge has a set of chambers used to facilitate the one or more checkpoint assays and a set of chambers used to facilitate the one or more growth assays. By way of example, a cartridge can include an array of chambers arranged in rows and columns. The cartridge can include a set of control chambers and a set of antimicrobial testing chambers. The set of control chambers can include two chambers and the set of testing chambers can include the remainder of chambers along the plate. In some embodiments, the set of control chambers includes at least two chambers, where one chamber is a growth chamber and another chamber is a no-growth chamber. In some embodiments, the growth chamber includes, or be inoculated to include, a combination of broth and microorganisms that can grow within the broth during an incubation period. In certain embodiments, antimicrobials are not added to the checkpoint assay chamber. Whereas, in some embodiments, the no-growth chamber can include, or be inoculated to include, broth without microorganisms. In some embodiments, antimicrobials are also not added to the no-growth chamber. Thus, during an incubation period, the no-growth chamber can serve as a baseline as compared to the growth chamber in which the microorganisms can grow.

In some embodiments, each cartridge contains a combination of antimicrobials and a defined two-fold dilution series of each antimicrobial. In addition, each cartridge can contain control chambers, such as a growth control chamber, a no growth (contamination) control chamber and a saline control chamber. The saline control chamber can represent FIT control approximately equal to the initial concentration of microorganism in inoculum. The cartridges can include multiple chambers (e.g., 96 chamber cartridge or 384 chamber cartridge) with a cover (e.g., a removable lid) and an identifier (e.g., a bar code) that uniquely defines antibiotic configuration and a unique code, which defines the plate and can be associated with a unique patient sample conforming to HIPAA.

The testing chambers can include any of various combinations of microorganism derived from biological samples and various types and concentrations of antimicrobials for which susceptibility can be analyzed. Rows of chambers can be dedicated to a particular antimicrobial and concentrations of that antimicrobial can vary between columns of the same row. For example, a cartridge can have a row of chambers containing penicillin where each chamber from left to right contains an increasing concentration of penicillin.

Of course, other examples are possible. For example, the different chambers and sets of chambers can be positioned at any of various locations along a cartridge. Additionally, the different sets of chambers (e.g., control chambers and testing chambers) can include greater or fewer individual chambers along the cartridge. Additionally, in some cases, not all chambers are used/occupied during testing.

Preheating Cartridges

Preheating a cartridge to 30-45° C. prior to an incubation period can be advantageous for promoting microorganism growth, which in turn can yield faster and/or more accurate antimicrobial susceptibility test (AST) determinations. Preheating can be useful in some cases since standard air convection incubators typically take 30 to 60 minutes to bring a test panel to a desired working temperature. Preheating can be particularly useful for use with the methods described herein for performing rapid AST since typical desired incubation times are below 8 hours and in most cases less than 7 hours, less than 6 hours, less than 5 hours, less than 4 hours, or less than 3 hours.

By maximizing the amount of time that microorganisms are incubated at temperatures between 30° C. and 45° C., 31-39° C., or 33-37° C., sufficient growth for achieving dynamic growth ranges, and thus more accurate AST determinations, can be realized. In automated AST testing in which broth microdilutions are used, increasing the speed with which solutions in each cartridge well reach temperatures promoting microorganism growth can shorten the duration of the AST assay.

In some embodiments, a single 96-well microplate (with a lid) reached growth-promoting temperatures after about 20 minutes of standard convection heating, and stacked 96-well microplates, which can help increase assay throughput, required a heating time of about 40 minutes to reach these temperatures.

Well-to-well uniformity of heating can also be an issue using standard incubators, specifically with stacked microplates. There can be a significant radial distribution of well temperatures which can be magnified for the central plates of a 4-plate stack.

The methods described herein can promote microorganism growth by preheating a cartridge comprising a suspension of microorganisms to a temperature from about 30° C. to about 45° C. before incubating the preheated cartridge. In some embodiments, the incubation of the microorganisms occurs within 10, 15, 20, 25, 30 or 60 minutes after preheating the cartridge. A larger dynamic growth range can be produced by these enhanced growth techniques described herein, which can result in better AST assay results.

In some embodiments, the cartridge is preheated to a temperature from about 27° C. to about 48° C.; about 30° C. to about 45° C., about 31° C. to about 39° C., or about 33° C. to about 37° C.

The cartridge that is preheated can comprise at least 96 chambers. The preheating of the cartridge can result in substantially uniform heating of the least 96 chambers.

In some embodiments, the cartridge is preheated for less than about 15 minutes, less than about 10 minutes, less than about 5 minutes, less than about 2 minutes, or less than about 1 minute. In certain embodiments, the cartridge is preheated for 1, 2, 3, 4, 5, 6, 7, 8, 9, 10, 11, 12, 13, 14, or 15 or 30 minutes.

Preheating of the cartridge can occur by radiative heating, conduction heating, or convection heating. In some embodiments, the radiative heating is infrared radiative heating. Alternatively, the cartridge can be preheated by conduction and convection heating, and at least one heating surface can perform the conduction and convection heating. In some embodiments, the cartridge is preheated by both radiative heating and conduction and convection heating. In certain embodiments, the cartridge is not preheated by convection heating alone. The cartridge can also be preheated by an addition to the cartridge of at least one fluid at a temperature of at least 25° C., a temperature of at least 30° C., or a temperature of at least 35° C.

In some embodiments, the cartridge is preheated prior to loading the cartridge into an automated platform for performing antimicrobial susceptibility testing.

The preheating of the cartridge can result in a variation of temperature across the cartridge less than 5%. Certain embodiments provide for substantially uniform heating of the chambers where a percent different of temperature between the highest-temperature chamber and the lowest-temperature chamber is less than 5%.

Cartridge Agitation

Solution mixing is well understood by those skilled in the art to promote microorganism growth rates in large growth solution volumes (e.g. >10 mL) by enhancing solution aeration. Broth microdilution AST assays are commonly performed in cartridges comprising wells with lateral dimensions <12 mm. In order to achieve proper solution mixing in wells with lateral dimensions <12 mm, the orbital shaking frequencies must be at least 500 revolutions per minute (rpm). However, these frequencies will inhibit microorganism growth in wells with lateral dimensions <12 mm due to high strain and shears on the microorganisms.

In certain embodiments, the methods provide for promoting microorganism growth by agitating the cartridge at a frequency or a radius insufficient to achieve solution mixing. Agitation, such as orbital or axial shaking, of the cartridges and microorganisms therein can be used during incubation to promote better oxygenation of microorganisms and uniform exposure to nutrients in growth media. Surprisingly, it was found that sub-mixing-inducing shaking frequencies and radii can enhance microorganism growth rates.

In some embodiments of the present method, the cartridge comprises at least 96 chambers and each of the chambers has a lateral dimension of less than 12 mm. The cartridge can be agitated by means of mechanical agitation, acoustic agitation, or magnetic agitation. Non-limiting examples of mechanical agitation can include shaking or rocking and/or use of stir bars, stir paddles, stir blades, and/or stir propellers or impellers. Mechanical agitation can be axis linear, orbital, or semi-orbital shaking.

Orbital shaking (e.g., circular, ellipsoid, etc.) can occur at a frequency of greater than 50 revolutions per minute, greater than 60 revolutions per minute, greater than 70 revolutions per minute, greater than 80 revolutions per minute, greater than 90 revolutions per minute, greater than 100 revolutions per minute, greater than 125 revolutions per minute, greater than 150 revolutions per minute, greater than 175 revolutions per minute, greater than 200 revolutions per minute, greater than 225 revolutions per minute, greater than 250 revolutions per minute, greater than 275 revolutions per minute, greater than 300 revolutions per minute, greater than 325 revolutions per minute, greater than 350 revolutions per minute, greater than 375 revolutions per minute, greater than 400 revolutions per minute, greater than 500 revolutions per minute, greater than 600 revolutions per minute, greater than 700 revolutions per minute, greater than 725 revolutions per minute, greater than 750 revolutions per minute, or greater than 775 revolutions per minute.

The orbital shaking radius can be greater than 1 mm, greater than 2 mm, greater than 3 mm, greater than 4 mm, greater than 5 mm, greater than 6 mm, greater than 7 mm, greater than 8 mm, greater than 9 mm, greater than 10 mm, greater than 11 mm, greater than 12 mm, greater than 13 mm, greater than 14 mm, greater than 15 mm, greater than 16 mm, greater than 17 mm, greater than 18 mm, greater than 19 mm, greater than 20 mm, greater than 21 mm, greater than 22 mm, greater than 23 mm, or greater than 24 mm. The radius can be 25 mm.

In some embodiments, axial linear shaking comprises 1, 2, 3, 4, 5, or 6-axis linear motions.

The speed and displacement of agitation can be adjusted for additional optimal performance. For example, cartridges having smaller well sizes (e.g., diameters), such as in 384-chamber cartridges, can benefit from agitation that is performed with higher frequency and smaller diameter orbit (in the case of orbital agitation) compared with larger wells such as in 96-chamber cartridges. This change in agitation can be useful to keep the liquid in the cartridge wells smoothly swirling within the well as the plate geometry changes. In some embodiments, conditions promoting microorganism growth include exposing the microorganisms to ambient air, anaerobic conditions, or up to 10% $CO_2$.

In some embodiments, agitating the cartridge at a frequency or a radius insufficient to achieve solution mixing results in a greater growth ratio between microorganism growth with agitation of the cartridge as compared to microorganism growth without agitation of the cartridge.

Microorganisms

An infection can include any infectious agent of a microbial origin, e.g., a bacterium, a fungal cell, an archaeon, and a protozoan. In some examples, the infectious agent is a bacterium, e.g., a gram-positive bacterium, a gram-negative bacterium, and an atypical bacterium. An antimicrobial resistant microorganism can be a microorganism that is resistant to an antimicrobial, i.e., anti-bacterial drugs, anti-fungal drugs, anti-archaea medications, and anti-protozoan drugs.

The microorganisms (e.g., a liquid suspension of microorganisms) can include one strain of microorganism. The microorganisms can include one species of microorganism. The microorganisms can include more than one strain of microorganism. The microorganisms can include one order of microorganism. The microorganisms can include one class of microorganism. The microorganisms can include one family of microorganism. The microorganisms can include one kingdom of microorganism.

The microorganisms (e.g., a liquid suspension of microorganisms) can include more than one strain of microorganism. The microorganisms can include more than one species of microorganism. The microorganisms can include more than one genus of microorganism. The microorganisms can include more than one order of microorganism. The microorganisms can include more than one class of microorganism. The microorganisms can include more than one family of microorganism. The microorganisms can include more than one kingdom of microorganism.

The microorganism can be a bacterium. Examples of bacteria include, but are not limited to, *Acetobacter aurantius, Acinetobacter bitumen, Acinetobacter* spp., *Actinomyces israelii, Actinomyces* spp., *Aerococcus* spp., *Agrobacterium radiobacter, Agrobacterium tumefaciens, Anaplasma, Anaplasma phagocytophilum, Azorhizobium caulinodans, Azotobacter vinelandii, Bacillus, Bacillus anthracis, Bacillus brevis, Bacillus cereus, Bacillus fusiformis, Bacillus licheniformis, Bacillus megaterium, Bacillus mycoides, Bacillus* spp., *Bacillus stearothermophilus, Bacillus subtilis, Bacillus Thuringiensis, Bacteroides, Bacteroides fragilis, Bacteroides gingivalis, Bacteroides melaninogenicus* (also known as *Prevotella melaninogenica*), *Bartonella, Bartonella henselae, Bartonella quintana, Bartonella* spp., *Bordetella, Bordetella bronchiseptica, Bordetella pertussis, Bordetella* spp., *Borrelia burgdorferi, Brucella, Brucella abortus, Brucella melitensis, Brucella* spp., *Brucella suis, Burkholderia, Burkholderia cepacia, Burkholderia mallei, Burkholderia pseudomallei, Calymmatobacterium granulomatis, Campylobacter, Campylobacter coli, Campylobacter fetus, Campylobacter jejuni, Campylobacter pylori, Campylobacter* spp., *Chlamydia, Chlamydia* spp., *Chlamydia trachomatis, Chlamydophila, Chlamydophila pneumoniae* (previously called *Chlamydia pneumoniae*), *Chlamydophila psittaci* (previously called *Chlamydia psittaci*), *Chlamydophila* spp., *Clostridium, Clostridium botulinum, Clostridium difficile, Clostridium perfringens* (previously called *Clostridium welchii*), *Clostridium* spp., *Clostridium tetani, Corynebacterium, Corynebacterium diphtheriae, Corynebacterium fusiforme, Corynebacterium* spp., *Coxiella burnetii, Ehrlichia chaffeensis, Ehrlichia* spp., *Enterobacter cloacae, Enterobacter* spp., *Enterococcus, Enterococcus avium, Enterococcus durans, Enterococcus faecalis, Enterococcus faecium, Enterococcus galllinarum, Enterococcus maloratus, Enterococcus* spp., *Escherichia coli, Francisella* spp., *Francisella tularensis, Fusobacterium nucleatum, Gardenerella* spp., *Gardnerella vaginalis, Haemophilus* spp., *Haemophilus, Haemophilus ducreyi, Haemophilus influenzae, Haemophilus parainfluenzae, Haemophilus pertussis, Haemophilus vaginalis, Helicobacter pylori, Helicobacter* spp., *Klebsiella pneumoniae, Klebsiella* spp., *Lactobacillus, Lactobacillus acidophilus, Lactobacillus bulgaricus, Lactobacillus casei, Lactobacillus* spp., *Lactococcus lactis, Legionella pneumophila, Legionella* spp., *Leptospira* spp., *Listeria monocytogenes, Listeria* spp., *Methanobacterium extroquens, Microbacterium multiforme, Micrococcus luteus, Moraxella catarrhalis, Mycobacterium, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegmatis, Mycobacterium* spp., *Mycobacterium tuberculosis, Mycoplasma, Mycoplasma fermentans, Mycoplasma genitalium, Mycoplasma hominis, Mycoplasma penetrans, Mycoplasma pneumoniae, Mycoplasma* spp., *Neisseria, Neisseria gonorrhoeae, Neisseria meningitidis, Neisseria* spp., *Nocardia* spp., *Pasteurella, Pasteurella multocida, Pasteurella* spp., *Pasteurella tularensis, Peptostreptococcus, Porphyromonas gingivalis, Prevotella melaninogenica* (previously called *Bacteroides melaninogenicus*), *Proteus* spp., *Pseudomonas aeruginosa, Pseudomonas* spp., *Rhizobium radiobacter, Rickettsia, Rickettsia prowazekii, Rickettsia psittaci, Rickettsia quintana, Rickettsia rickettsii, Rickettsia* spp., *Rickettsia trachomae, Rochalimaea, Rochalimaea henselae, Rochalimaea quintana, Rothia dentocariosa, Salmonella, Salmonella enteritidis, Salmonella* spp., *Salmonella typhi, Salmonella typhimurium, Serratia marcescens, Shigella dysenteriae, Shigella* spp., *Spirillum volutans, Staphylococcus, Staphylococcus aureus, Staphylococcus epidermidis, Staphylococcus* spp., *Stenotrophomonas maltophilia, Stenotrophomonas* spp., *Streptococcus, Streptococcus agalactiae, Streptococcus avium, Streptococcus bovis, Streptococcus cricetus, Streptococcus faceium, Streptococcus faecalis, Streptococcus ferus, Streptococcus gallinarum, Streptococcus lactis, Streptococcus mitior, Streptococcus mitis, Streptococcus mutans, Streptococcus oralis, Streptococcus pneumoniae, Streptococcus pyogenes, Streptococcus rattus, Streptococcus salivarius, Streptococcus sanguis, Streptococcus sobrinus, Streptococcus* spp., *Treponema, Treponema denticola, Treponema pallidum, Treponema* spp., *Ureaplasma* spp., *Vibrio, Vibrio cholerae, Vibrio comma, Vibrio parahaemolyticus, Vibrio* spp., *Vibrio vulnificus, Viridans streptococci, Wolbachia, Yersinia, Yersinia enterocolitica, Yersinia pestis, Yersinia pseudotuberculosis*, and *Yersinia* spp.

The microorganism can be a fungus. Examples of fungi include, but are not limited to, *Aspergillus* spp., *Blastomyces* spp., *Candida* spp., *Cladosporium, Coccidioides* spp., *Cryptococcus* spp., *Exserohilum, fusarium, Histoplasma* spp., *Issatchenkia* spp., mucormycetes, *Pneumocystis* spp., ringworm, scedosporium, *Sporothrix*, and *Stachybotrys* spp. The microorganism can be a protozoan. Examples of protozoans include, but are not limited to, *Entamoeba histolytica, Plasmodium* spp., *Giardia lamblia*, and *Trypanosoma brucei*.

Antimicrobials

When the microorganism is a bacterium, exemplary antimicrobials include, but are not limited to, Amikacin, Aminoglycoside, Aminoglycoside amoxicillin, Aminoglycosides, Amoxicillin, Amoxicillin/clavulanate, Ampicillin, Ampicillin/sulbactam, Antitoxin, Arsphenamine, Azithromycin, Azlocillin, Aztreonam, β-lactam, Bacitracin, Capreomycin, Carbapenems, Carbenicillin, Cefaclor, Cefadroxil, Cefalexin, Cefalothin, Cefalotin, Cefamandole, Cefazolin, Cefdinir, Cefditoren, Cefepime, Cefixime, Cefoperazone, Cefotaxime, Cefoxitin, Cefpodoxime, Cefprozil, Ceftaroline, Ceftaroline fosamil, Ceftazidime, Ceftibuten, Ceftizoxime, Ceftobiprole, Ceftriaxone, Cefuroxime, Cephalosporin, Chloramphenicol, Chloramphenicol (Bs), Ciprofloxacin, Clarithromycin, Clindamycin, Clofazimine, Cloxacillin, Colistin, Co-trimoxazole, Cycloserine, Dalbavancin, Dapsone, Daptomycin, Demeclocycline, Dicloxacillin, Dirithromycin, Doripenem, Doxycycline, Enoxacin, Ertapenem, Erythromycin, Ethambutol, Ethambutol (Bs), Ethionamide, Flucloxacillin, Fluoroquinolone, Fluoroquinolones, Fosfomycin, Furazolidone, Fusidic acid, Gatifloxacin, Geldanamycin, Gemifloxacin, Gentamicin, Grepafloxacin, Herbimycin, Imipenem/Cilastatin, Isoniazid, Kanamycin, Levofloxacin, Lincomycin, Linezolid, Lomefloxacin, Loracarbef, Macrolides, Mafenide, Meropenem, Methicillin, Metronidazole, Mezlocillin, Minocycline, Moxifloxacin, Mupirocin, Nafcillin, Nafcillin, Nalidixic acid, Neomycin, Netilmicin, Nitrofurantoin (Bs), Norfloxacin, Ofloxacin, Oritavancin, Oxacillin, Oxytetracycline, Paromomycin, Penicillin, Penicillin G, Penicillin V, Piperacillin, Piperacillin/tazobactam, Platensimycin, Polymyxin B, Posizolid, Pyrazinamide, Quinupristin/Dalfopristin, Radezolid, Raxibacumab, Rifabutin, Rifampicin, Rifampin, Rifapentine, Rifaximin, Roxithromycin, Silver sulfadiazine, Sparfloxacin, Spectinomycin, Spectinomycin (Bs), Spiramycin, Streptogramins, Streptomycin, Sulbactam, Sulfacetamide, Sulfadiazine, Sulfadimethoxine, Sulfamethizole, Sulfamethoxazole, Sulfanilimide, Sulfasalazine, Sulfisoxazole, Sulfonamidochrysoidine, Tedizolid, Teicoplanin, Teixobactin, Telavancin, Telithromycin, Temafloxacin, Temocillin, Tetracycline, Thiamphenicol, ticarcillin, Ticarcillin/clavulanate, Ticarcillin/clavulanic acid, Tigecycline, Tigecycline (Bs), Tinidazole, TMP/SMX, Tobramycin, Torezolid, Trimethoprim (Bs), Trimethoprim-Sulfamethoxazole, Troleandomycin, Trovafloxacin, Vancomycin, and generics thereof or a variant thereof.

Antimicrobials whose interactions with the microorganism affect and are affected by the negative charges on the microorganism surface can include: polycationic aminoglycosides, which upon binding the cell surface displace $Mg^{2+}$ ions, which bridge lipid membrane components, thereby disrupting the outer membrane and enhancing drug uptake; cationic polymyxins (colistin and polymyxin B), whose binding to the microorganism cell is also dependent on the membrane's negative charge and for which both mutational and plasmid-mediated resistance occurs by reducing membrane negative charge; and daptomycin, a lipopeptide that resembles host innate immune response cationic antimicrobial peptides and requires $Ca^{2+}$ and phosphatidyl glycerol for its membrane-disrupting mechanism of action and for which resistance can also involve alteration in cell surface charge.

When the microorganism is a fungus, exemplary antimicrobials include 5-fluorocytosine, Abafungin, Albaconazole, Allylamines, Amphotericin B, Ancobon, Anidulafungin, Azole, Balsam of Peru, Benzoic acid, Bifonazole, Butoconazole, Candicidin, Caspofungin, Ciclopirox, Clotrimazole, Cresemba, Crystal violet, Diflucan, Echinocandins, Econazole, Efinaconazole, Epoxiconazole, Fenticonazole, Filipin, Fluconazole, Flucytosine, Grifulvin V, Griseofulvin, Gris-Peg, Haloprogin, Hamycin, Imidazoles, Isavuconazole, isavuconazonium, Isoconazole, Itraconazole, Ketoconazole, Lamisil, Luliconazole, Micafungin, Miconazole, Natamycin, Noxafil, Nystatin, Omoconazole, Onmel, Oravig, Oxiconazole, Posaconazole, Propiconazole, Ravuconazole, Rimocidin, Sertaconazole, Sporanox, Sulconazole, Terbinafine, Terconazole, Thiazoles, Thiocarbamate antifungal, Tioconazole, Tolnaftate, Triazoles, Undecylenic acid, Vfend, Voriconazole, and generics thereof or a variant thereof.

When the microorganism is a protozoan, exemplary antimicrobials include 8-Aminoquinoline, Acetarsol, Agents against amoebozoa, Ailanthone, Amodiaquine, Amphotericin B, Amprolium, Antitrichomonal agent, Aplasmomycin, Arsthinol, Artelinic acid, Artemether, Artemether/lumefantrine, Artemisinin, Artemotil, Arterolane, Artesunate, Artesunate/amodiaquine, Atovaquone, Atovaquone/proguanil, Azanidazole, Azithromycin, Benznidazole, Broxyquinoline, Buparvaquone, Carbarsone, Camidazole, Chiniofon, Chloroquine, Chlorproguanil, Chlorproguanil/dapsone, Chlorproguanil/dapsone/artesunate, Chlorquinaldol, Chromalveolate antiparasitics, Cinchona, Cipargamin, Clazuril, Clefamide, Clioquinol, Coccidiostat, Codinaeopsin, Cotrifazid, Cryptolepine, Cycloguanil, Dehydroemetine, Difetarsone, Dihydroartemisinin, Diloxanide, Diminazen, Disulfiram, Doxycycline, Eflomithine, ELQ-300, Emetine, Etofamide, Excavata antiparasitics, Fumagillin, Furazolidone, Glycobiarsol, GNF6702, Halofantrine, Hydroxychloroquine, Imidocarb, Ipronidazole, Jesuit's bark, KAF156, Lumefantrine, Maduramicin, Mefloquine, Megazol, Meglumine antimoniate, Melarsoprol, Mepacrine, Metronidazole, Miltefosine, Neurolenin B, Nicarbazin, Nifurtimox, Nimorazole, Nitarsone, Nitidine, Nitrofural, Olivacine, Omidazole, Oroidin, Pamaquine, Paromomycin, Pentamidine, Pentavalent antimonial, Phanquinone, Phenamidine, Piperaquine, Primaquine, Proguanil, Project 523, Propenidazole, Pyrimethamine, Pyronaridine, Quinfamide, Quinine, Ronidazole, Schedula Romana, SCYX-7158, Secnidazole, Semapimod, Sodium stibogluconate, Spiroindolone, Sulfadoxine, Sulfadoxine-Pyrimethamine, Sulfalene, Suramin, Tafenoquine, Teclozan, Tenonitrozole, Tilbroquinol, Tinidazole, Trimetrexate, Trypanocidal agent, Warburg's tincture, and generics thereof or a variant thereof.

An antimicrobial can be a drug that operates by a mechanism similar to a herein-recited drug. Other antimicrobial drugs known in the art can be used in the methods described herein.

Liquid Suspensions

The liquid can include a growth media, such as cation-adjusted Mueller Hinton broth (MHB). This media can comprise an additive, known to those skilled in the art to promote microorganism growth, and stability. In addition to different antimicrobials, different test wells can comprise an additive known to improve AST accuracy for specific antimicrobials. For example, additional sodium chloride can be added to tests comprising oxacillin and additional calcium can be added to tests comprising daptomycin.

Biological Samples

The microorganisms described herein can be derived from biological samples. In some embodiments, the biological sample is any sample that comprises a microorganism, e.g., a bacterium and a fungal cell. The biological sample can be derived from a clinical sample.

Exemplary biological samples can include, but are not limited to, whole blood, plasma, serum, sputum, urine, stool, white blood cells, red blood cells, buffy coat, tears, mucus, saliva, semen, vaginal fluids, lymphatic fluid, amniotic fluid, spinal or cerebrospinal fluid, peritoneal effusions, pleural effusions, exudates, punctates, epithelial smears, biopsies, bone marrow samples, fluids from cysts or abscesses, synovial fluid, vitreous or aqueous humor, eye washes or aspirates, bronchoalveolar lavage, bronchial lavage, or pulmonary lavage, lung aspirates, and organs and tissues, including but not limited to, liver, spleen, kidney, lung, intestine, brain, heart, muscle, pancreas, and the like, swabs (including, without limitation, wound swabs, buccal swabs, throat swabs, nasal swabs, vaginal swabs, urethral swabs, cervical swabs, rectal swabs, lesion swabs, abscess swabs, nasopharyngeal swabs, and the like), and any combination thereof. Also included are bacteria cultures or bacteria isolates, fungal cultures or fungal isolates. The ordinary-skilled artisan can also appreciate that isolates, extracts, or materials obtained from any of the above exemplary biological samples are also within the scope of the present invention.

Microorganisms obtained from a biological sample can be cultured or otherwise processed as is routinely performed in the art.

Controls Used in AST Methods

Controls can include antimicrobials for which the microorganism is not susceptible. As examples, if the assay is used to determine the susceptibility of gram-positive bacteria, then the controls (and the test incubations) can include one or more antimicrobials that target gram-negative bacteria, and if the assay is used to determine the susceptibility of eukaryotic microorganisms, the control (and the test incubations) can include one or more antibacterial antimicrobials.

In some embodiments, the control is a positive control measured from microorganisms under otherwise identical conditions but without antimicrobials or with one or more antimicrobials for which the microorganisms are not susceptible. In some embodiments, the control is measured from microorganisms under otherwise identical conditions but without nutrients. In some embodiments, the control is measured from microorganisms under otherwise identical conditions with one or more toxins known to inhibit growth of the microorganisms.

In some embodiments, the control is a negative control. A negative control may be a control of identical set up as the rest of the assays, but missing at least one component. In most cases, a negative control has no microorganisms, with everything else identical to the rest of the assay set ups. In some assays a background control is present.

Controls can be historic controls. In some embodiments, the test incubations are performed after control incubations have been performed. In some embodiments, controls are performed in a cartridge distinct from the cartridge comprising the test incubations.

Automated AST Methods

The methods described herein can be performed in an automated manner using commercially available equipment, custom made equipment, or a combination thereof. Automating the methods allows for performance of a greater number of assays as well as increased consistency among assays. Automation can also increase speed and resolution of these methods.

Surface-Binding Probe Assays

Surface-binding assays (also referred to as surface-binding probe assays) can utilize a signaling agent. Signaling agents typically comprise a moiety capable of binding to a microorganism (e.g., an antibody and/or a lectin that bind to a microorganism surface, a charged moiety and/or a functional moiety that non-specifically binds to the microorganism surface) and a chemical moiety capable of providing a signal or contributing to production of a signal (e.g., an enzyme chemiluminophore, and lanthanide chelate). Exemplary enzymes include horseradish peroxidase, alkaline phosphatase, acetyl cholinesterase, glucose oxidase, beta-D-galactosidase, beta-lactamase, and a combination thereof.

A signal generator can include one or more chemical moieties conjugated to one or more microorganism receptors. Signal generators include, but are not limited to, one or more catalysts (including enzymes, metal-oxide nanoparticles, organometallic catalysts, nanoparticles designed for signal amplification (such as those described in the U.S. Provisional Applications to which the present application claims priority and incorporates by reference in their entireties), bacteriophages comprising signal generating elements, fluorophores (including organic fluorophores, europium, or ruthenium(II), rhenium(I), palladium(II), platinum(II)-containing organometallics), and/or colorimetric dyes (including organic stains). Combinations of the above can be used, such as nanoparticles, dendrimers, and/or other nanoscale structures with enzymes, fluorophores, and/or organometallic molecules.

The chemical moiety can be conjugated to a signaling agent before contacting the signaling agent to a microorganism, while the signaling agent is initially contacted to a microorganism, or after the signaling agent has contacted a microorganism.

When the signaling agents are added to AST dilutions containing a microorganism, signaling agent receptors (e.g., moieties that can bind specifically or non-specifically to a microorganism) can associate with microorganism surfaces. Thus, the more intact microorganisms, for example, there are in solution, the greater the number of signaling agents that will be associated with these bacteria. Consequently, there is an inverse relationship between the number of intact bacteria and the number of signaling agents that are free in solution, as defined by those not bound to intact bacteria. Note that free signaling agents can be bound to soluble microbial components if, for example, microorganisms lyse in response to antimicrobial treatment.

The number of signaling agents that associate with and/or intercalate into microorganism surfaces is proportional to the microorganism surface area. Microorganism surface area is strongly associated with truly resistant microorganisms. In particular, in the case of microorganisms that swell or elongate in response to MIC- and sub-MIC concentrations of antimicrobials (e.g., filament forming bacteria), metabolic and/or volumetric identifications are known to give false susceptibility profiles for rapid AST time points, defined as those less than six hours. To overcome this limitation, the present invention translates microorganism surface area (rather than volume) into a measurable signal such as an optical signal. The methods described herein are able to accurately determine microorganism resistance profiles in less than six hours.

In order to separate signaling agents associated with and/or intercalated into microorganisms from free signaling agents, it can be necessary to perform one or more separation and/or competitive binding steps. Such steps include, but are not limited to, centrifugation (e.g., with a g-force >500×g), filtration (e.g., via a filter having pores smaller than or equal to 0.45 microns, or smaller than or equal to 0.2 microns), electrophoresis, and/or magnetic capture; such steps are well-known to those skilled in the art.

In order to promote signaling agent binding and/or reduce background, it can further be advantageous, before adding signaling agents, to separate microorganisms from the liquid in which they were suspended during incubation. Such separations can include but are not limited to, centrifugation, filtration, electrophoresis, and/or magnetic capture.

Signaling agents can be added together with microorganisms and/or antimicrobials, such that they are present for the entire AST incubation period. This total period can be up to twenty-four hours, or within eight hours, or within five hours. Alternatively, signaling agents can be added to microorganisms and antimicrobial after a prescribed incubation period. This period can be up to twenty-four hours, or within eight hours, or within four hours.

Signaling agents are designed to associate with and/or intercalate in microorganism surfaces, including walls and/or membranes. Signaling agents designed for association comprise binding moieties including, but not limited to, one or more antibodies, lectins, other proteins, small molecules with one or more charged chemical groups, small molecules with one or more functional chemical groups, phages, glycoproteins, peptides, aptamers, charged small molecules, small molecules with fixed charges, charged polymers, charged polymers with fixed charges, hydrophobic small molecules, charged peptide, charged peptides with fixed charges, peptides with alternating hydrophilic and hydrophobic regions, and/or small molecule ligands, which can or cannot be organometallic complexes. Molecules designed for microorganism association are well-known to those skilled in the art. Signaling agents can remain bound to microorganisms and/or can be internalized, thus all associations are included. Signaling agents designed for intercalation can include, but are not limited to, small hydrophobic molecules, hydrophobic peptides, and/or peptides with alternating hydrophobic and hydrophilic regions. Molecules designed for microorganism intercalation are well-known to those skilled in the art. Signaling agents can further be specific to one or more types of microorganisms. Signaling agents can have multiple receptors. These can enhance binding and/or enable simultaneous binding to two or more microorganisms, which can further serve to agglutinate bacteria. Prior to or concurrently with the addition of signaling agents it can be advantageous to adjust the solution pH. This can be beneficial for enhancing charge-charge interactions between microorganisms and signaling agents. The anionic charge of microorganisms can be increased by titrating the solution pH above neutral (more basic). It can thus be beneficial to utilize moieties with one or more fixed, cationic charges.

It is noteworthy that the signaling agent can specifically bind to a microorganism (e.g., an antibody that specifically binds to a microorganism species or a strain of microorganism) or my non-specifically binds to a microorganism (e.g., by a generic covalent or non-covalent bond formation and another non-specific chemical association known in the art).

Alternately, chemicals and/or biochemicals which are capable of associating with signaling agents can be added to the liquid in which the microorganisms are suspended during growth, such that chemicals and/or biochemicals are incorporated into microorganisms during incubation. This can serve to enhance signaling agent association with microorganisms. In alternative embodiments, the signaling agents themselves can be present in the liquid in which the microorganisms are suspended during incubation and can be incorporated into microorganisms during growth.

The signaling agents can comprise an amplifier signal generator (amplifier group), such that the signal from each intact microorganism can be amplified beyond the number of signaling agents associated with each microorganism. For example, the enzyme horseradish peroxidase (HRP) is known to be able to amplify signals $>1\times10^4$-fold. Thus, if one hundred HRP molecules are bound to each microorganism surface, an amplification of $10^6$ can be achieved. This can increase the speed with which AST determinations can be made by enabling discrimination of microorganism concentrations that cannot otherwise be differentiated. Use of Europium formulations similarly provides signal amplification.

Alternatively, the signaling agents can comprise optical dye precursors known to those skilled in the art as membrane dyes that are designed to greatly increase fluorescence emission upon intercalation into a hydrophobic region, such as a cell membrane. Assays designed with these signaling agents can require microorganisms to be concentrated into a smaller volume, approaching a plane, to produce sufficient signals so as to be easily optically measured. Interfering species can require the use of near-IR fluorophores.

Exemplary amplifier groups include those described in, e.g., International Publication No. WO 2016/015027 and in International Application No. PCT/US16/42589, each of which is incorporated by reference in its entirety. An amplifier group can comprise a catalyst, a fluorophore, a colorimetric dye, an enzyme, a catalyst, or a nanoparticle. Exemplary fluorophores include those described in Table 1 of International Application No. PCT/US16/42589, which is incorporated by reference in its entirety. An amplifier group can comprise a lanthanide. Lanthanides include, but are not limited to, is europium, strontium, terbium, samarium, or dysprosium.

An amplifier group can comprise an organic fluorophore, e.g., a coordination complex. The coordination complex can be europium coordination complex, a ruthenium coordination complex, a rhenium coordination complex, a palladium coordination complex, a platinum coordination complex. An amplifier can comprise a chemiluminophore, a quantum dot, an enzyme, an iron coordination catalyst, a europium coordination complex, a ruthenium coordination complex, a rhenium coordination complex, a palladium coordination complex, a platinum coordination complex, a samarium coordination complex, a terbium coordination complex, or a dysprosium coordination complex.

In some embodiments, an amplifier group comprises a moiety that is:

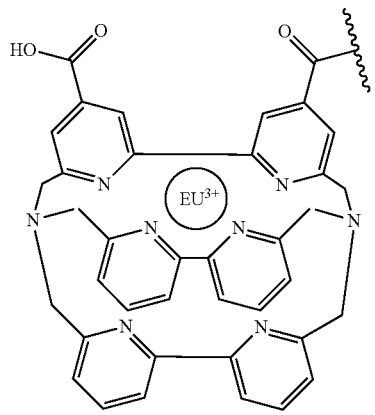

(III)

-continued

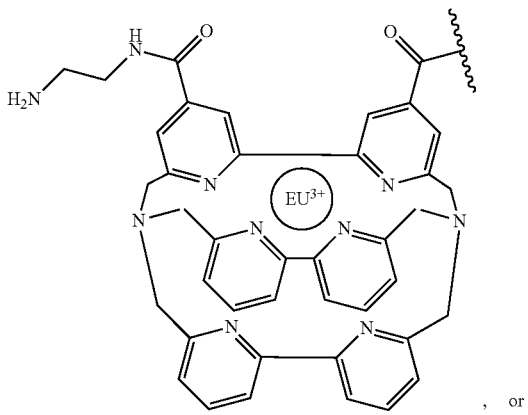

(IV)

, or

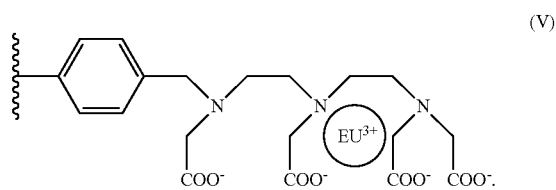

(V)

In some embodiments, an amplifier group comprises a moiety that is:

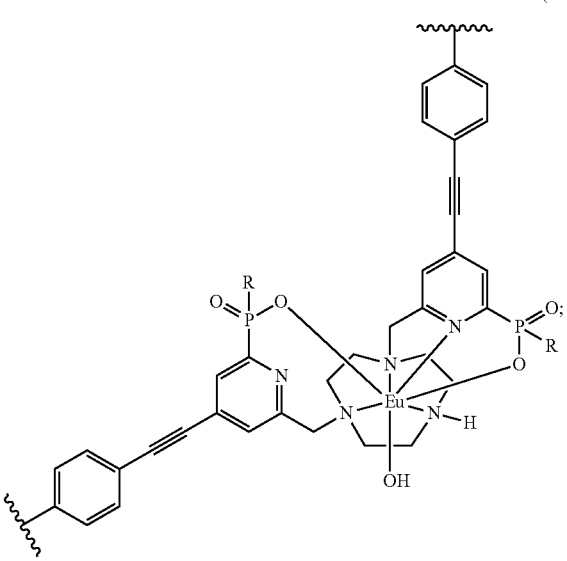

(VI)

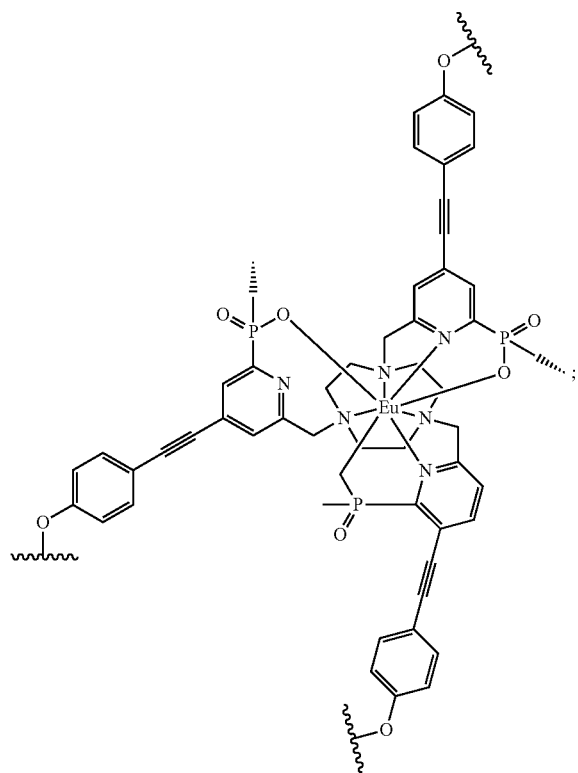

(VII)

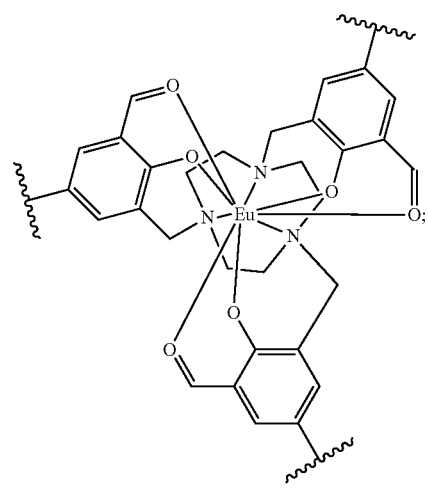

(VIII)

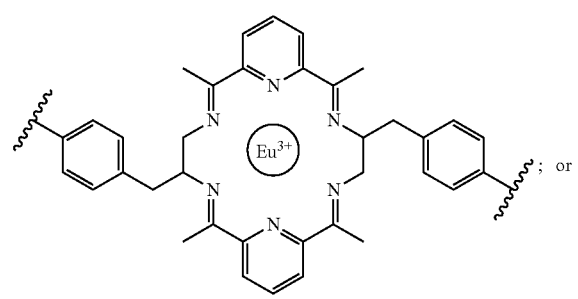

(IX)

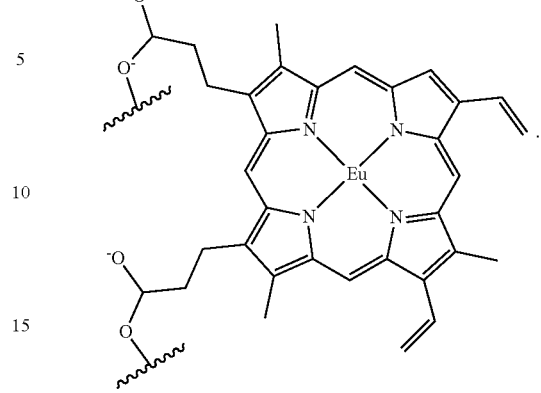

(X)

An amplifier group can comprise a fluorophore or colormetric dye. Suitable fluorophores and colormetric dyes are well known to those skilled in the art and are described in *The Molecular Probes® Handbook: A Guide to Fluorescent Probes and Labeling Technologies*, 11th Ed. (2010) and Gomes, Femandes, and Lima *J. Biochem. Biophys. Methods* 65 (2005) pp 45-80 and Manafi, Kneifel, and Bascomb *Microbiol. Rev.* 55 (1991) pp 335-348, which are herein incorporated by reference in their entirety. Exemplary fluorophores also include those described in, e.g., International Publication No. WO 2016/015027 and in International Application No. PCT/US16/42589, each of which is incorporated by reference in its entirety.

Examples of suitable fluorophore or colormetric dyes include, but are not limited to, ethidium bromide, propidium iodide, SYTOX green, phenanthridines, acridines, indoles, imidazoles, cyanine, TOTO, TO-PRO, SYTO, 5-carboxy-2, 7-dichlorofluorescein, 5-Carboxyfluorescein (5-FAM), 5-Carboxynapthofluorescein, 5-Carboxytetramethylrhodamine (5-TAMRA), 5-FAM (5-Carboxyfluorescein), 5-HAT (Hydroxy Tryptamine), 5-ROX (carboxy-X-rhodamine), 6-Carboxyrhodamine 6G, 7-Amino-4-methylcoumarin, 7-Aminoactinomycin D (7-AAD), 7-Hydroxy-4-methylcoumarin, 9-Amino-6-chloro-2-methoxyacridine, ACMA (9-Amino-6-chloro-2-methoxyacridine), Acridines, Alexa Fluors, Alizarin, Allophycocyanin (APC), AMCA (Aminomethylcoumarin), Bodipy, Carboxy-X-rhodamine, Catecholamine, Fluorescein (FITC), Hydroxycoumarin, Lissamine Rhodamine, Monobromobimane, Oregon Green, Phycoerythrin, SYTO, Thiadicarbocyanine (DiSC3), Thioflavin, X-Rhodamine, C or TetramethylRodamineIsoThioCyanate.

An amplifier group can comprise an organometallic compound, transition metal complex, or coordination complex. Examples of such amplifier groups include, but are not limited to, those described in EP 0 180 492, EP 0 321 353, EP 0 539 435, EP 0 539 477, EP 0 569 496, EP139675, EP64484, U.S. Pat. Nos. 4,283,382, 4,565,790, 4,719,182, 4,735,907, 4,808,541, 4,927,923, 5,162,508, 5,220,012, 5,324,825, 5,346,996, 5,373,093, 5,432,101, 5,457,185, 5,512,493, 5,527,684, 5,534,622, 5,627,074, 5,696,240, 6,100,394, 6,340,744, 6,524,727, 6,717,354, 7,067,320, 7,364,597, 7,393,599, 7,456,023, 7,465,747, 7,625,930, 7,854,919, 7,910,088, 7,955,859, 7,968,904, 8,007,926, 8,012,609, 8,017,254, 8,018,145, 8,048,659, 8,067,100, 8,129,897, 8,174,001, 8,183,586, 8,193,174, 8,221,719, 8,288,763, 8,362,691, 8,383,249, 8,492,783, 8,632,753, 8,663,603, 8,722,881, 8,754,206, 8,890,402, 8,969,862, 9,012,034, 9,056,138, 9,118,028, 9,133,205, 9,187,690, 9,193,746, 9,312,496, 9,337,432, 9,343,685, 9,391,288, and 9,537,107, which are incorporated by reference in their entirety. Exemplary organometallic compounds, transition metal complexes, or coordination complexes also include those described in, e.g., International Publication No. WO 2016/015027 and in International Application No. PCT/US16/42589, each of which is incorporated by reference in its entirety.

In some embodiments, amplifier group is a lanthanide coordination complex such as a complex between a lanthanide (e.g., Eu or Tb) and a tetradentate ligand or a complex between a lanthanide (e.g., Eu or Tb) and a cryptate ligand. In some embodiments, amplifier group is a coordination complex of Lanthanum (La), Cerium (Ce), Praseodymium (Pr), Neodymium (Pm), Samarium (Sm), Europium (Eu), Gadolinium (Gd), Terbium (Tb), Dysprosium (Dy), Holmium (Ho), Erbium (Er), Thulium (Tm), Ytterbium (Yb), Lutetium (Lu), Ruthenium (Ru), Rhodium (Rh), Palladium (Pd), Osmium (Os), Iridium (Ir), or Platinum (Pt). In some embodiments, amplifier group is a coordination complex of a rare earth metal collectively refers to 17 elements consisting of a group of 15 elements from lanthanum having an atomic number of 57 to lutetium having an atomic number of 71 (lanthanides), and two additional elements consisting of scandium having an atomic number of 21 and yttrium having an atomic number of 39. Specific examples of rare earth metals include europium, terbium, lanthanum, cerium, praseodymium, neodymium, promethium, samarium, gadolinium, dysprosium, holmium, erbium, thulium, ytterbium, lutetium, scandium and yttrium. In some embodiments, amplifier group is a coordination complex of a lanthanide (e.g., Europium or Terbium) with diethylenetriaminetetraacetic acid or cryptate ligand.

Specific examples of a signaling agent include, but are not limited to, moieties comprising:

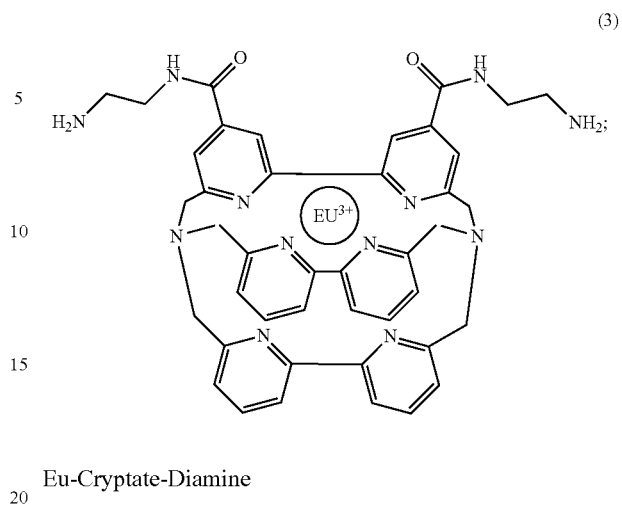

Eu-Cryptate-Diamine

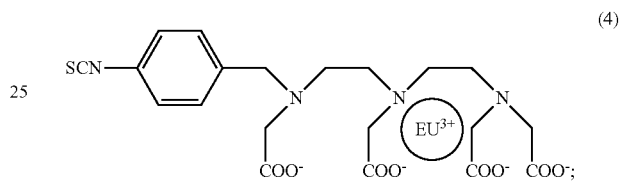

Eu-N1-ITC (Delfia)

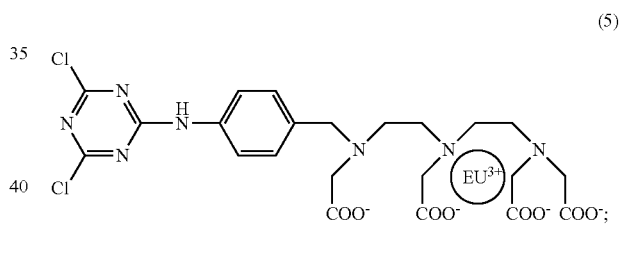

Eu-N1-DTA

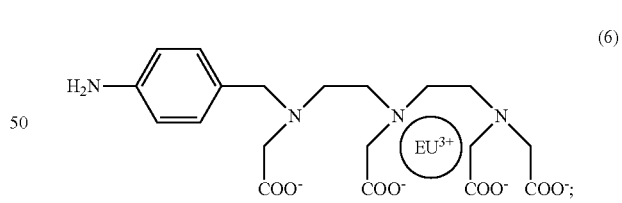

Eu-N1-Amino

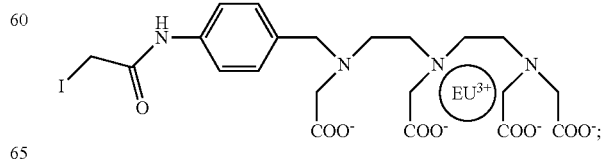

Eu-N1-Iodoacetamido (1)

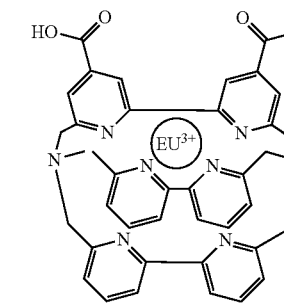

Eu-Cryptate-Maleimide (2)

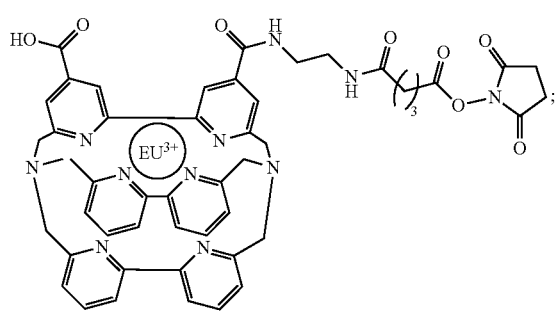

Eu-Cryptate-NHS

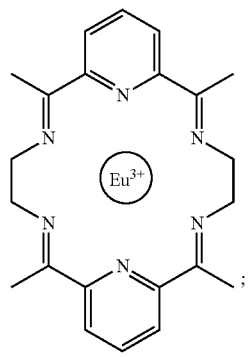

(8)

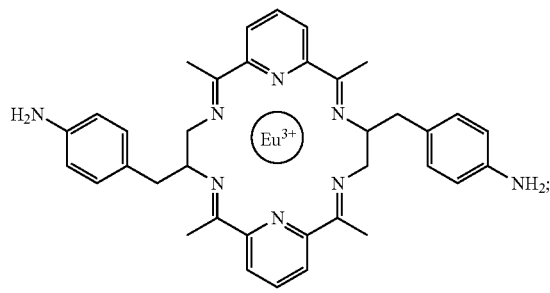

(9)

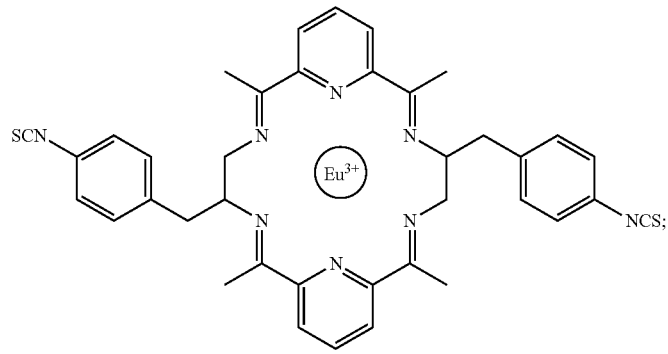

(10)

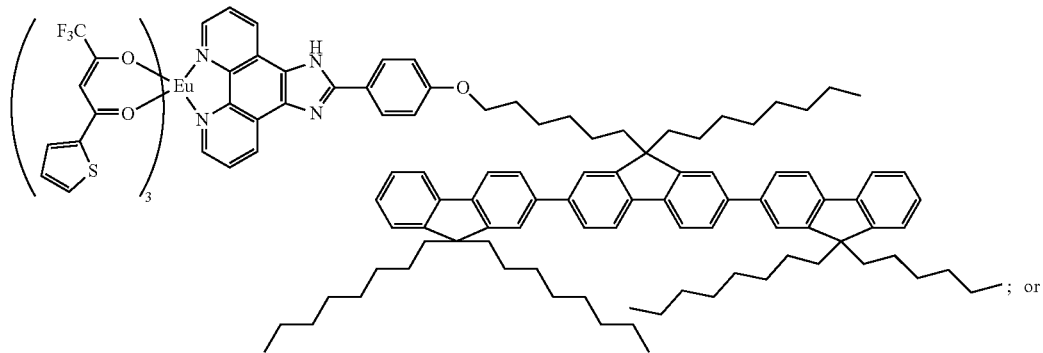

; or (11)

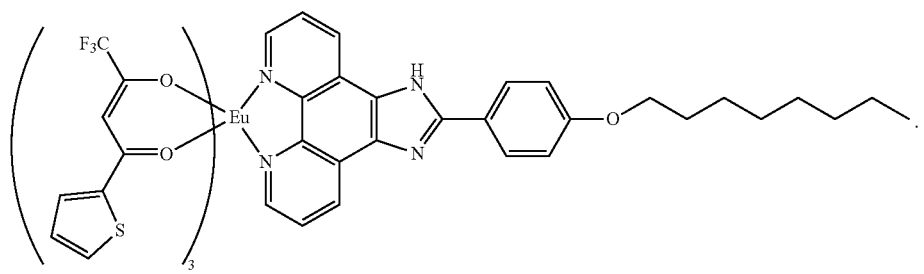

(12)

A signaling agent can comprise a luminophore (donor) which features high luminescence quantum efficiency and long luminescence decay time (>100 ns). Exemplary luminophores are cationic, metalorganic complexes of palladium, rhodium, platinum, ruthenium, osmium, rare earths (in particular, europium and lanthanum). The organic portion of these metalorganic complexes can consist, for example, of ligands from the group of porphyrins, bipyridyls, phenanthrolines or other heterocyclical compounds.

In some embodiments, a signaling agent capable of binding a microorganism surface comprises an antibody (e.g., monoclonal or polyclonal), modified antibodies (e.g., biotinylated monoclonal antibody, biotinylated polyclonal antibody, europium chelate-antibody, horseradish peroxidase-conjugated antibody), antibody variants (e.g., Fab: fragment, antigen-binding (one arm); F(ab')$_2$: fragment, antigen-binding, including hinge region (both arms); Fab': fragment, antigen-binding, including hinge region (one arm); scFv: single-chain variable fragment; di-scFv: dimeric single-chain variable fragment; sdAb: single-domain antibody;

Bispecific monoclonal antibodies; trifunctional antibody; and BiTE: bi-specific T-cell engager), WGA-Biotin, PolymixinB-Biotin, lectin, natural peptide, synthetic peptides, synthetic and/or natural ligands, synthetic and/or natural polymers, synthetic and/or natural glycopolymers, carbohydrate-binding proteins and/or polymers, glycoprotein-binding proteins and/or polymers, charged small molecules, other proteins, bacteriophages, and/or aptamers.

In some embodiments, a signaling agent capable of binding a microorganism surface comprises or is formed from a structure comprising an antibody, lectin, natural peptide, synthetic peptides, synthetic and/or natural ligands, synthetic and/or natural polymers, synthetic and/or natural glycopolymers, carbohydrate-binding proteins and/or polymers, glycoprotein-binding proteins and/or polymers, charged small molecules, other proteins, bacteriophages, and/or aptamers.

In some embodiments, a signaling agent capable of binding a microorganism surface comprises an amplifier group that comprises a lanthanide coordination complex, and/or an enzyme and streptavidin and/or an antibody and/or aptamer. In some embodiments, a signaling agent capable of binding a microorganism surface comprises a binding moiety comprising a polyclonal and/or monoclonal antibody.

In some embodiments, a signaling agent capable of binding a microorganism surface comprises a binding moiety comprising a modified antibody. Exemplary modified antibodies include a biotinylated monoclonal antibody, biotinylated polyclonal antibody, a europium chelate-antibody, and a horseradish peroxidase-conjugated antibody. In some embodiments, a signaling agent capable of binding a microorganism surface comprises a binding moiety comprising an antibody variant. Exemplary antibody variants include Fab: fragment, antigen-binding (one arm); F(ab')₂: fragment, antigen-binding, including hinge region (both arms); Fab': fragment, antigen-binding, including hinge region (one arm); scFv: single-chain variable fragment; di-scFv: dimeric single-chain variable fragment; sdAb: single-domain antibody; Bispecific monoclonal antibodies; trifunctional antibody; and BiTE: bi-specific T-cell engager), In some embodiments, a signaling agent capable of binding a microorganism surface comprises WGA-Biotin or PolymixinB-Biotin. In some embodiments, a signaling agent capable of binding a microorganism surface comprises a binding moiety comprising a synthetic and/or natural ligand and/or peptide. In some embodiments, a ligand and/or peptide is selected from bis(zinc-dipicolylamine), TAT peptide, serine proteases, cathelicidins, cationic dextrins, cationic cyclodextrins, salicylic acid, lysine, and combinations thereof. In some embodiments, a signaling agent capable of binding a microorganism surface comprises a binding moiety comprising a synthetic and/or natural polymer and/or glycopolymer. In embodiments, a natural and/or synthetic polymer is linear or branched and selected from amylopectin, Poly(N-[3-(dimethylamino)propyl] methacrylamide), poly(ethyleneimine), poly-L-lysine, poly[2-(N,N-dimethylamino)ethyl methacrylate], and combinations thereof. In some embodiments, a natural and/or synthetic polymer and/or glycopolymer comprises moieties including, but not limited to, chitosan, gelatin, dextran, trehalose, cellulose, mannose, cationic dextrans and cyclodextrans, quaternary amines, pyridinium tribromides, histidine, lysine, cysteine, arginine, sulfoniums, phosphoniums, or combinations thereof including, but not limited to, co-block, graft, and alternating polymers. In some embodiments, a signaling agent capable of binding a microorganism surface comprises a binding moiety comprising a glycoprotein selected from mannose-binding lectin, other lectins, annexins, and combinations thereof.

In some embodiments, a signaling agent capable of binding to a microorganism surface comprises: an antibody; and a europium coordination complex. In some embodiments, a signaling agent capable of binding to a microorganism surface comprises a linker group L that comprises NH₂-PEG-Biotin (2K), NH₂-PEG-Biotin (4K), sulfo-NHS-Biotin, WGA-Biotin, or polymixinB-Biotin. In some embodiments, a signaling agent capable of binding to a microorganism surface comprises a europium complex comprises:

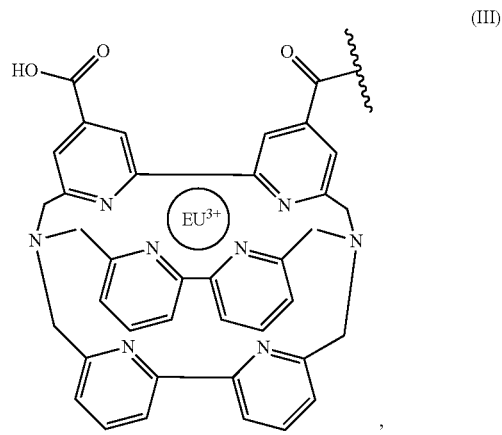

(III)

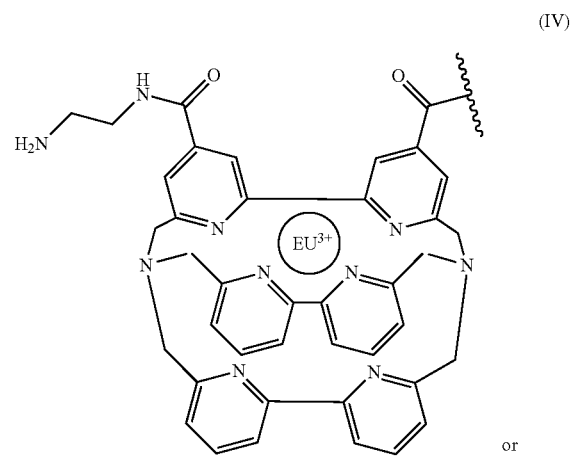

(IV)

or

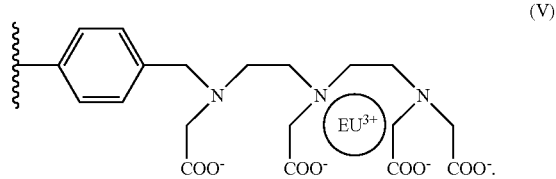

(V)

In some embodiments, a signaling agent capable of binding to a microorganism surface comprises a europium complex comprises:

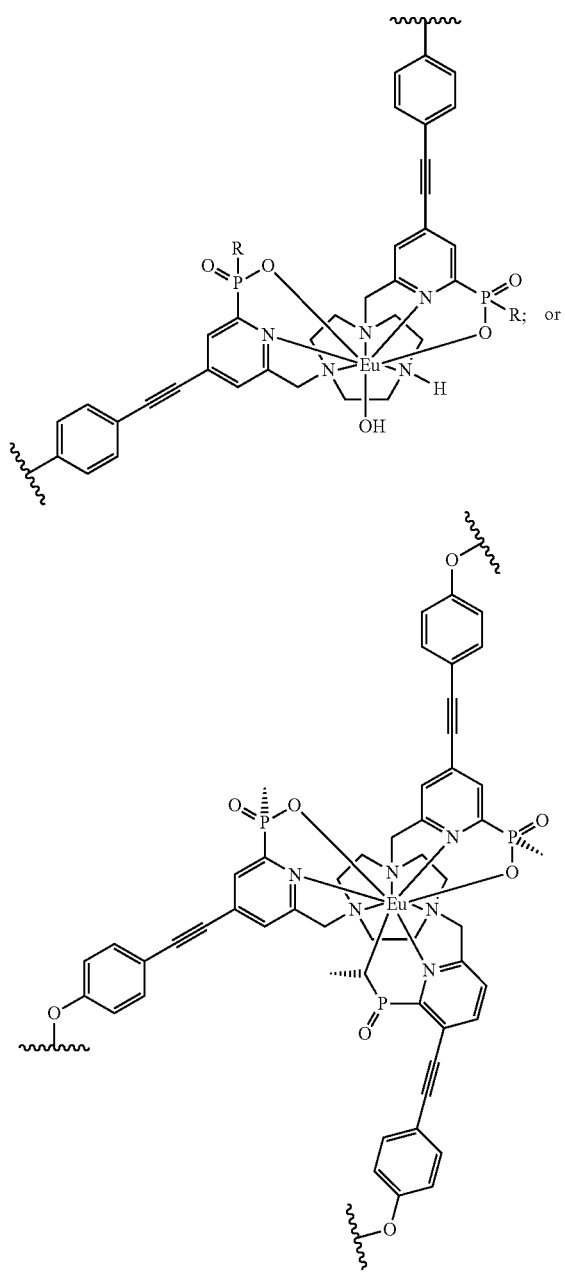

Exemplary Advantages of AST Methods

Aspects of the methods described herein can deliver accurate, low-cost phenotypic AST results by performing a plurality of growth assays in order to determine which antimicrobial is most effective against a given microorganism. The methods herein can provide appropriate concentrations of a given effective antimicrobial for prescribing purposes. In some embodiments, the methods provide for generating a recommendation for treatment of a patient's infection that is caused by a given microorganism. A patient can be a host that can serve as a source of a biological sample or specimen as discussed herein. In certain aspects, the donor is a vertebrate animal, which is intended to denote any animal species (e.g., a mammalian species such as a human being). In certain embodiments, a patient is any animal host, including but not limited to, human and non-human primates, avians, reptiles, amphibians, bovines, canines, caprines, cavities, corvines, epines, equines, felines, hircines, lapines, leporines, lupines, ovines, porcines, racines, vulpines, and the like, including, without limitation, domesticated livestock, herding or migratory animals or birds, exotics or zoological specimens, as well as companion animals, pets, and any animal under the care of a veterinary practitioner.

In some embodiments, the methods herein provide low-cost, phenotypic ASTs from standard microbial colony isolates or from direct-from-positive blood samples, in less than 8 hours, less than 6 hours, less than 5 hours, or less than 4 hours. This can allow for standard clinical microbiology laboratories same-shift, phenotypic AST results. This can shorten current wait times by over twenty hours and can match direct-from-positive blood culture MALDI-TOF identifications currently nearing FDA trials, as well as direct-from-positive blood culture multiplex PCR identification platforms that have already obtained FDA clearance. In some embodiments, this design enables the methods described herein ("fast-AST" platform) to break the traditional speed vs. cost tradeoff. The methods can be compatible both with standard microplate formats (e.g., having 6, 12, 24, 48, 96, 384, or 1536 wells) and conventional optical detectors.

Identification and antimicrobial susceptibility testing (AST) of the invading pathogen with speed and accuracy can allow for timely administration of the most effective therapeutic agent. Such treatment can ameliorate the infection, decrease length of stay for hospitalized patients, and diminish the time patients are subject to broad spectrum antimicrobials, the latter contributing the global epidemic of antimicrobial resistance. In contrast, the currently-accepted over thirty hour wait for microorganism identification and susceptibility results necessitates overuse of broad-spectrum antimicrobials and longer than necessary patient stay. For this reason, the Presidential Advisory Council on Combating Antibiotic-Resistant Bacteria recently made the development and use of rapid diagnostics for the detection of antibiotic resistant bacteria one of its main goals.

Treatment of Patients with Infections

The methods described herein can provide for treating patients with infections caused by microorganisms. AST determinations can allow health care professionals or diagnostic scientists to make recommendations to a patient for a desired course of action or treating regimen. In some embodiments, the recommendations are given faster and more accurately as provided by the invention. Recommendations for treatment of infections can include choice of a specific antimicrobial or a combination of antimicrobials or a dose of such antimicrobials. In some embodiments, such recommendations are provided to or generated by a physician based upon MIC and/or QSR results.

Any of the above aspects and embodiments can be combined with any other aspect or embodiment as disclosed in the Drawings, in the Summary, and/or in the Detailed Description, including the below Examples.

EXAMPLES

This invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below.

Example 1: Parallel Antimicrobial Susceptibility Assays

This example depicts multiple antimicrobial susceptibility assays performed in parallel (e.g., sharing the same incubation period).

The microplates, each well comprising 100 μL Mueller Hinton Broth (MH), were inoculated with the prepared antimicrobial dilutions and incubated at 35° C. for 3 hours, 45 minutes. The microplates were removed from the shaking incubator after 3 hours, 45 minutes, and 10 μL of alamarBlue® was added to each well. The microplates were then placed back in the incubator for 1 hour. When the microplates were removed from the shaking incubator, the wells were read for fluorescence (Excitation 560/Emission 590 nm) on a BioTek H1 plate reader. Then, 100 μL of a detergent solution comprising ethylenediaminetetraacetic acid and cetyl trimethylammonium bromide was added to each well of both microplates. The two microplates were then shaken at 300 rpm for 10 minutes, followed by centrifugation for 2.5 minutes at 2500×g to pellet. The MH broth was then aspirated and 100 μL of 25 mM PBS was added to each well of both microplates. 10 μL of the chemical moiety (here, 0.005% Glutaraldehyde) was then added to each well, followed by 10 μL of Europium-Cryptate formulation (as the signaling agent) to each well (20 ng/well). The two microplates were then shaken at 300 rpm for 30 minutes. After, both plates were centrifuged for 2.5 minutes at 30 2500×g to pellet. The solution was aspirated, and a wash of 200 μL PBS-tween was added to each well, followed by a centrifugation to pellet. After aspiration of solution, a second identical wash of 200 μL PBS-tween occurred, followed by a final centrifugation to pellet. 200 μL PBS-tween was added to each well. The plate was then read using time resolved fluorescence on a BioTek H1 plate reader.

Table 3 shows the results when both a metabolic probe assay and a surface-binding assay were performed as compared to the CLSI overnight method with respect to determining the minimum inhibitory concentrations (MIC) of twenty different antimicrobials against various *E. coli* strains. De-identified isolated clinical *E. coli* strains were obtained from the Center for Disease Control (CDC) and BEI Resources (managed under contract by American Type Culture Collection (ATCC), among other sources. The CLSI Reference method-determined MIC is given in bold and the result of each of the 2 rapid assays is given as either "ok" (matches exactly), "resistant" (MIC greater than reference by >1 dilution), or "susceptible" (MIC less than reference by <1 dilution). The data shows that utilizing two different assays is helpful for ensuring accurate rapid AST results.

TABLE 3

| *E. coli* strain | | | | | | | | | |
|---|---|---|---|---|---|---|---|---|---|
| Clinical Sample 1 | Anti-microbial | IPM | AMP | CAZ | GEN | LVX | CRO | PEN | TET |
| | MIC (CLSI Ref) | <0.12 | 4 | 0.25 | 0.5 | <0.06 | <0.12 | >16 | 4 |
| | Anti-microbial | SXT | CIP | SAM | FEP | TZP | ERT | CFZ | CST |
| | MIC (CLSI Ref) | <0.5 | 0.06 | 4 | <0.03 | 4 | 0.008 | 2 | 0.12 |
| | Anti-microbial | MEM | TOB | ATM | AMK | | | | |
| | MIC (CLSI Ref) | <0.06 | 2 | <0.25 | 4 | | | | |
| Clinical Sample 2 | Anti-microbial | IPM | AMP | CAZ | GEN | LVX | CRO | PEN | TET |
| | MIC | <0.12 | >32 | 2 | 4 | <0.06 | 2 I | >16 | >32 R |
| | Anti-microbial | SXT | CIP | SAM | FEP | TZP | ERT | CFZ | CST |
| | MIC (CLSI Ref) | 4 R | 0.06 | 16 I | <0.03 | 8 | 0.015 | 32 R | 0.12 |
| | Anti-microbial | MEM | TOB | ATM | AMK | | | | |
| | MIC | <0.06 | 1 | 0.5 | 4 | | | | |
| CDC Carba36 | Anti-microbial | IPM | AMP | CAZ | GEN | LVX | CRO | PEN | TET |
| | MIC (CLSI Ref) | <0.12 | >32 | 4 | 2 | >8 | 1 | >16 | 8 |
| | Anti-microbial | SXT | CIP | SAM | FEP | TZP | ERT | CFZ | CST |
| | MIC (CLSI Ref) | <0.5 | >4 | >32 | 0.12 | 128 | 0.12 | >32 | 0.25 |
| | Anti-microbial | MEM | TOB | ATM | AMK | | | | |
| | MIC | <0.06 | 1 | 8 ? | 4 | | | | |
| Clinical Sample 4 | Anti-microbial | IPM | AMP | CAZ | GEN | LVX | CRO | PEN | TET |
| | MIC | 0.25 | >32 | 0.25 | 0.5 | >8 | <0.12 | >16 | 4 |
| | Anti-microbial | SXT | CIP | SAM | FEP | TZP | ERT | CFZ | CST |
| | MIC (CLSI Ref) | >32 | >4 | 16 | <0.03 | 4 | 0.008 | 2 | 0.25 |
| | Anti-microbial | MEM | TOB | ATM | AMK | | | | |
| | MIC | <0.06 | 1 | <0.25 | 4 | | | | |
| Clinical Sample 5 | Anti-microbial | IPM | AMP | CAZ | GEN | LVX | CRO | PEN | TET |
| | MIC | <0.12 | >32 | 0.25 | 2 | >8 | <0.12 | >16 | >32 |
| | Anti-microbial | SXT | CIP | SAM | FEP | TZP | ERT | CFZ | CST |
| | MIC (CLSI Ref) | >32 | >4 | 8 | <0.03 | 4 | 0.008 | 2 | 0.25 |
| | Anti-microbial | MEM | TOB | ATM | AMK | | | | |
| | MIC | <0.06 | 1 | <0.25 | 4 | | | | |
| Clinical Sample 6 | Anti-microbial | IPM | AMP | CAZ | GEN | LVX | CRO | PEN | TET |
| | MIC | <0.12 | 4 | 0.12 | 0.5 | <0.06 | <0.12 | 16 | 2 |
| | Anti-microbial | SXT | CIP | SAM | FEP | TZP | ERT | CFZ | CST |
| | MIC (CLSI Ref) | 2 | 0.03 | 2 | <0.03 | 2 | 0.008 | 1 | 0.12 |
| | Anti-microbial | MEM | TOB | ATM | AMK | | | | |
| | MIC | <0.06 | 1 | <0.25 | 4 | | | | |
| Clinical Sample 7 | Anti-microbial | IPM | AMP | CAZ | GEN | LVX | CRO | PEN | TET |
| | MIC | <0.12 | >32 | 0.25 | 0.5 | <0.06 | <0.12 | >16 | 4 |
| | Anti-microbial | SXT | CIP | SAM | FEP | TZP | ERT | CFZ | CST |
| | MIC (CLSI Ref) | >32 | <0.015 | 16 | <0.03 | 4 | 0.008 | 2 | 0.12 |

TABLE 3-continued

|  |  |  |  |  |  |  |  |  |
|---|---|---|---|---|---|---|---|---|
|  | Anti-microbial | MEM | TOB | ATM | AMK |  |  |  |
|  | MIC | <0.06 | 1 | <0.25 | 2 |  |  |  |
| Clinical | Anti-microbial | IPM | AMP | CAZ | GEN | LVX | CRO | PEN | TET |
| Sample | MIC | 0.5 | >32 | >32 | 1 | <0.06 | 64 | >16 | 8 |
| 8 | Anti-microbial | SXT | CIP | SAM | FEP | TZP | ERT | CFZ | CST |
|  | MIC (CLSI Ref) | <0.5 | 0.03 | 64 | 0.5 | 32 | 0.25 | >32 | 0.12 |
|  | Anti-microbial | MEM | TOB | ATM | AMK |  |  |  |
|  | MIC | <0.06 | 2 | 64 | 4 |  |  |  |
| Clinical | Anti-microbial | IPM | AMP | CAZ | GEN | LVX | CRO | PEN | TET |
| Sample | MIC | <0.12 | >32 | >32 | 1 | >8 | >64 | >16 | 4 |
| 9 | Anti-microbial | SXT | CIP | SAM | FEP | TZP | ERT | CFZ | CST |
|  | MIC (CLSI Ref) | >32 | >4 | 32 | >32 | >128 | 0.12 | 32 | 0.5 |
|  | Anti-microbial | MEM | TOB | ATM | AMK |  |  |  |
|  | MIC | <0.06 | 4 | 32 | 4 |  |  |  |
| Clinical | Anti-microbial | IPM | AMP | CAZ | GEN | LVX | CRO | PEN | TET |
| Sample | MIC | <0.12 | >32 | 0.12 | >16 | 8 | <0.12 | >16 | 4 |
| 10 | Anti-microbial | SXT | CIP | SAM | FEP | TZP | ERT | CFZ | CST |
|  | MIC (CLSI Ref) | >32 | >4 | 16 | <0.03 | 2 | 0.008 | 2 | 0.25 |
|  | Anti-microbial | MEM | TOB | ATM | AMK |  |  |  |
|  | MIC | <0.06 | 16 | <0.25 | 8 |  |  |  |
| Clinical | Anti-microbial | IPM | AMP | CAZ | GEN | LVX | CRO | PEN | TET |
| Sample | MIC | 0.25 | 4 | 0.25 | 2 | <0.06 | <0.12 | >16 | 4 |
| 11 | Anti-microbial | SXT | CIP | SAM | FEP | TZP | ERT | CFZ | CST |
|  | MIC (CLSI Ref) | <0.5 | 0.03 | 4 | <0.03 | 2 | 0.008 | 1 | 0.5 |
|  | Anti-microbial | MEM | TOB | ATM | AMK |  |  |  |
|  | MIC | <0.06 | 1 | <0.25 | 4 |  |  |  |
| Clinical | Anti-microbial | IPM | AMP | CAZ | GEN | LVX | CRO | PEN | TET |
| Sample | MIC | <0.12 | 4 | 0.12 | 1 | 0.5 | <0.12 | >16 | 4 |
| 12 | Anti-microbial | SXT | CIP | SAM | FEP | TZP | ERT | CFZ | CST |
|  | MIC (CLSI Ref) | <0.5 | 0.25 | 2 | <0.03 | 2 | 0.008 | 1 | 0.25 |
|  | Anti-microbial | MEM | TOB | ATM | AMK |  |  |  |
|  | MIC | <0.06 | 1 | <0.25 | 4 |  |  |  |
| Clinical | Anti-microbial | IPM | AMP | CAZ | GEN | LVX | CRO | PEN | TET |
| Sample | MIC | <0.12 | >32 | 0.12 | 1 | <0.06 | <0.12 | 16 | 4 |
| 13 | Anti-microbial | SXT | CIP | SAM | FEP | TZP | ERT | CFZ | CST |
|  | MIC (CLSI Ref) | <0.5 | <0.015 | >32 | <0.03 | 32 | 0.016 | 1 | 0.25 |
|  | Anti-microbial | MEM | TOB | ATM | AMK |  |  |  |
|  | MIC | <0.06 | 1 | <0.25 | 4 |  |  |  |
| BEI | Anti-microbial | IPM | AMP | CAZ | GEN | LVX | CRO | PEN | TET |
| 4.097 | MIC | <0.12 | 4 | 0.25 | 0.5 | <0.06 | <0.12 | 16 | 32 |
|  | Anti-microbial | SXT | CIP | SAM | FEP | TZP | ERT | CFZ | CST |
|  | MIC (CLSI Ref) | <0.5 | <0.015 | 8 | <0.03 | 4 | 0.008 | 2 | 0.12 |
|  | Anti-microbial | MEM | TOB | ATM | AMK |  |  |  |
|  | MIC | <0.06 | 1 | <0.25 | 4 |  |  |  |

Example 2: Checkpoint Assays can be Used to Ascertain Sufficient Microorganism Growth This example shows that checkpoint assays can ascertain microorganism growth.

Growth Indicators can Inhibit Microorganism Growth During Incubation

Bacteria were inoculated into 96-well microplates comprise cation-adjusted Mueller Hinton broth in the presence and absence of resazurin (alamarBlue®) and incubated at 35° C. for 4 hours. For wells that were not incubated with resazurin, the growth indicator was added immediately after the 4-hour incubation. BacTiter-Glo reagent (Promega, Madison, WI) was added to all wells and luminescence was measured. If bacteria were incubated in the presence of resazurin, less luminescent signal was observed upon addition of BacTiter-Glo® than in wells where bacterial were not incubated in the presence of resazurin, indicating fewer viable bacteria present. FIG. 1 shows that although resazurin can speed the time to AST results when included in the wells during incubation, it can have an inhibitory effects on microbe growth. Thus, it can be advantageous to remove growth indicator from test wells during incubation.

Figure 2:
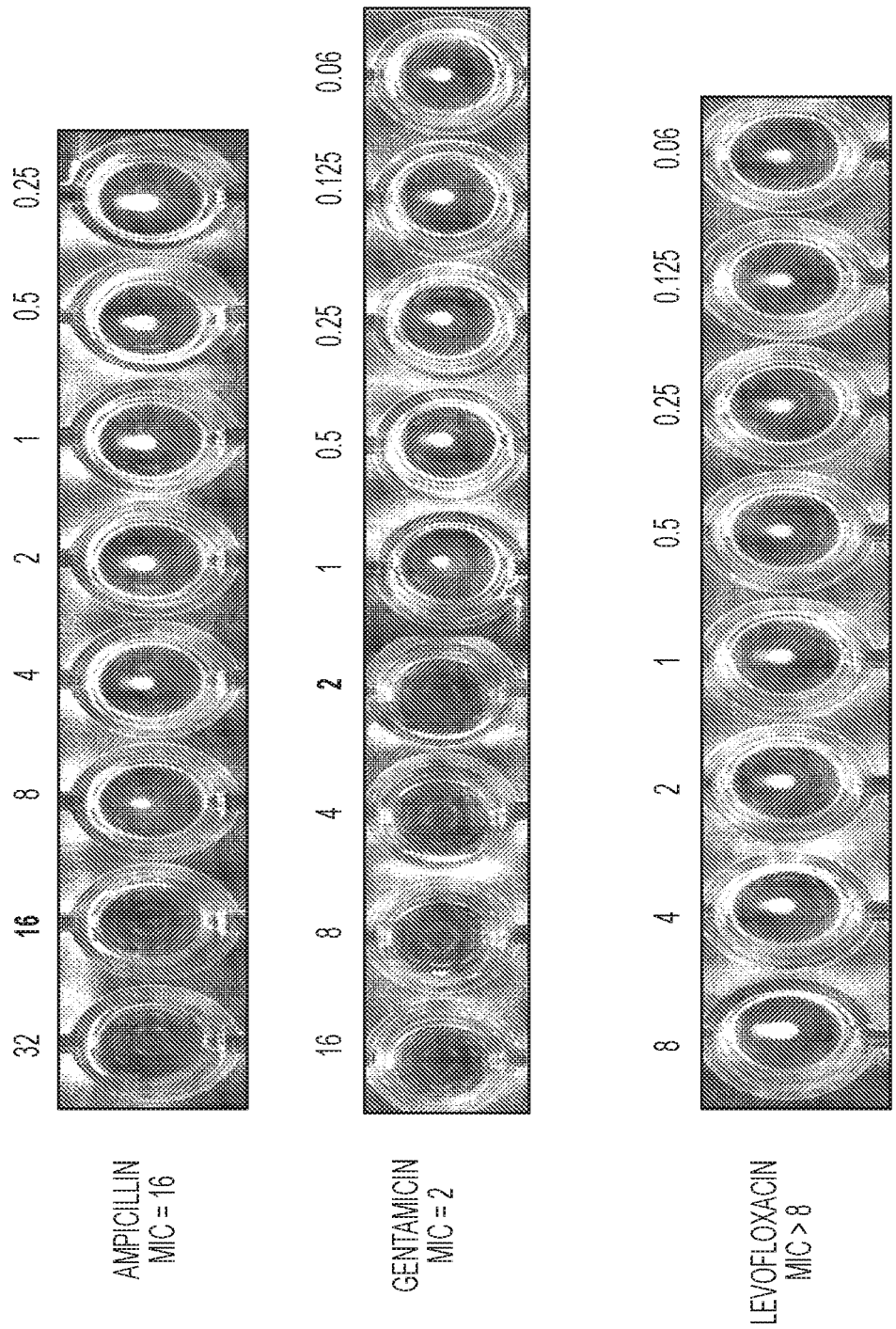
FIG. 2 depicts photos from using the Clinical and Laboratory Standards Institute (CLSI) overnight reference method for broth microdilution AST and its MIC determinations for a slow-growing clinical *S. aureus* strain in the presence of Ampicillin, Gentamicin, and Levofloxacin. The minimum inhibitory concentration (MIC) is the lowest dilution of a particular antibiotic with no visible bacterial growth.

Endpoint Measurements for AST Results are Limited Due to Slow-Growing Bacteria Strains FIG. 2 depicts photos from the CLSI overnight reference method for broth microdilution AST results for a slow-growing clinical S. aureus strain in the presence of Ampicillin, Gentamicin, and Levofloxacin, where the MIC is called as the lowest dilution of a particular antibiotic with no visible bacterial growth. This is how the MICs would be called if the assay was allowed to run overnight.

Figure 3:
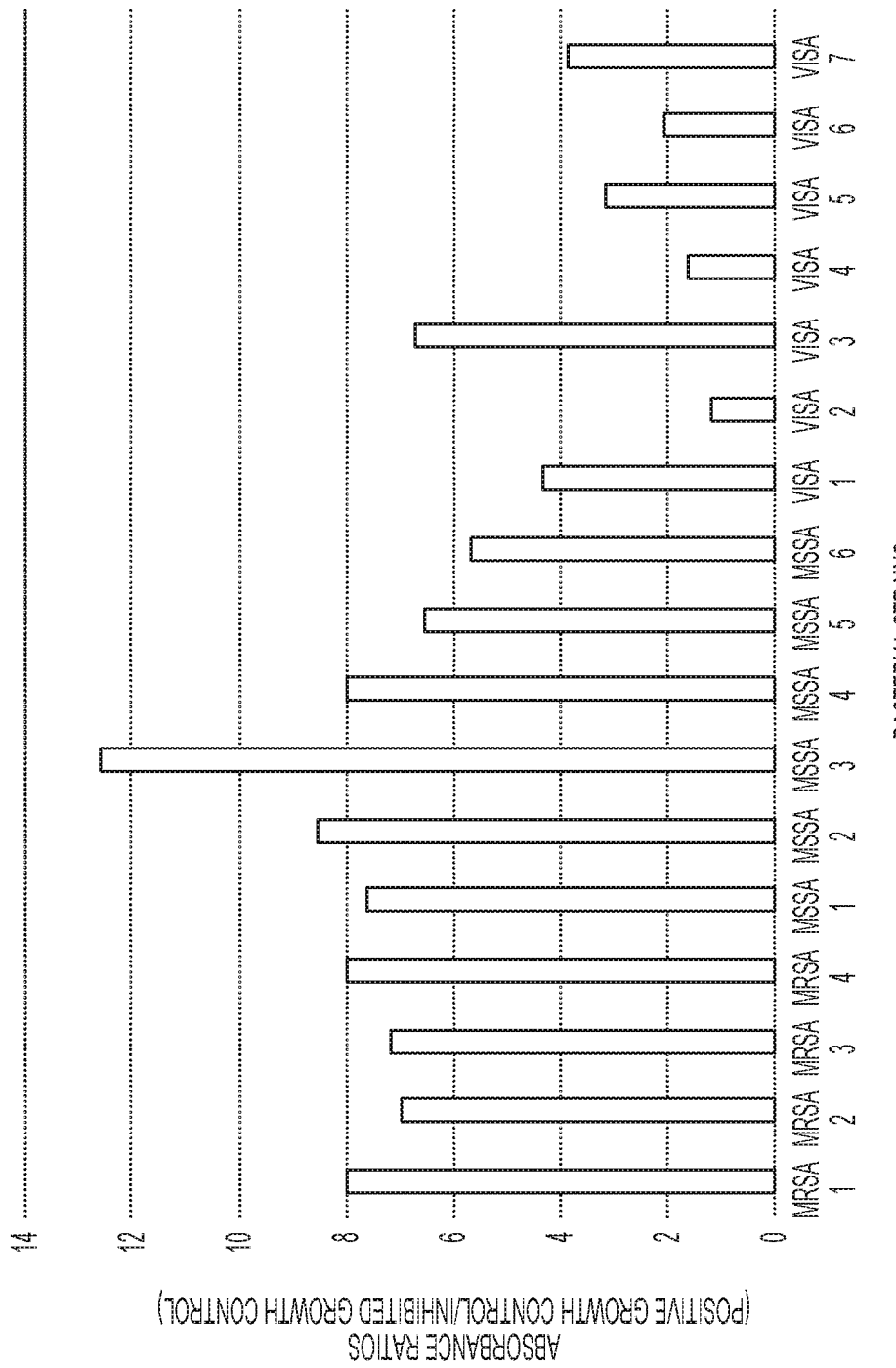
FIG. 3 depicts a graph in which a surface-binding assay was performed upon a variety of clinical *S. aureus* bacterial strains (including a slow-growing strain) and the absorbance ratios of positive growth wells to inhibited growth control wells were measured.

FIG. 3 depicts the differences in growth rates among various clinical S. aureus bacterial strains, including the slow-growing S. aureus strain. Using 96-well microplates comprising cation-adjusted Mueller Hinton broth, bacteria were prepared by diluting colonies into saline to reach a McFarland value of 0.5, which was verified using a spectrophotometer. This was diluted 1:20 into saline and 10 μl of inoculum was added to each well. Inoculated plates were incubated at 35° C., shaking at 150 rpm for 3 hours and 45 minutes. After this incubation, cationic magnetic beads and anti-S. aureus antibodies (conjugated to horseradish peroxidase) were added to each well and incubated for 20 minutes. Using an automated plate washer, magnetic beads were captured and the contents of each well were washed three times with PBS-Tween20 (0.1%). TMB was added and allowed to incubate for 15 minutes, after which the reaction was stopped by addition of 1 M sulfuric acid. Absorbance at 450 nm was measured for each well. The data in FIG. 3 shows ratios of absorbance signal from positive growth wells to absorbance measured in inhibited growth (nutrient-free) wells were measured. Any signal ratio >1 indicates bacterial growth has occurred and larger numbers indicate more bacterial growth has occurred.

Such slow growth can produce erroneous or incomplete results because microbes have not had sufficient time to grow, and therefore, their response to antimicrobials cannot be effectively assessed. This problem can be particularly acute for assays that are destructive of microbes because further tests cannot be performed.

Checkpoint Growth Assay can Ascertain Sufficient Microorganism Growth

Figure 4:
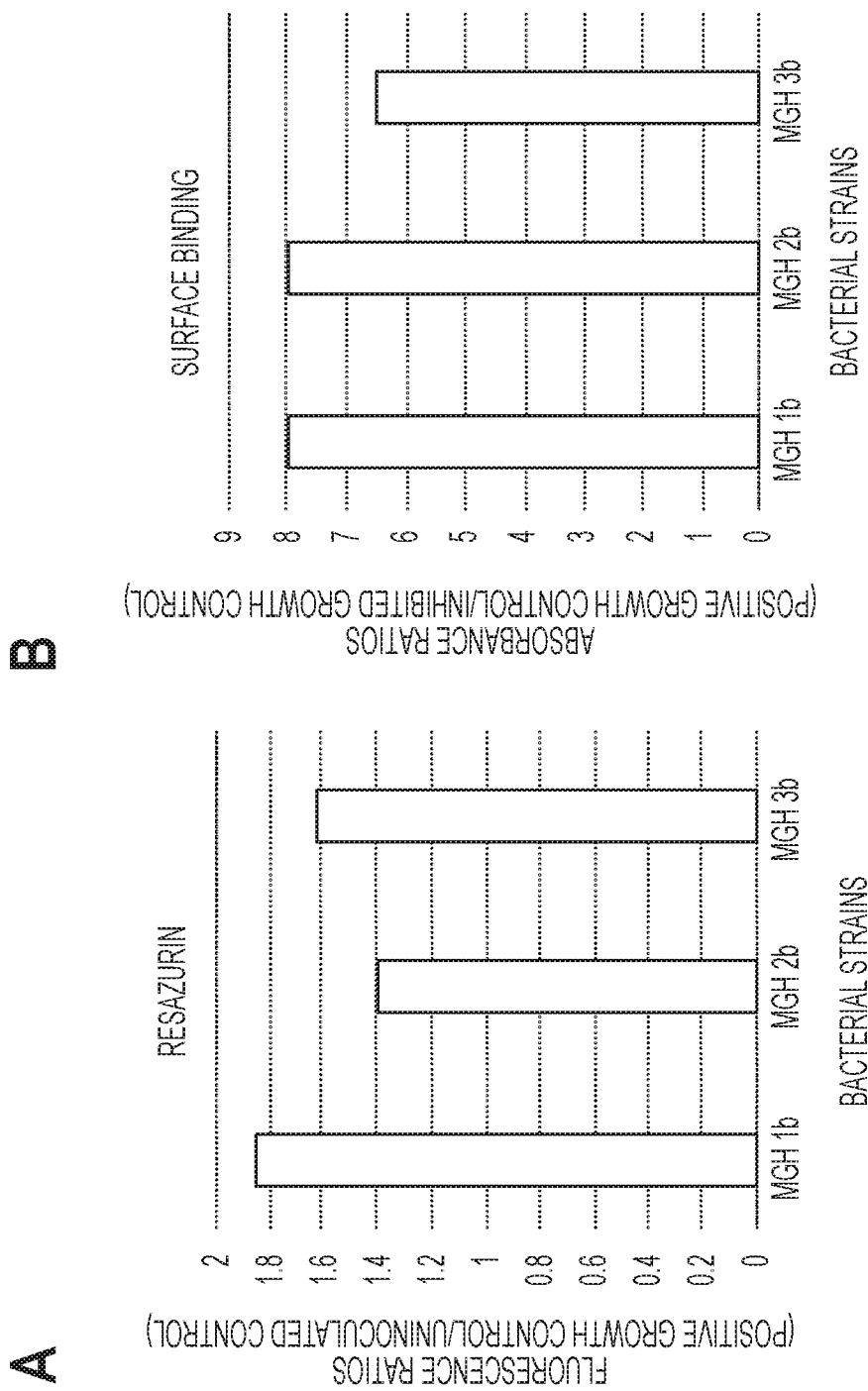
FIGS. 4A and 4B show fluorescence ratios of signal from positive growth wells to uninoculated controls or inhibited growth control wells for a checkpoint assay using a resazurin growth indicator (FIG. 4A) and a surface-binding probe assay (FIG. 4B).

FIGS. 4A and 4B show that a growth indicator provides a measurable signal from the checkpoint test wells that can be used as a proxy for growth measured by an endpoint assay. Using 96-well plates comprising cation-adjusted Mueller Hinton broth, bacteria were prepared by diluting colonies into saline to reach a McFarland value of 0.5, which was verified using a spectrophotometer. This was diluted 1:20 into saline and 10 µl of inoculum was added to each well. The growth indicator resazurin was added to predetermined checkpoint assay wells. Inoculated plates were incubated at 35° C., shaking at 150 rpm for 3 hours and 45 minutes. After this incubation, fluorescence (Excitation 560/Emission 590 nm) was measured from wells comprising resazurin. The data in FIG. 4A (resazurin) is represented as the ratio of fluorescence measured in positive growth control wells to fluorescence measured in uninoculated wells. Any signal ratio >1 indicates bacterial growth has occurred. The positive growth threshold control well comprised growth broth and microbes and a growth indicator but no antimicrobial. FIG. 4B (surface-binding) depicts bacterial quantification by surface binding, where cationic magnetic beads and anti-S. aureus antibodies (conjugated to horseradish peroxidase) were added to each well and incubated for 20 minutes. Using an automated plate washer, magnetic beads were captured and the contents of each well were washed three times with PBS-Tween20 (0.1%). TMB was added and allowed to incubate for 15 minutes, after which the reaction was stopped by addition of 1 M sulfuric acid and absorbance at 450 nm was measured for each well. The data in FIG. 4B is represented as the ratio of absorbance measured in positive growth checkpoint wells to absorbance measured in inhibited growth (nutrient-free) wells. Any signal ratio >1 indicates bacterial growth has occurred.

Figure 5:
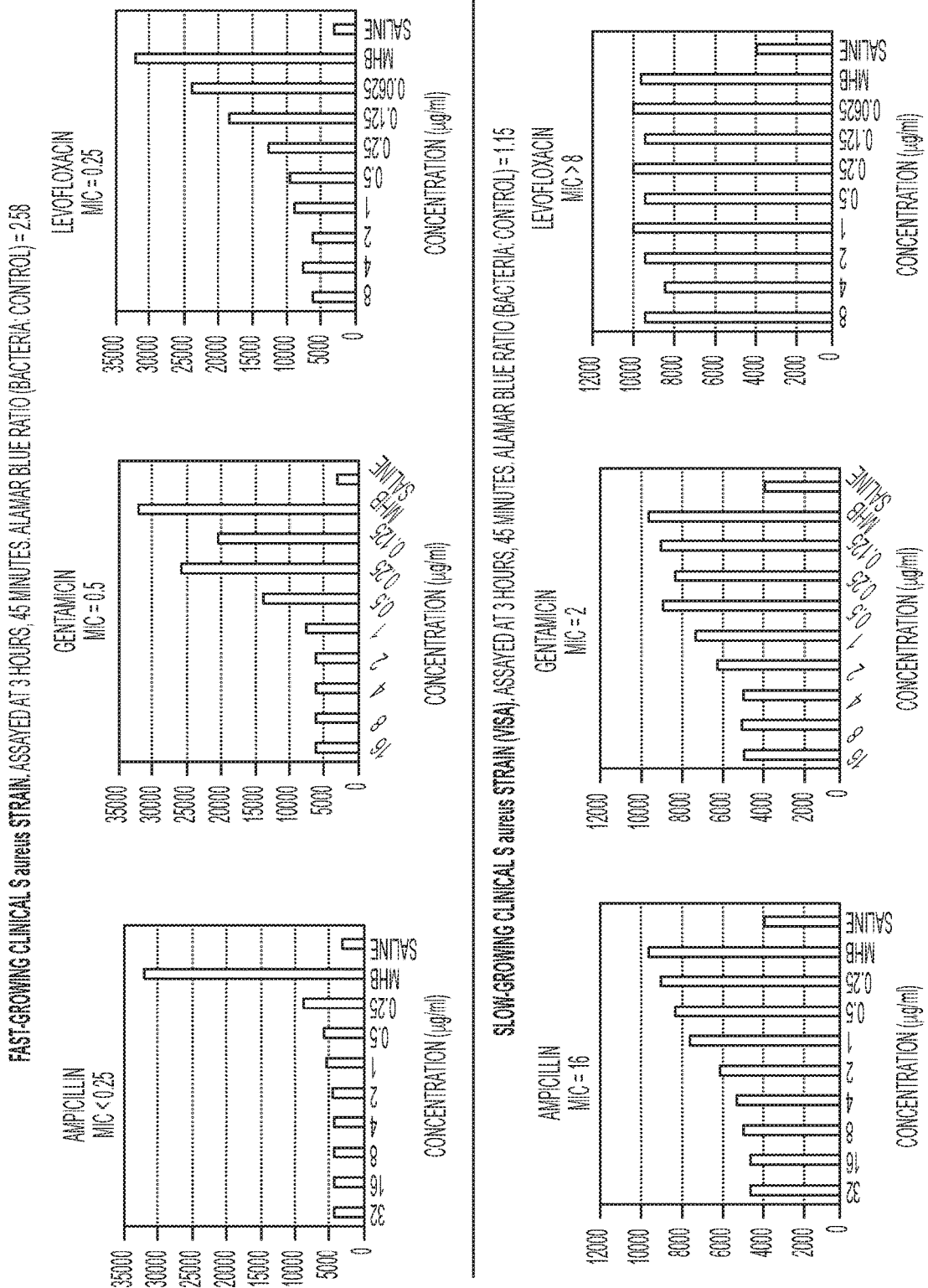
FIG. 5 shows graphs resulting from AST assays for both fast-growing and slow-growing clinical *S. aureus* strains in the presence of ampicillin, gentamicin, and levofloxacin.

FIG. 5 demonstrates checkpoint assay results for both fast-growing and slow-growing clinical S. aureus strains and the impact on resulting AST determinations. A ratio of alamarBlue® (resazurin) signal in an inoculated well to an uninoculated well was used as a growth checkpoint to determine if the AST assay was ready to be processed.

As shown in FIG. 5, the slow-growing S. aureus strain did not produce discernable MIC determinations from an AST assay that was performed following a 3 hour, 45 minute incubation period. Rapid AST was performed with two S. aureus strains at 3 hours, 45 minutes after inoculation. During this time, one well for each strain was inoculated as a "checkpoint well" and included alamarBlue® (a growth indicator that acts as a measure of cell growth). The fast-growing strain showed an alamarBlue® signal ratio of an inoculated sample to an uninoculated sample of 2.58. The slow-growing strain showed an alamarBlue® signal ratio of 1.15. The fast-growing S. aureus strain with a higher growth checkpoint ratio (alamarBlue® ratio (bacteria:control)= 2.58) before processing gave much more definitive MIC data in the processed AST assay, whereas the slow-growing strain had a low growth checkpoint ratio (alamarBlue® ratio (bacteria:control)=1.15) and yielded less decisive MIC data. The indiscernible MIC data of the slow-growing S. aureus strain shows that this sample would not be approved at the checkpoint phase to continue to AST processing and would instead be placed back in the incubator for a further incubation period.

Figure 6:
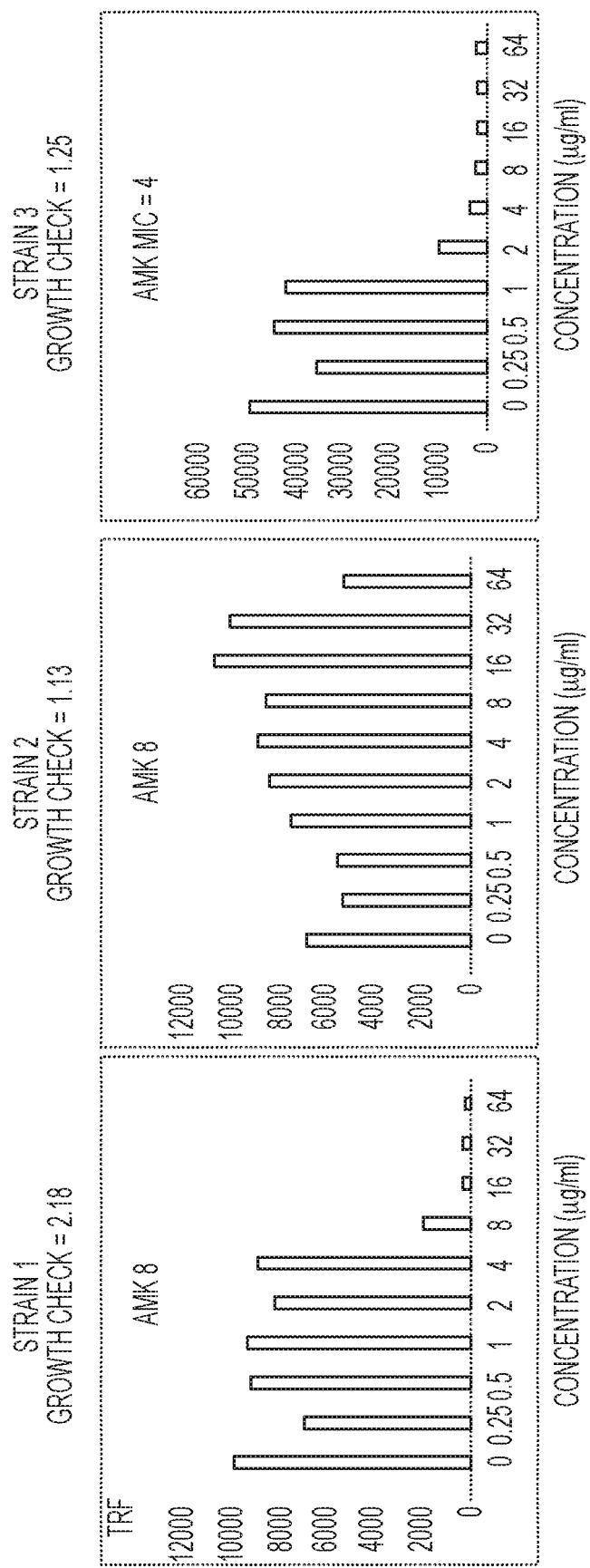
FIG. 6 shows MIC data from AST assays by time resolved fluorescence (TRF) with europium probe for three different strains of *P. aeruginosa*. The x-axis of each graph denotes the concentrations of antimicrobial Amikacin (AMK) in micrograms/milliliter, and the y-axis denotes fluorescence from binding to bacteria surface. Growth check data measured by optical density (Absorbance at 600 nm) of the bacterial culture is denoted for each strain. The figure shows that reliability of MIC results depends on optimum growth of the bacteria.

FIG. 6 demonstrates similar outcomes using three strains of P. aeruginosa as exemplary bacteria, that AST tests showed improved and decisive MIC data when the tests were performed at the time the bacteria attained a certain growth check ratio value. AST was performed by surface binding of probe followed by time resolved fluorescence. The P. aeruginosa strains were incubated at 35° C. in shaking conditions for 4 hours for attaining growth, and growth check was performed by measuring absorbance of the culture at 600 nm after 4 hours of growth. At growth checkpoint value of 1.13, Strain 2 did not demonstrate a reliable MIC data with Amikacin (AMK) which is expected to be 8. At higher growth check value of 2.18, Strain 1, on the other hand exhibited a reliable MIC of 8. Similarly Strain 3 demonstrated reliability at the growth check value of 1.25.

Figure 7:
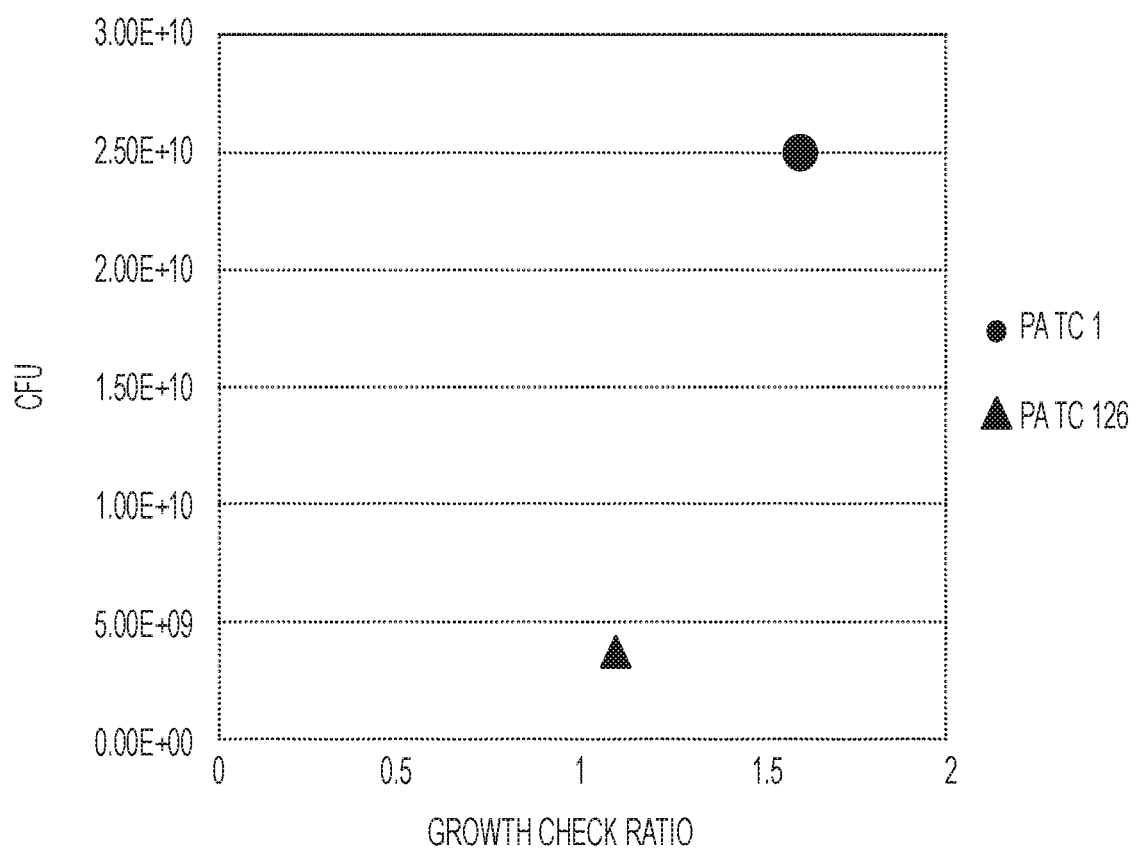
FIG. 7 shows plot of growth check ratio versus bacterial colony forming assay data for two strains of *P. aeruginosa*. The data shows correlation of growth checkpoint data obtained by measuring the optical density at 600 nm expressed as a ratio of absorbance between inoculated versus uninoculated wells on a cartridge; with that of bacterial colony forming assay. The x-axis denotes growth checkpoint data and the y-axis denotes colony forming assay data in colony forming units (CFU).

FIG. 7 demonstrates that with two strains of P. aeruginosa that the growth check ratio values obtained using optical density measurements are in concurrence with CFU values, where, the strain with higher growth check ratio value had higher CFU value. Two strains of P. aeruginosa were inoculated in 100 □l of MHB and allowed to grow at 35° C. in shaking conditions for 4 hours. The ratio of the optical density (OD) of the bacterial culture at 600 nm wavelength of inoculated wells over uninoculated wells was determined. Serial dilution of the culture was performed and 100l of each suitable dilution were plated on an agar plate and incubated overnight. Colonies formed were counted the following day and the colony forming units (CFUs) of the bacteria per well were calculated based on the dilutions plated. As shown in the figure, an agreement of the two methods was observed.

Although growth indicators can suppress microbial growth, they can serve as a proxy for uninhibited growth through their incorporation in a growth threshold checkpoint well during microbial incubation.

Upon Determination of Sufficient Growth, AST Result can be Determined

Surface-Binding Amplification Assay

Figure 8:
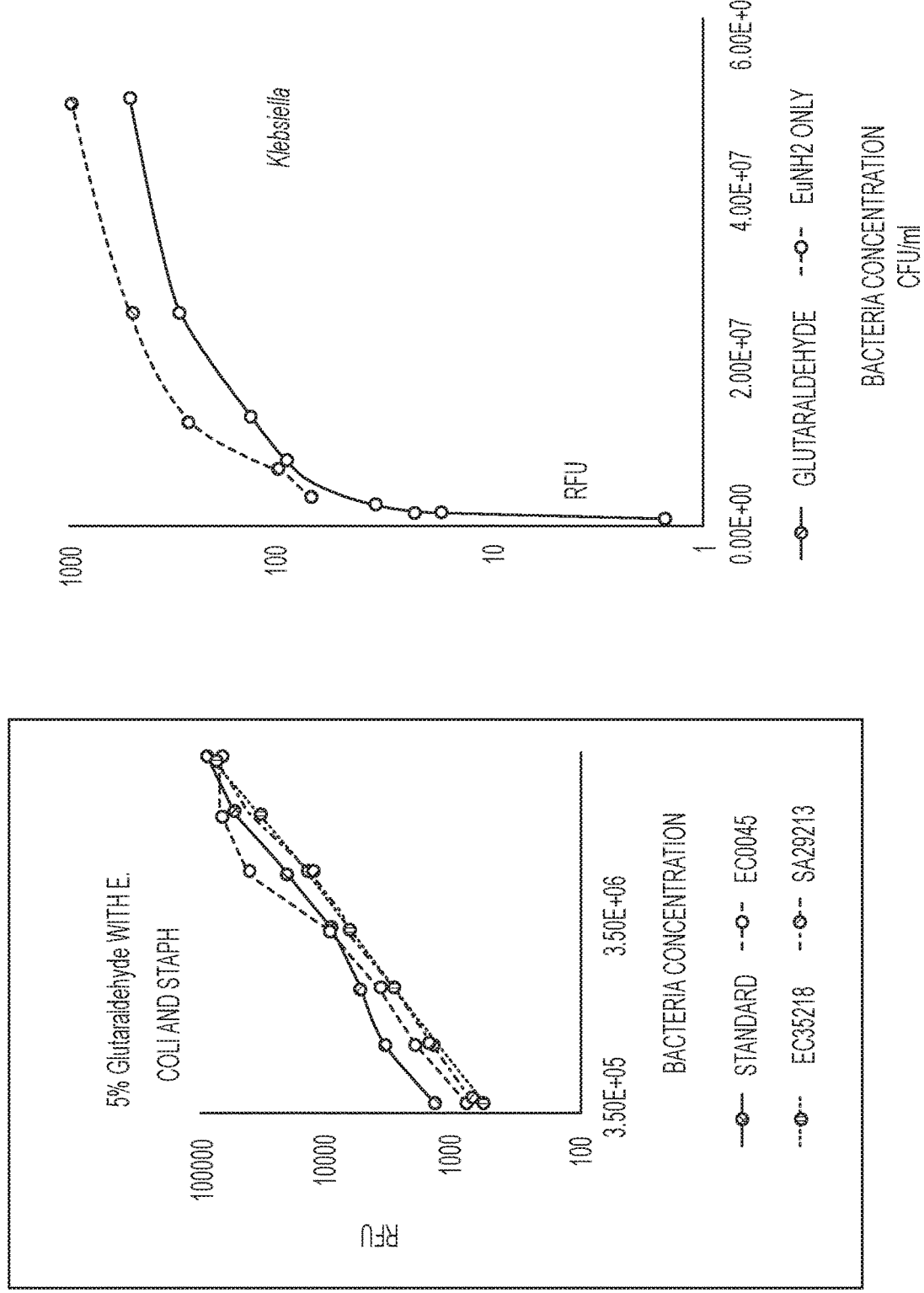
FIG. 8 shows a graph with the results from a surface-binding amplification assay using a europium cryptate molecule to label and quantify microorganisms (*E. coli* on the left and *Klebsiella pneumoniae*, on the right) and measurement of relative fluorescence units (RFU).

A surface-binding amplification assay using a europium cryptate molecule to label and quantify microorganisms can be utilized to determine AST results, as demonstrated in FIG. 8. E. coli and S. aureus (left panel) or Klebsiella pneumoniae (right panel) were inoculated across a 96-well microplate in concentrations ranging from 1e5 to 1e9 in MES buffer at pH 6. To each well comprising the bacteria, and to the corresponding control wells, europium cryptate-diamine (Cisbio) was added at 66 ng/well, then a 5% solution of glutaraldehyde was added to wells comprising europium cryptate. The reaction solution was allowed to incubate for 30 minutes in order to facilitate the labeling of the exterior of the bacteria within the well with the chosen reporter. Then, the test plate was centrifuged, using a Thermo Scientific Heraeus Multifuge X3, at a speed of 2500 rpm for 2.5 minutes in order to pellet the bacteria in the bottom of the plate while leaving any unassociated reporter in the supernatant. The plate was then aspirated, using a BioTek Multiflo X plate washer, to remove the supernatant and unreacted reporter, before the addition of a wash buffer. This wash procedure was repeated once to thoroughly remove any unreacted reporter. Wells comprising EuropiumCryptate-diamine were reconstituted in reading buffer and read using time resolved fluorescence on a BioTek H1 plate reader.

Metabolic Probe Assay

Figure 9:
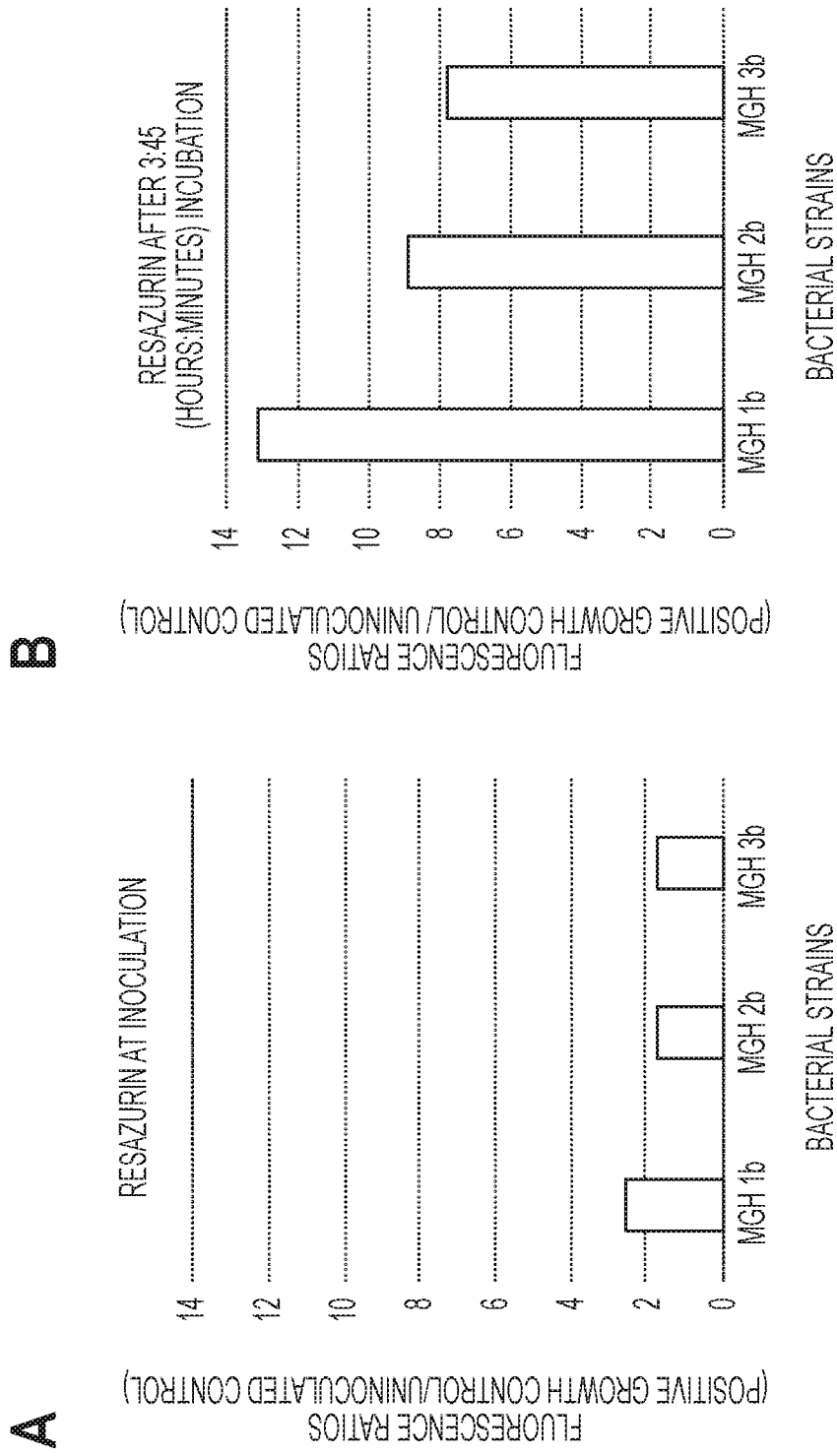
FIGS. 9A and 9B show graphs where fluorescence ratios were measured in bacteria samples following an incubation period. In one sample (FIG. 9A), resazurin was added at the beginning of the incubation period, and in the other sample (FIG. 9B), resazurin was added after the incubation period.

FIGS. 9A and 9B shows that a metabolic probe can be utilized to determine AST results when the metabolic probe is added to additional wells on the microplate only after the growth threshold determining sufficient microorganism growth has been reached. This enables the advantages of growth indicators without their drawbacks: signals arise predominantly from live microorganisms but the growth inhibitory and toxic effects are eliminated from the initial incubation period. Using 96-well plates comprising cation-adjusted Mueller Hinton broth, bacteria were prepared by diluting colonies into saline to reach a McFarland value of 0.5, which was verified using a spectrophotometer. This was diluted 1:20 into saline and 10 µl of inoculum was added to each well. The indicator resazurin was added to specific wells, either at the time of inoculation or after 3 hours and 45 minutes. Inoculated plates were incubated at 35° C., shaking at 150 rpm for 4 hours and 45 minutes. After this incubation, fluorescence (Ex560/Em590) was measured from wells comprising resazurin. The data in FIG. 9A and FIG. 9B is represented as the ratio of fluorescence measured in positive growth control wells to fluorescence measured in uninoculated wells. The ratio of fluorescent signal in inoculated wells to uninoculated wells was much greater if resazurin was added after an initial bacterial incubation.

Example 3: Preheating Cartridges Prior to Incubation

This example depicts preheating cartridges utilizing infrared radiative heating. The experimental setup for the infrared preheater consists of an off-the shelf heating apparatus from VJ Electronix (VJ IR-1C) and custom fixturing for holding 96-well microplates. The thermal data collection was performed by a National Instruments CompactDAQ Chassis, National Instruments Resistance Temperature Device (RTD) analog module (NI 9216), and up to 8 sealed RTDs (Omega, HSRTD-3-100-A-40-E).

RTDs were inserted into the desired wells for measurement through a ⅛" hole drilled through the microplate lid, and taped to keep the RTD tip submerged in the 100 µL of liquid that was present within each well. The plates, lids, and volumes were similar to those used for standard broth microdilution tests with the exception of the through holes drilled in the lid through which the RTDs are inserted. This experimental adaptation was necessary in order to record temperatures in real-time.

A desired preheat temperature was set on the IR-1C preheater and the four heaters were turned on. In order for the IR-1C to accurately monitor its own temperature, and thus accurately maintain its set temperature, a K-type thermocouple was installed and fixed just above the heating plate.

Once the heater was at temperature, the test microplate was placed within a spring-loaded holder. This fixture held the plate level ~2 cm above the heating mantle. The fixture was designed to tightly hold the microplate so it did not move during the preheat step.

Figure 10:
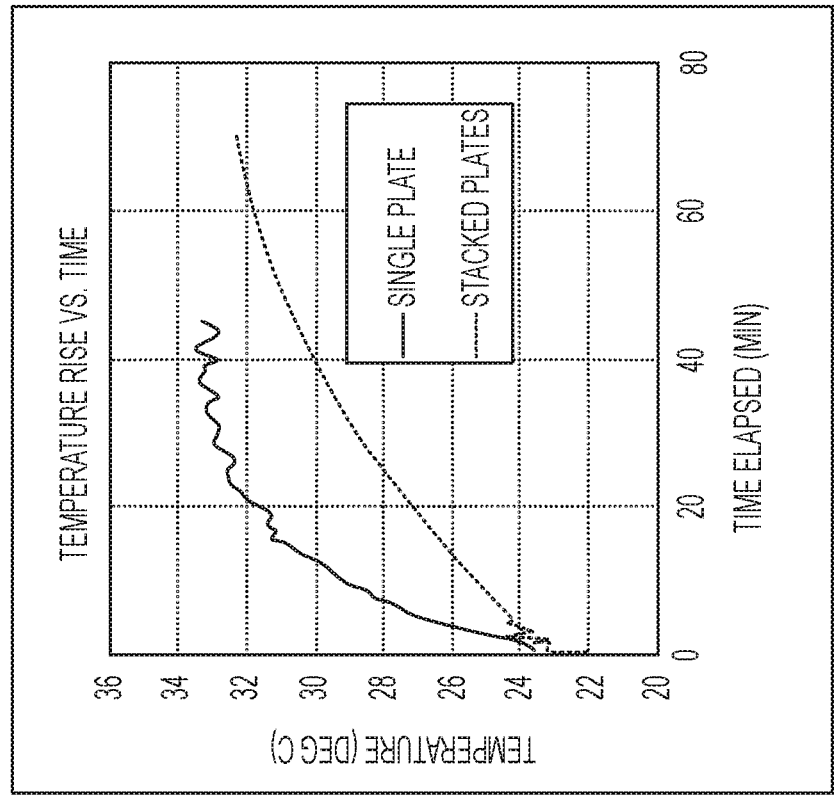
FIGS. 10A and 10B shows two graphs in which temperatures of 96-well microplates were measured over time while being preheated either by radiative heating or convectionally.
Figure 10:
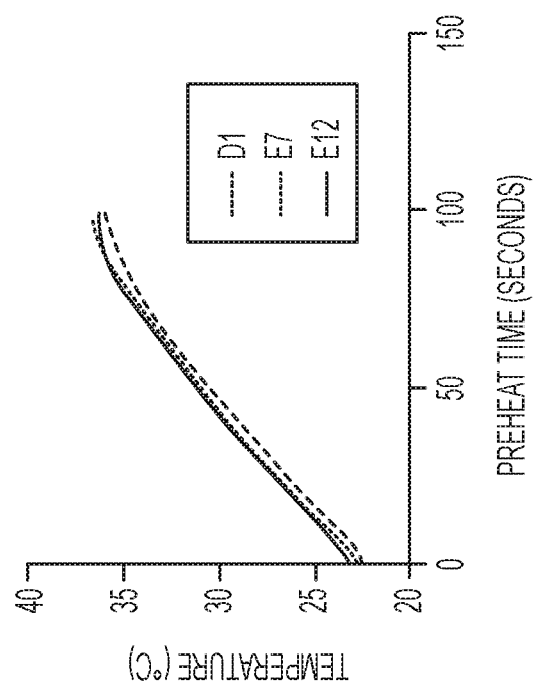

The data in FIG. 10A show the rate and uniformity of heating. After <2 minutes of heating, the solutions present within measured wells reached a temperature of 35±1° C. The 96-well plate format has 8 rows labeled "A" through "H" and 12 columns labeled "1" through "12." The thermal data of the three points in FIG. 10A represent two opposite edge wells as well as a central well.

Figure 11:
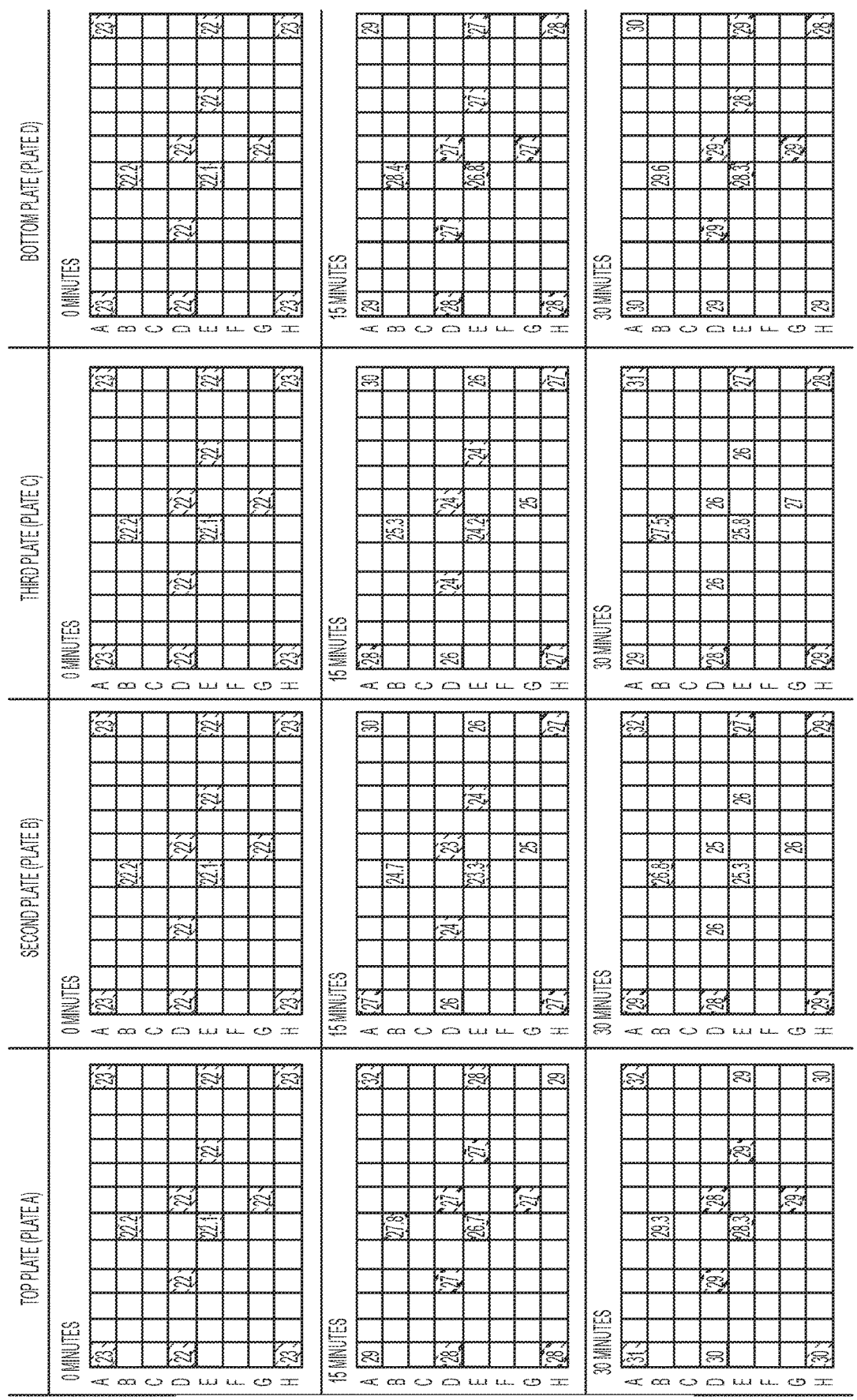
FIG. 11 shows well solution temperature data for a 4-plate stack of 96-well microplates.

In comparison, a standard convection incubator can require 20-30 minutes to heat all wells of a 96-well plate from 25° C. to 35° C. The data in FIG. 10B were obtained with the same temperature acquisition hardware and utilized a Southwest Scientific IncuShaker Mini with microplate adapter. Stacking plates in such an incubator can further lead to nonuniform heating, as shown by the data in FIG. 11. Since microorganism growth rates increase with increasing temperature in this range, a 2-minute rise-to-temperature affords a longer growth period than a 30-minute rise-to-temperature. This is advantageous for shortening the time of assays, such as AST, that are based on microorganism growth. Additionally, the uniformity of the heating can be important for accuracy. Preheating therefore promotes suitable bacterial growth within the time of incubation for performing the AST assays by the method described herein. Preheating can further enable subsequent stacking in convection incubators.

Figure 12:
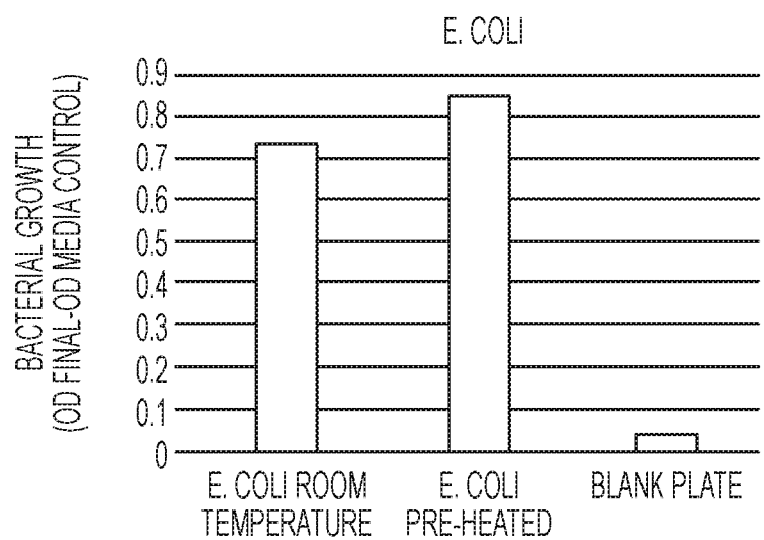
FIGS. 12A and 12B depicts effect of preheating plates on bacterial growth determined by measuring optical density at the end of incubation.
Figure 12:
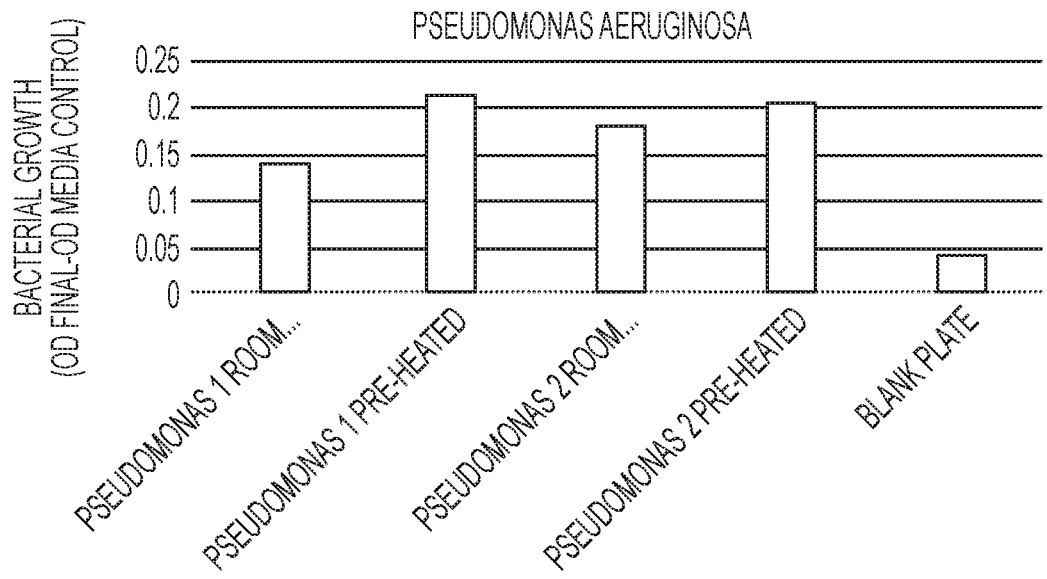

FIGS. 12A and 12B show improvement of bacterial growth with preheating the plates for two exemplary bacterial species *E. coli* and *P. aeruginosa* respectively. Plates were either preheated for 30 minutes, or left at room temperature. For FIG. 12A, *E. coli* was grown by known bacterial culture methods on the 384 well-plates and an absorbance (optical density, OD) value was determined at 600 nm and the value of the same for uninoculated control wells was subtracted to obtain the resultant OD value depicting bacterial growth. In case of FIG. 12B, two strains of *P. aeruginosa* were inoculated in 40 □l of cation-adjusted MHB in either preheated 384 well plates or identical plates left at room temperature. Bacterial growth in plates with or without preheating is depicted in the graph, showing OD values determined by absorbance at 600 nm, after subtracting a background value of a well with no bacterial inoculum. The results show that 30 minutes of preheating of the plates provide favorable or optimal rise in growth of bacteria when incubated for short period of 2-4 hours which favors one of the objectives of the present method, the reduction of overall time of performance of the antimicrobial susceptibility assay.

Example 4: Agitating Cartridges During Incubation

Figure 13:
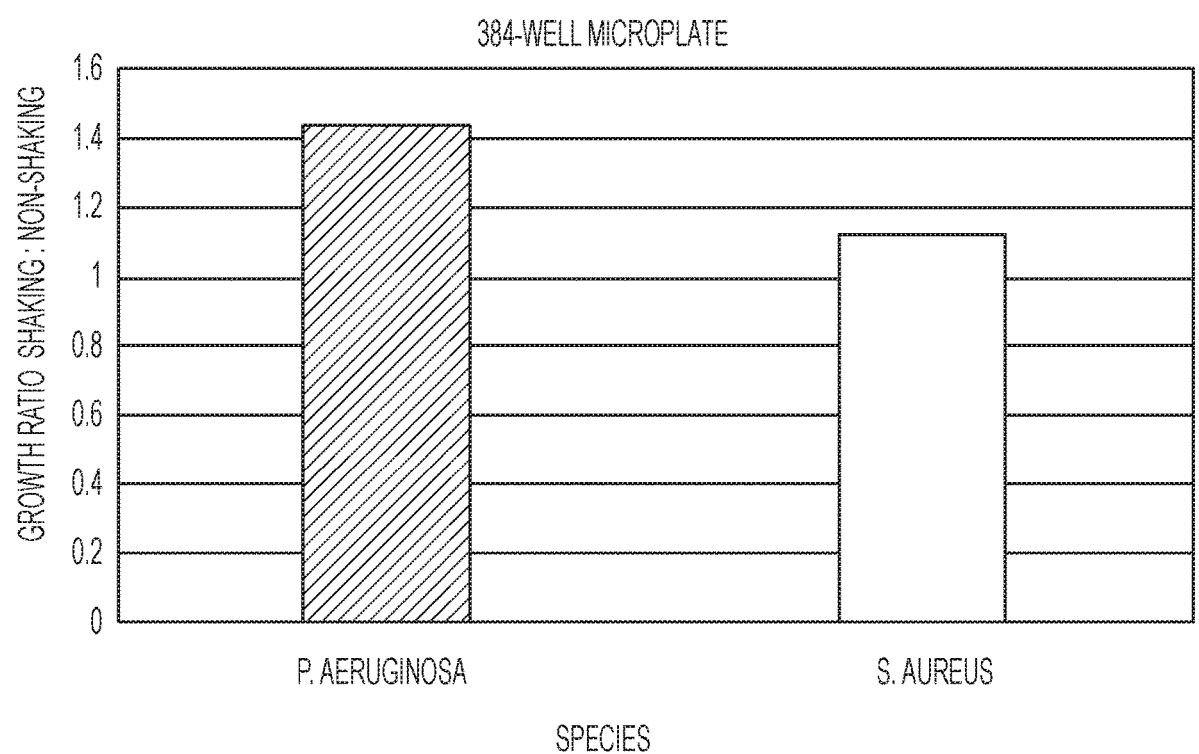
FIG. 13 depicts the growth ratio for the microorganism growth as determined by optical density measurement at 600 nm for a 384-well microplate under shaking versus non-shaking conditions for two bacterial strains. In one case, the 384-well microplate was incubated with shaking at 150 rpm and at a radius of 25 mm, in a second case, an identically inoculated microplate was held static during the incubation.
Figure 14:
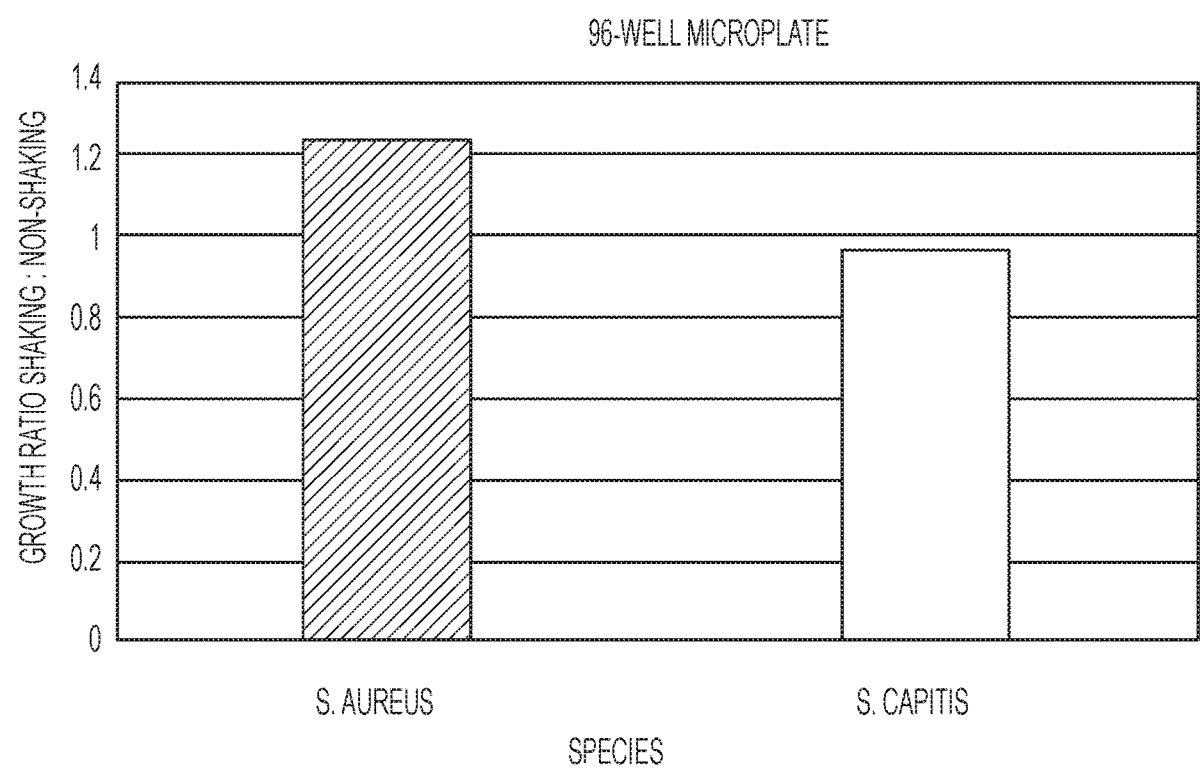
FIG. 14 depicts the growth ratio for the microorganism growth as determined by optical density measurement at 600 nm for a 96-well microplate held static during the incubation, compared to an identically-inoculated 96-well microplate incubated with shaking at 150 rpm and at a radius of 25 mm.

Dilutions of two representative microorganisms, *P. aeruginosa* and *S. aureus*, were introduced to two standard 384-well microplates, and one microplate was placed in an incubator that induced orbital shaking (i.e., agitating) at a frequency of 150 rpm and a radius of 25 mm. The other microplate was placed in an incubator and held static. After 3 hours, the microorganism growth was determined by optical density measurement at 600 nm. FIG. 13 depicts the enhanced growth ratios of the representative microorganisms incubated under these conditions. The growth ratio is the microorganism growth as determined by optical density measurement at 600 nm for a 384-well microplate held static during the incubation, compared to an identically-inoculated 384-well microplate incubated with shaking at 150 rpm and at a radius of 25 mm. FIG. 14 shows that similar growth enhancement was achieved in a 96-well microplate.

By agitating incubating AST microplates with wells with lateral dimensions <12 mm at shaking frequencies and radii insufficient to provide solution mixing, enhanced growth rates of microorganisms were achieved.

Figure 15:
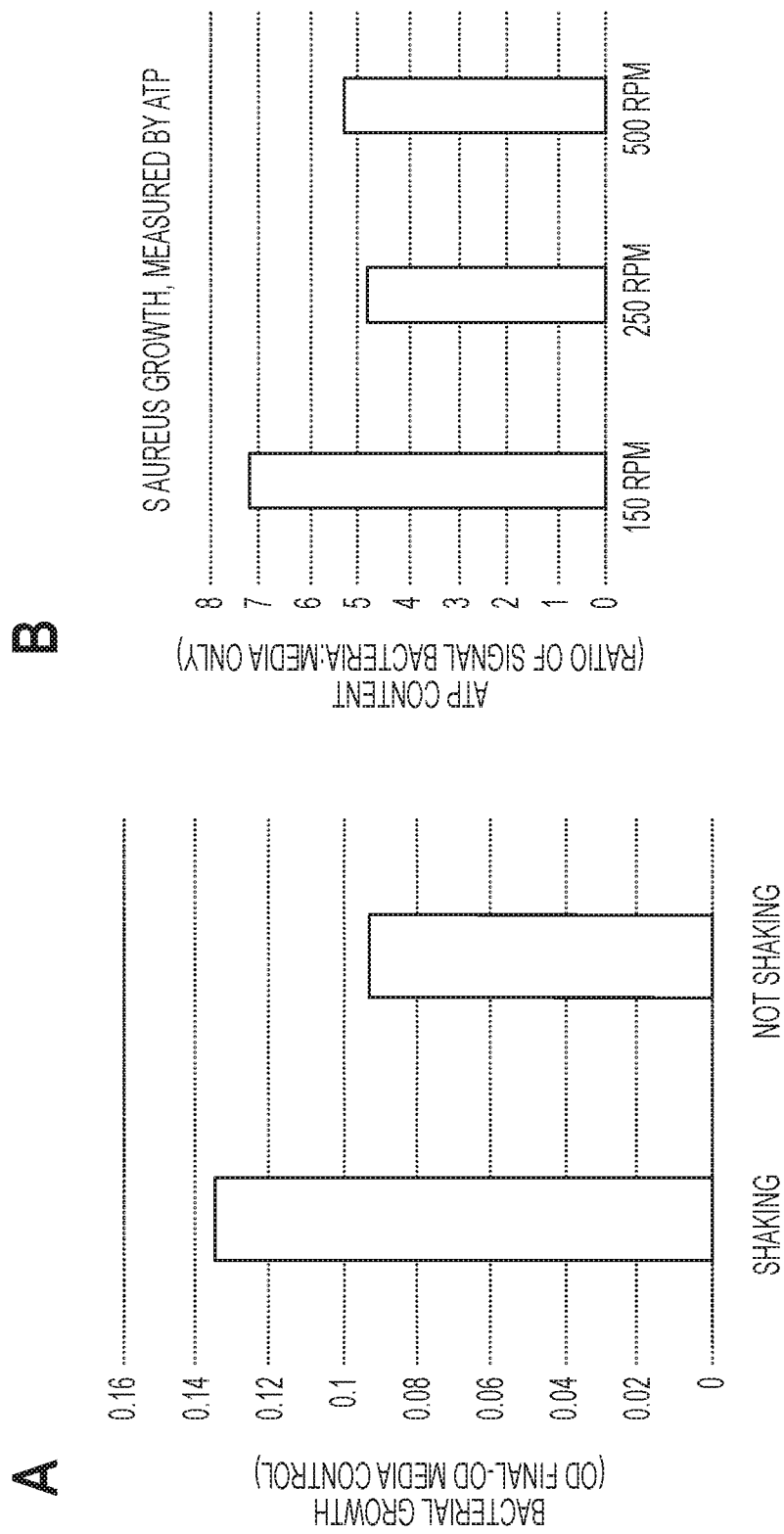
FIGS. 15A and 15B shows effect of plate agitation (shaking) during incubation on microbial growth.

FIG. 15A provides a direct side by side comparison of bacterial growth by measuring OD values of *S. aureus* cultures in presence of absence of orbital shaking. The bacteria were incubated in 384 well plates under identical conditions except for the agitation, and absorbance of the culture was determined by measuring OD at 600 nm after 4 hours of growth. FIG. 15B shows *S. aureus* growth indicated by measuring the relative ATP levels in the culture, while identical cultures were subjected to shaking speed of 150 rpm, 250 rpm and 500 rpm respectively. In this study, the bacteria were inoculated into 40 □l of Cation adjusted MHB in 384 well plates. The bacteria were incubated at 35° C. for 2 hours under shaking at indicated speeds. Bactiter Glo which is an agent capable of producing a luminescent signal in presence of ATP is added to the wells following the incubation of 2 hours. The intensity of the signal is proportional to the amount of live bacteria in the culture solution and therefore is indicative of the growth. This data showed that a shaking speed that is mild to moderate is best suited for the growth of these bacteria under the given conditions which would enable better AST results.

Example 5: Use of Tetrazolium Analogues for Determination of Microorganism Viability This example shows that tetrazolium-based molecules can be used as metabolic probes and growth indicators in the determination of microorganism viability. These molecules can be utilized to determine AST results (1) in a metabolic probe assay that is run with a surface binding assay sharing the same incubation period and/or (2) when the metabolic probe is added to additional wells on the microplate only after the growth threshold determining sufficient microorganism growth has been reached.

Figure 16:
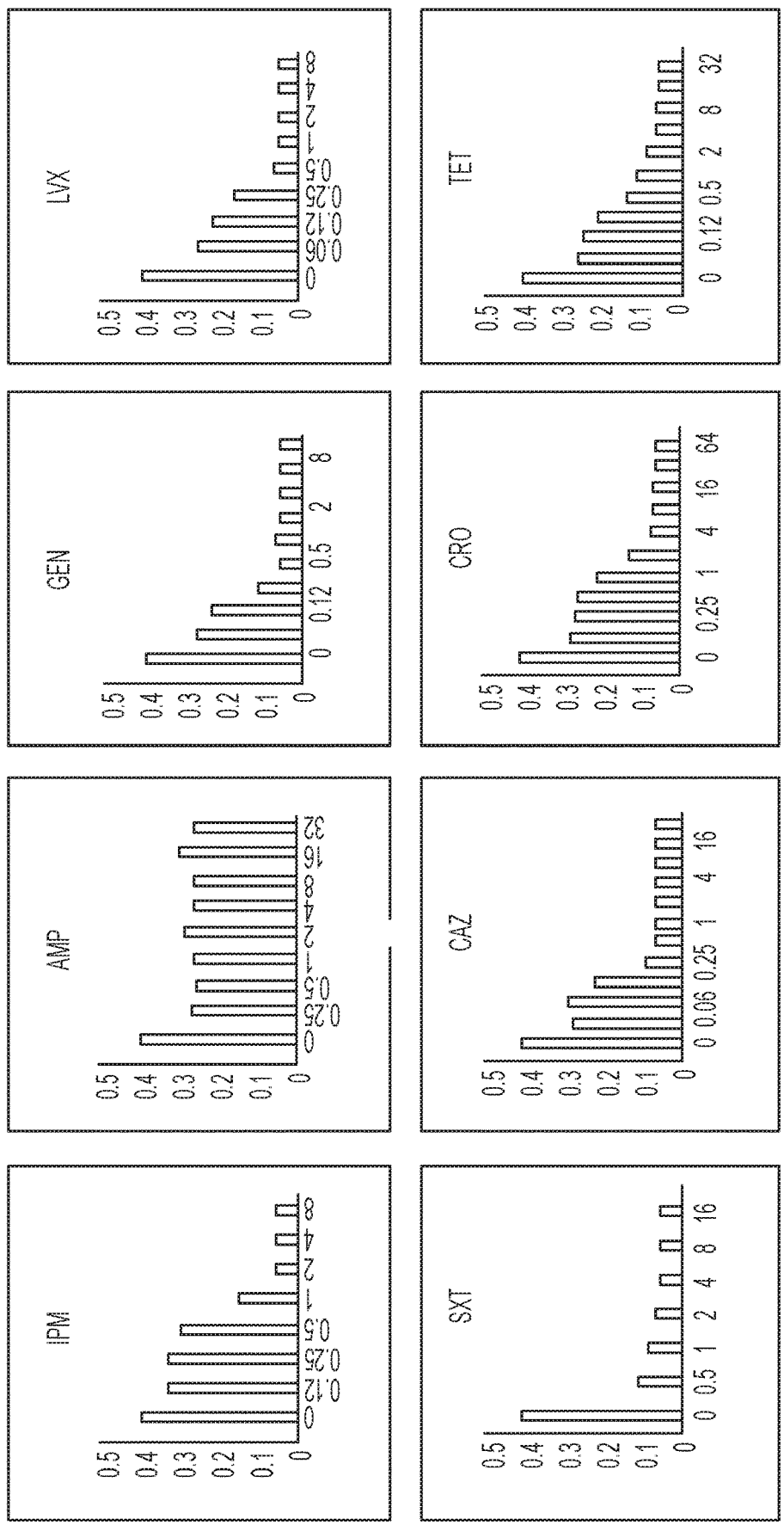
FIG. 16 shows AST results when the metabolic probe INT was tested with *Pseudomonas aeruginosa* on a single plate with multiple antimicrobials.
Figure 17:
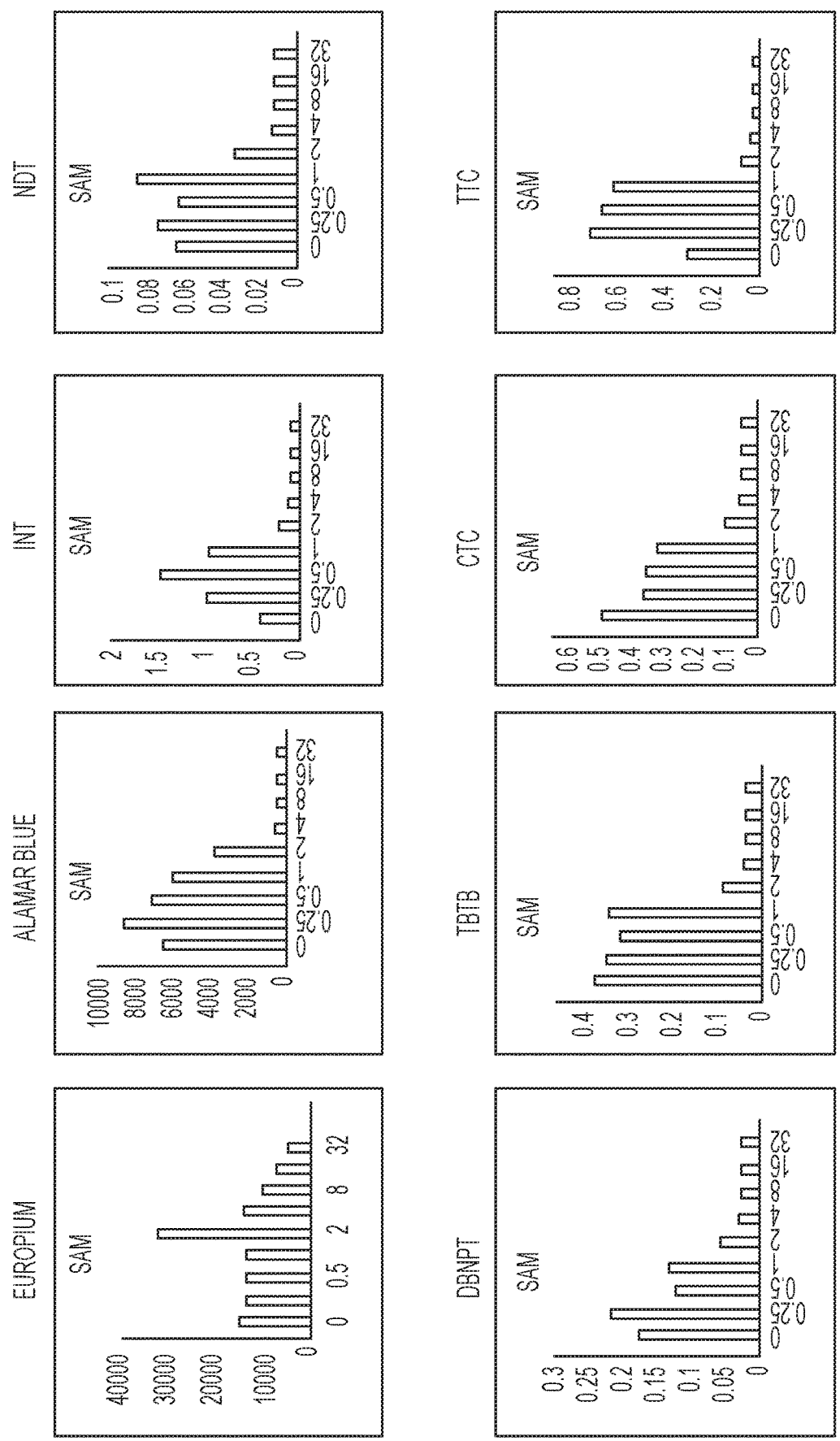
FIGS. 17-20 depict AST results when tetrazolium analogues (INT, NDT, DBNPT, TBTB, CTC, and TTC) were utilized as metabolic probes for determining the antimicrobial susceptibility of various antibiotics (e.g., Ampicillin/Sulbactam (FIG. 17), Meropenem (FIG. 18), Tobraymicin (FIG. 19), and Amikacin (FIG. 20) on *Acinetobacter baumannii*.
Figure 18:
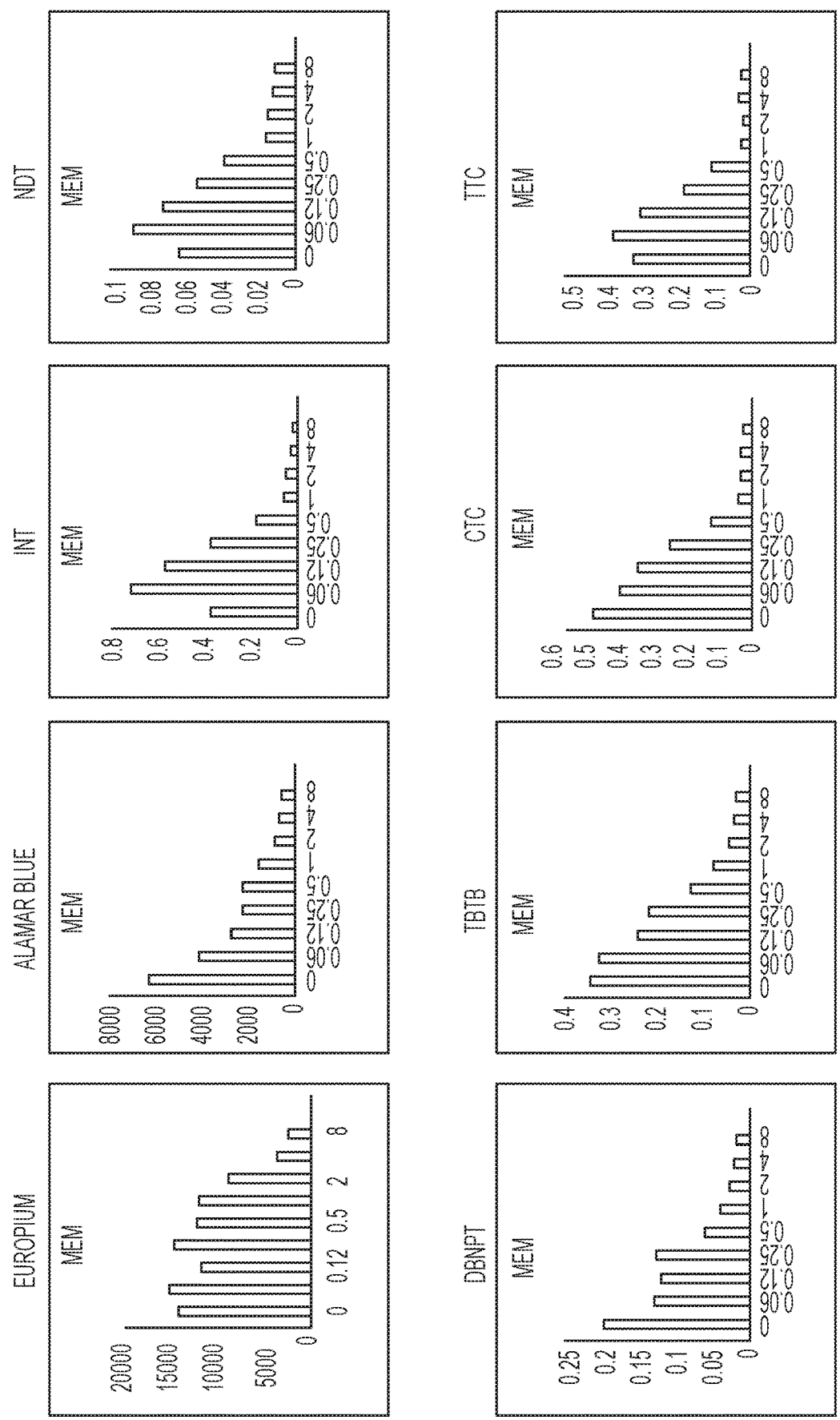
Figure 19:
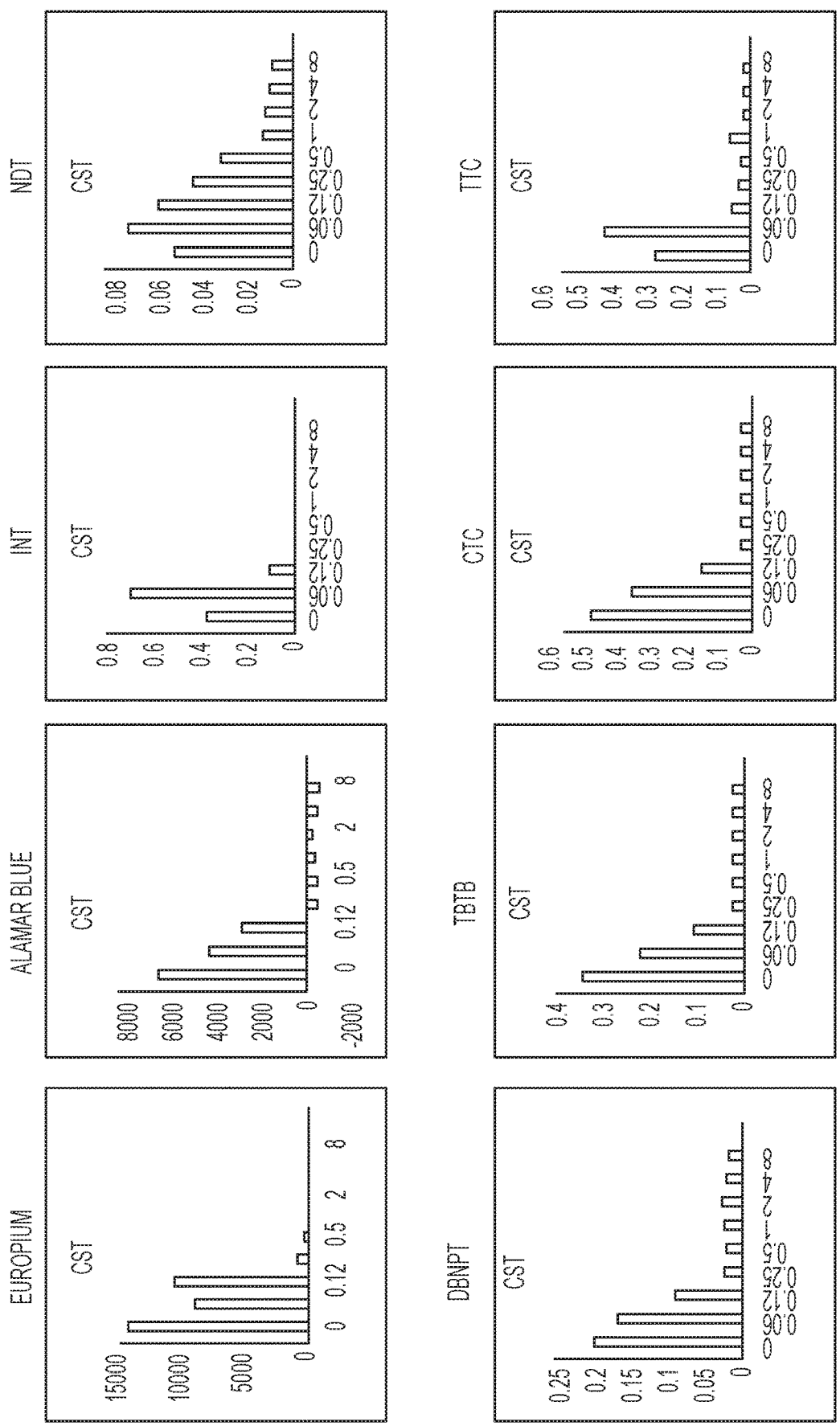
Figure 20:
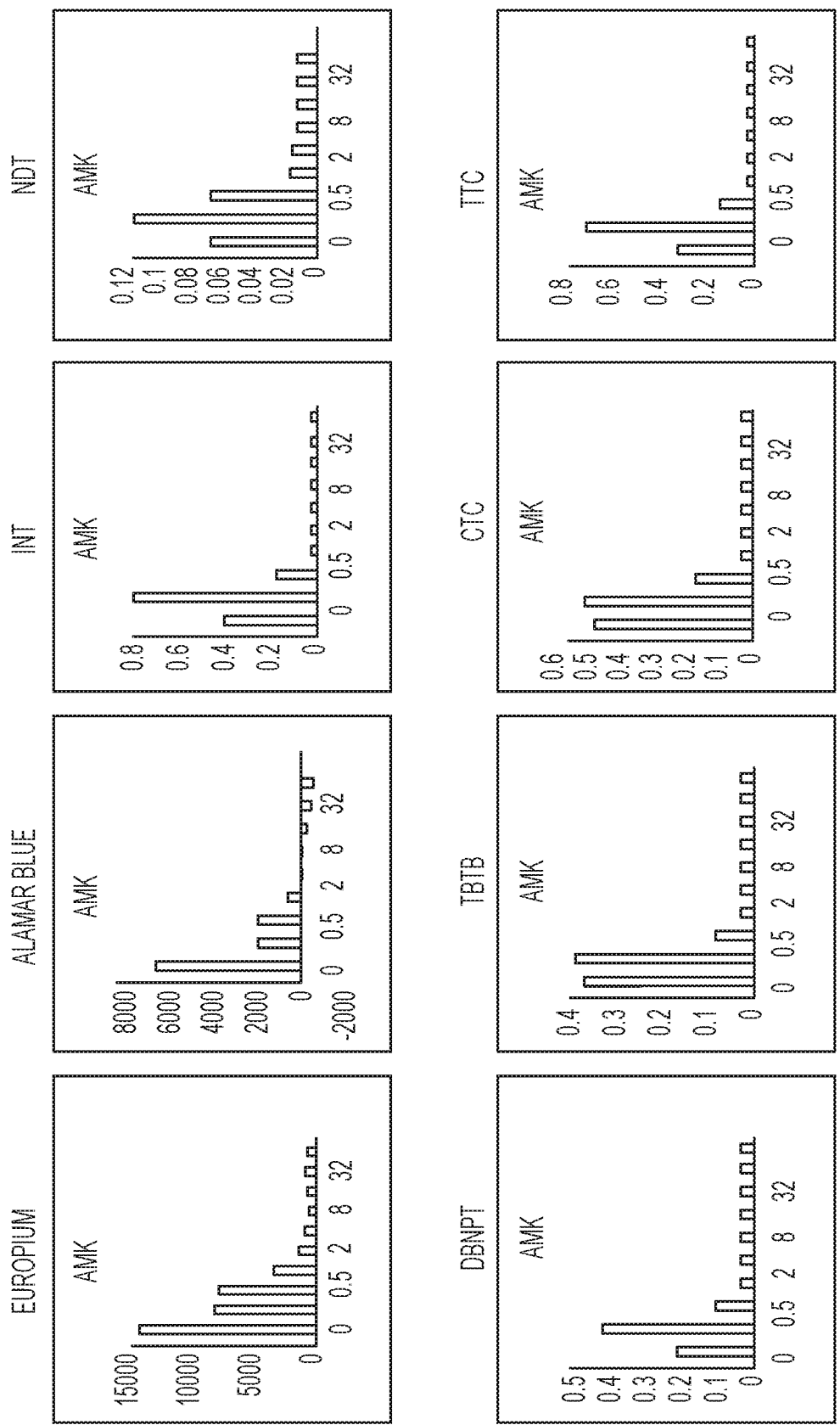
Figure 21:
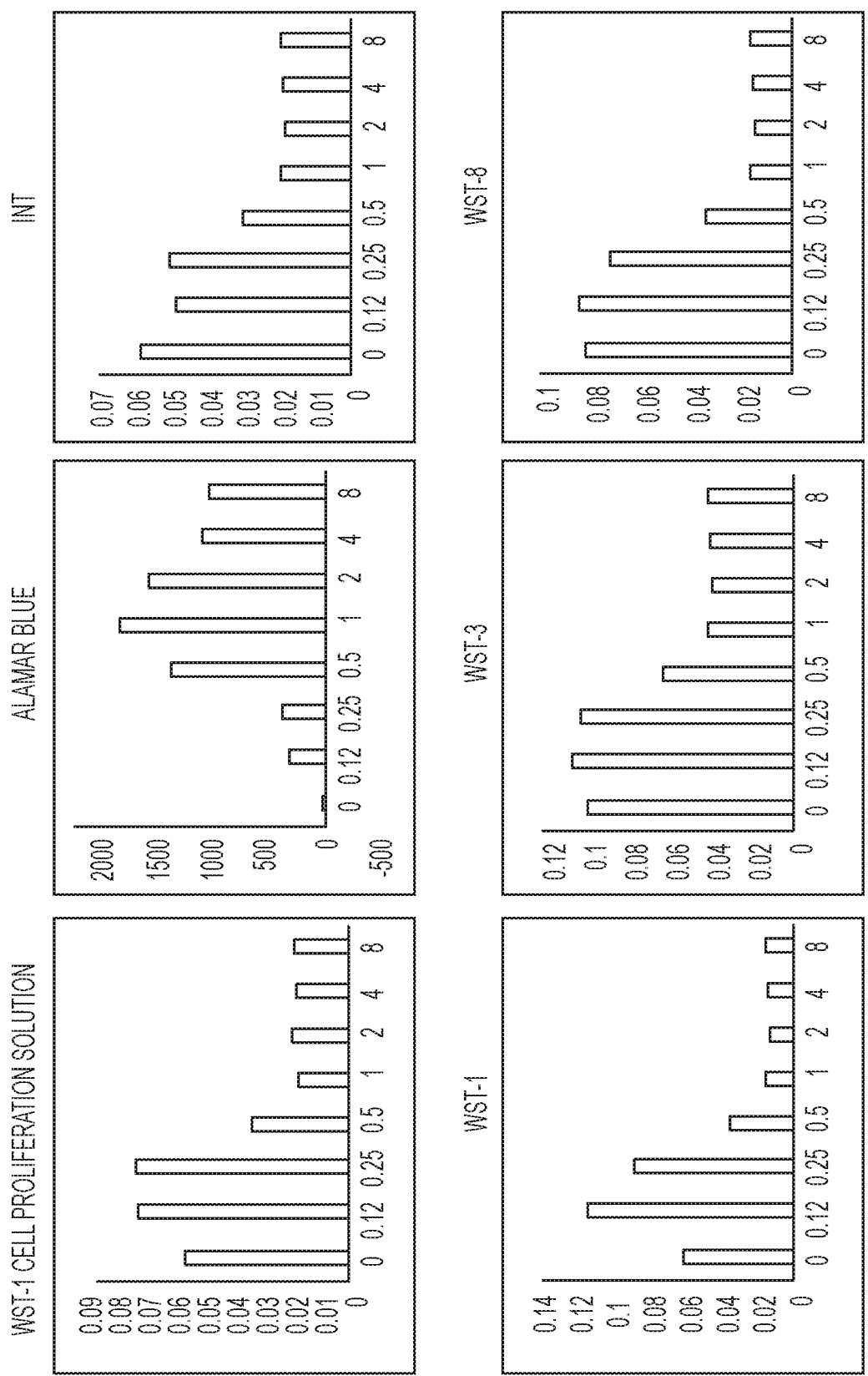
FIGS. 21-24 depict AST results when tetrazolium analogues (INT, WST-1, WST-3, and WST-8) were utilized as metabolic probes for determining the antimicrobial susceptibility of various antibiotics on *Pseudomonas aeruginosa* (e.g., Imipinem (FIG. 21), Nitrofurantoin (FIG. 22), Gentamicin (FIG. 23), and Tetracycline (FIG. 24).
Figure 22:
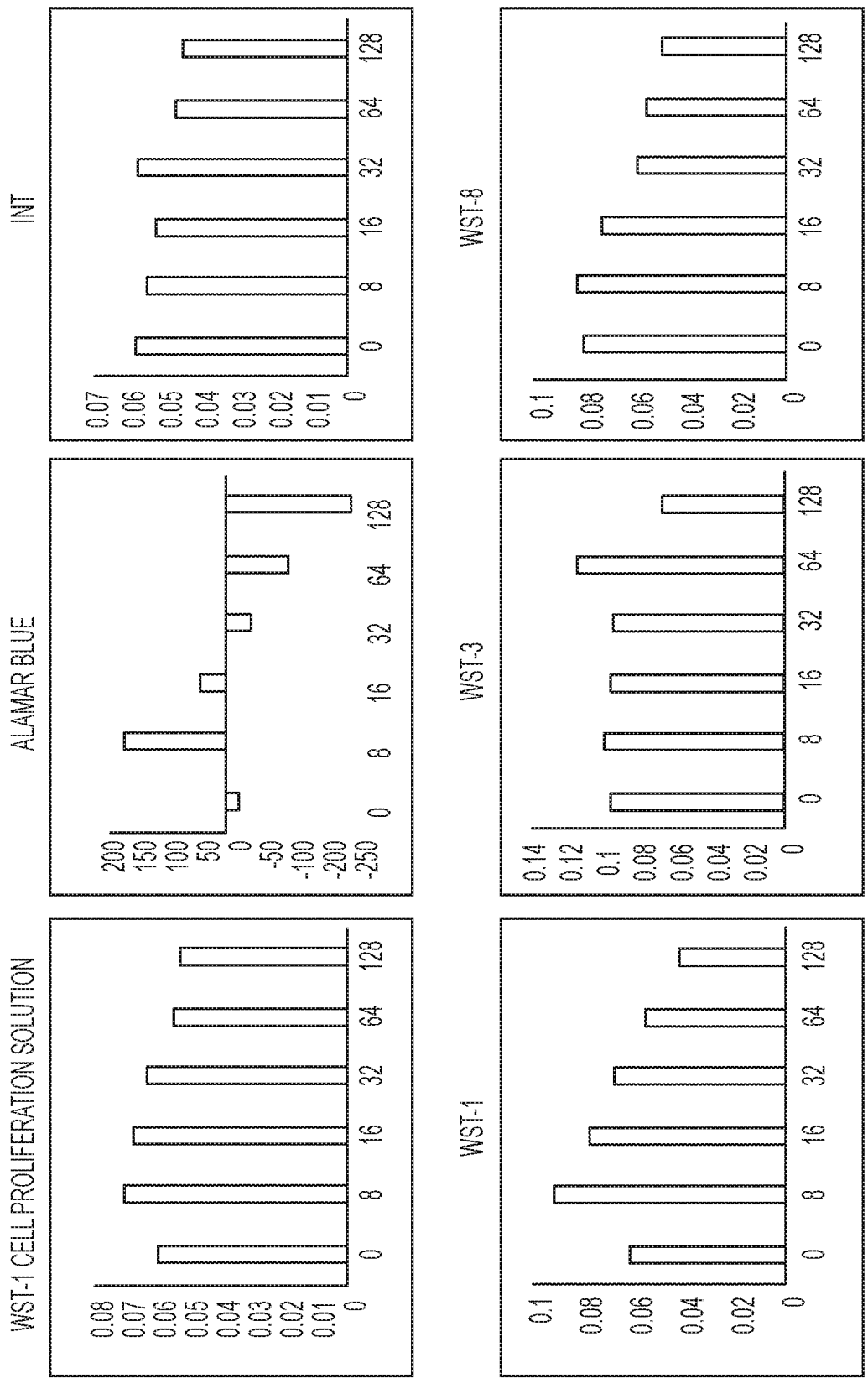
Figure 23:
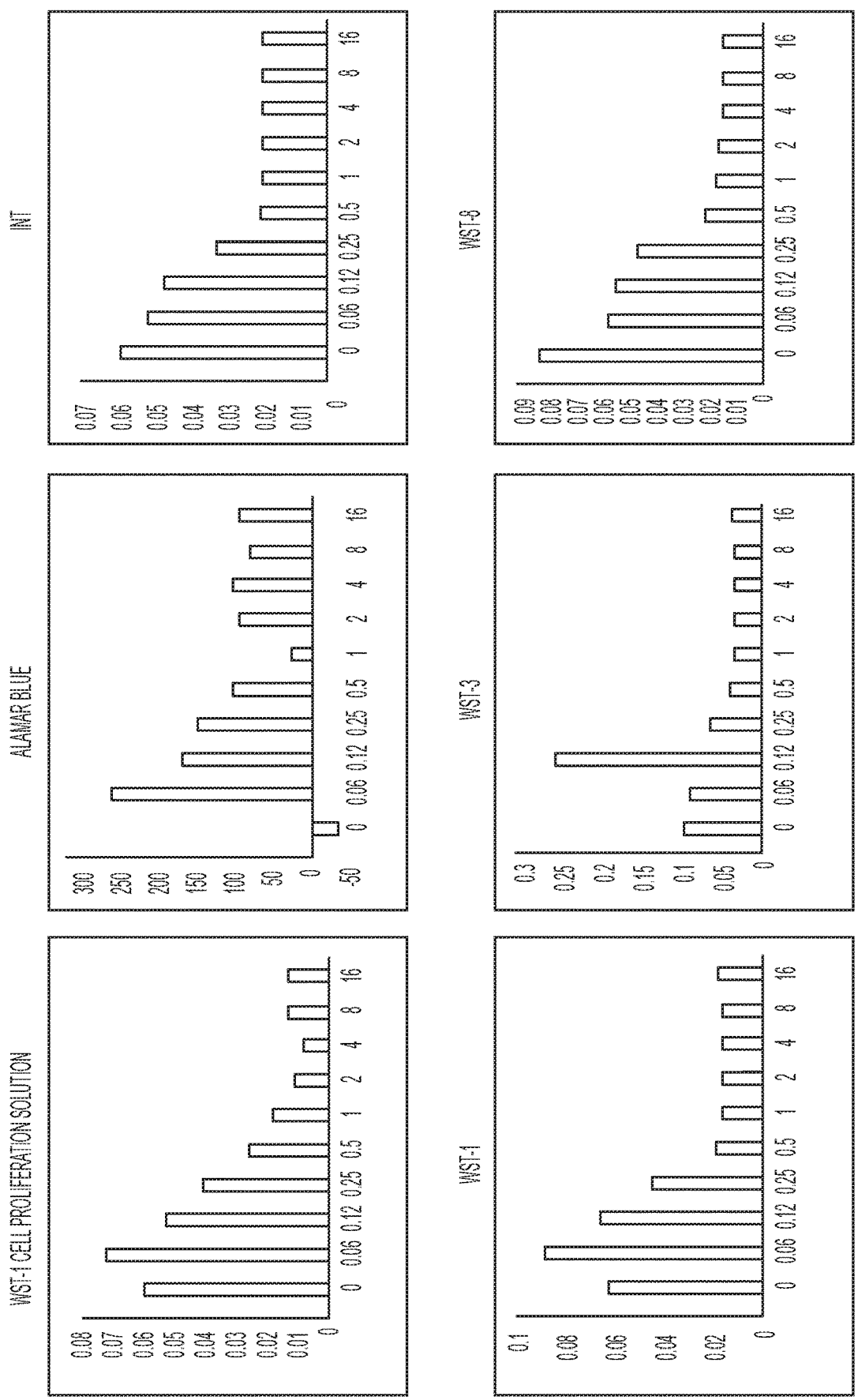

FIG. 16 shows AST results when the metabolic probe INT was tested with *Pseudomonas aeruginosa* on a single combo plate. FIGS. 17-20 depict AST results when additional tetrazolium analogues (INT, NDT, DBNPT, TBTB, CTC, and TTC) were utilized as metabolic probes when combined with *Acinetobacter baumannii* and various antibiotics (e.g., Ampicillin/Sulbactam (FIG. 17), Meropenem (FIG. 18), Tobraymicin (FIG. 19), and Amikacin (FIG. 20). AST plates were inoculated with a 1:20 dilution of 0.5 MacFarland bacterial standard and incubated for 3.5 hours. To each plate was then added 10 µl of an indicator (metabolic probe) solution-2 mg/mL solution of tetrazolium analogues NDT, DBNPT, TBTB, CTC, and TTC, a 0.8 mg/mL solution of INT, or alamarBlue®. The plates were allowed to incubate another hour to yield measurable results for viable bacteria and read on a plate reader. Tetrazoliums were read for absorbance at 490 nm and alamarBlue® was read for fluorescence at Ex560/Em590. The plate containing INT was then subjected to the Europium assay to ensure no interference is seen due to the insoluble formazan product.

Figure 24:
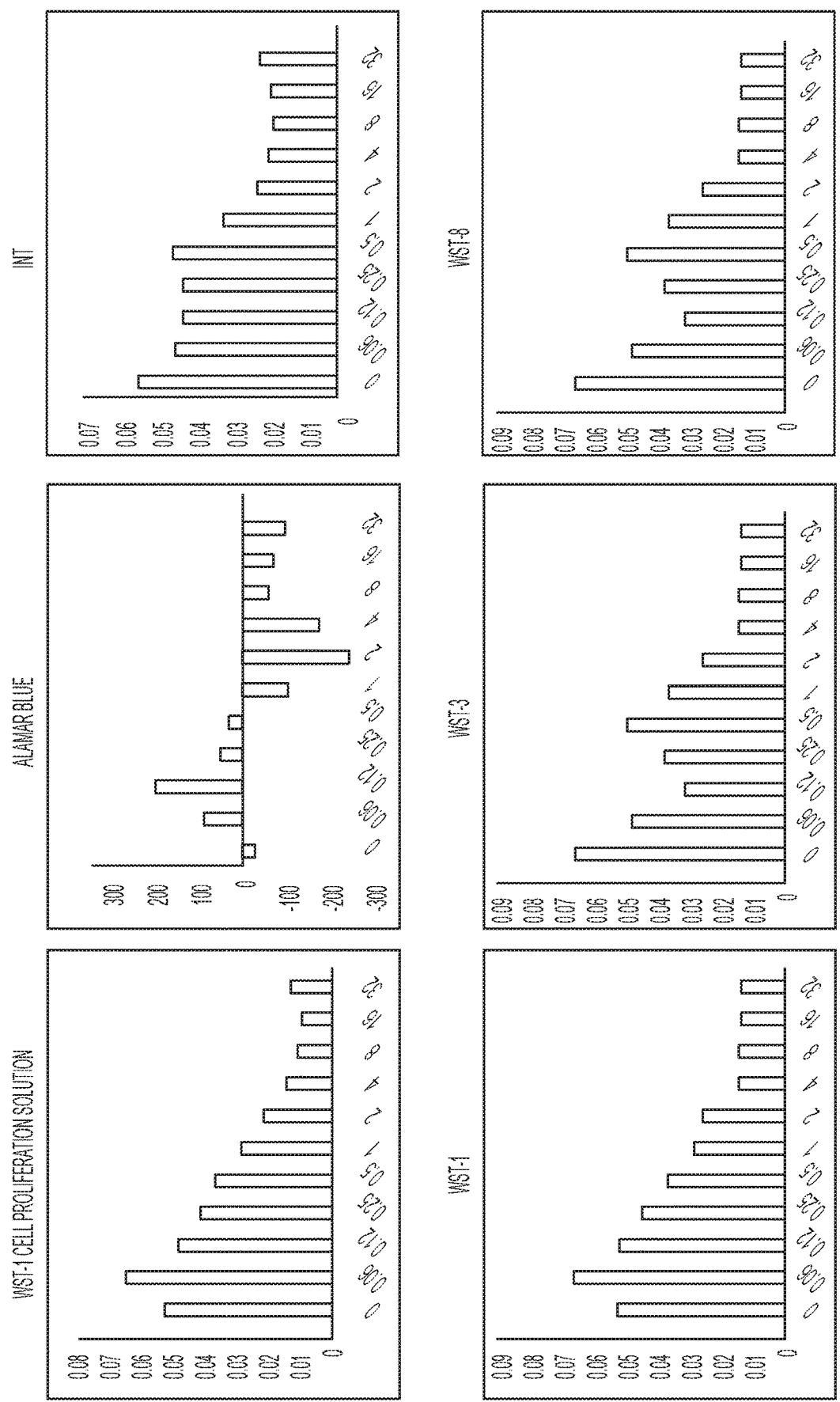
Figure 25:
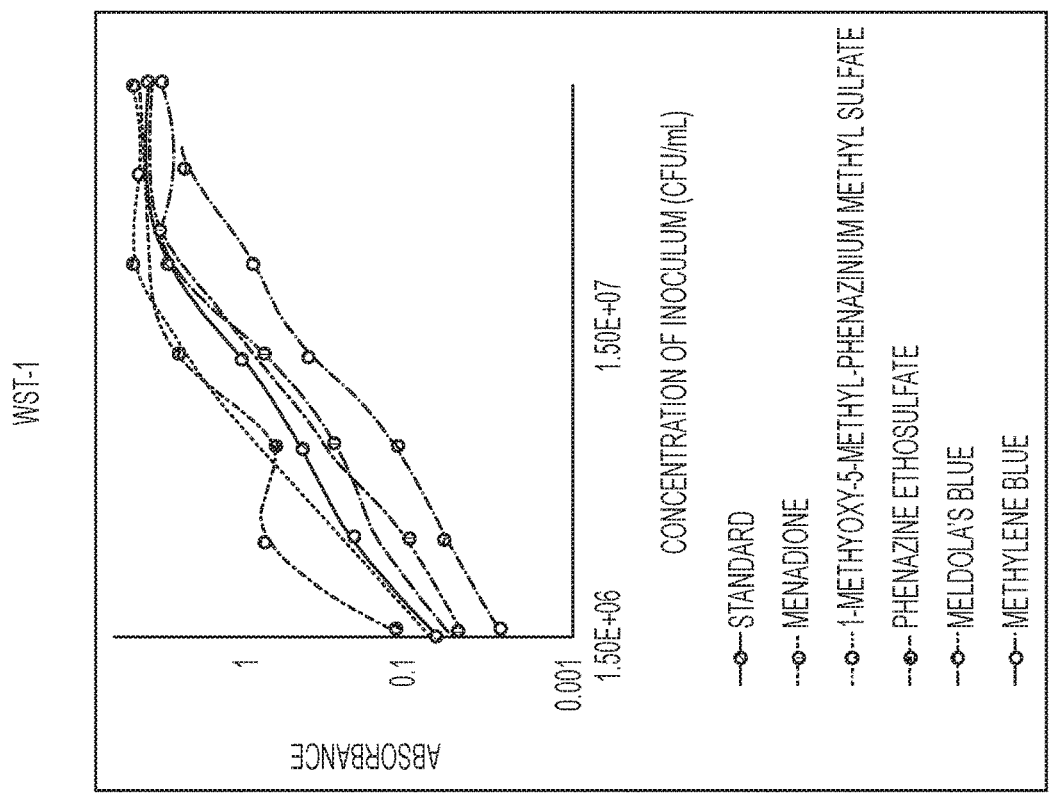
FIGS. 25-28 depict the absorbance results of the bacteria dilution curves in the presence of the various electron carriers as compared to a standard reference.
Figure 25:
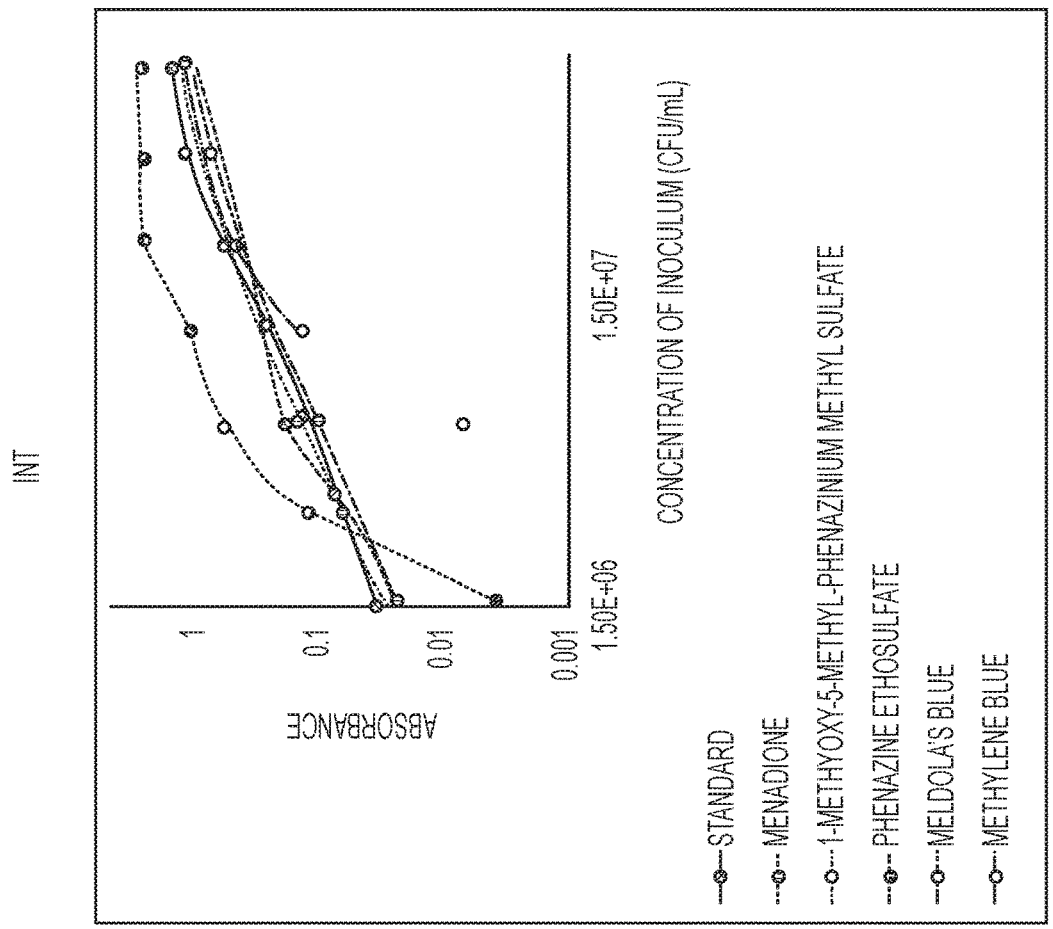
Figure 26:
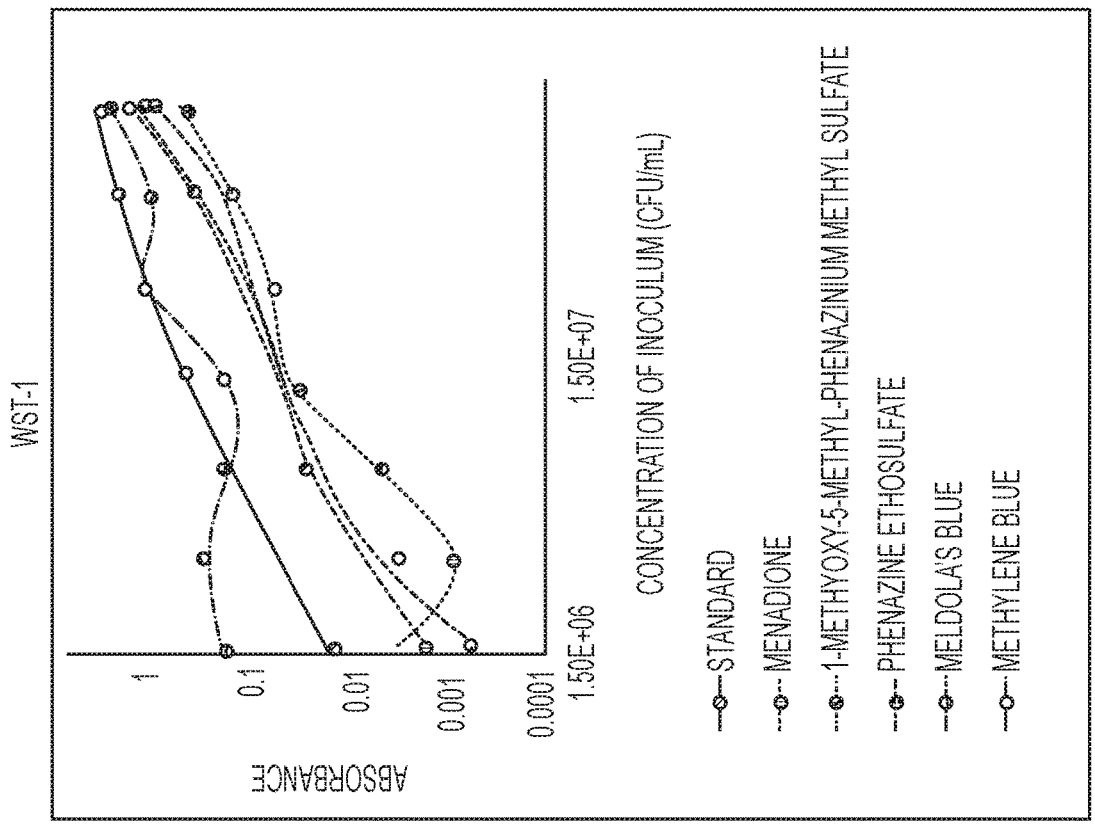
Figure 26:
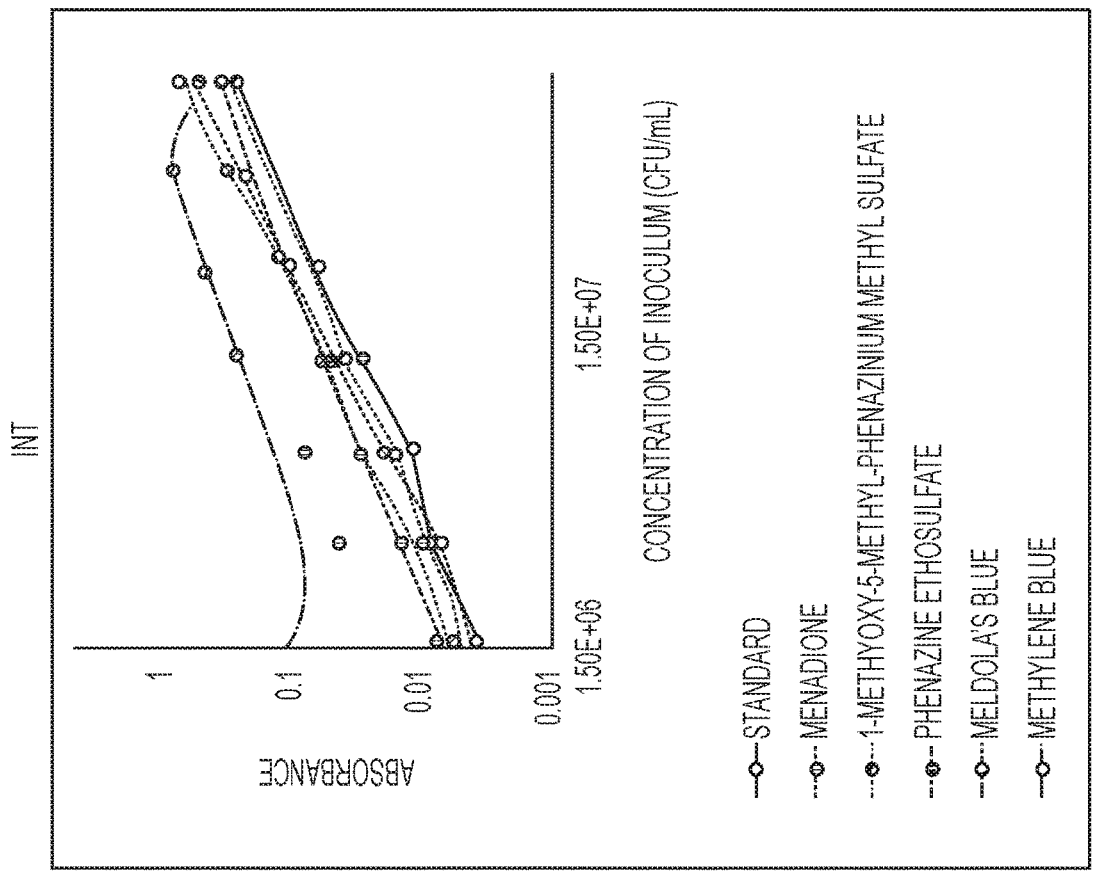
Figure 27:
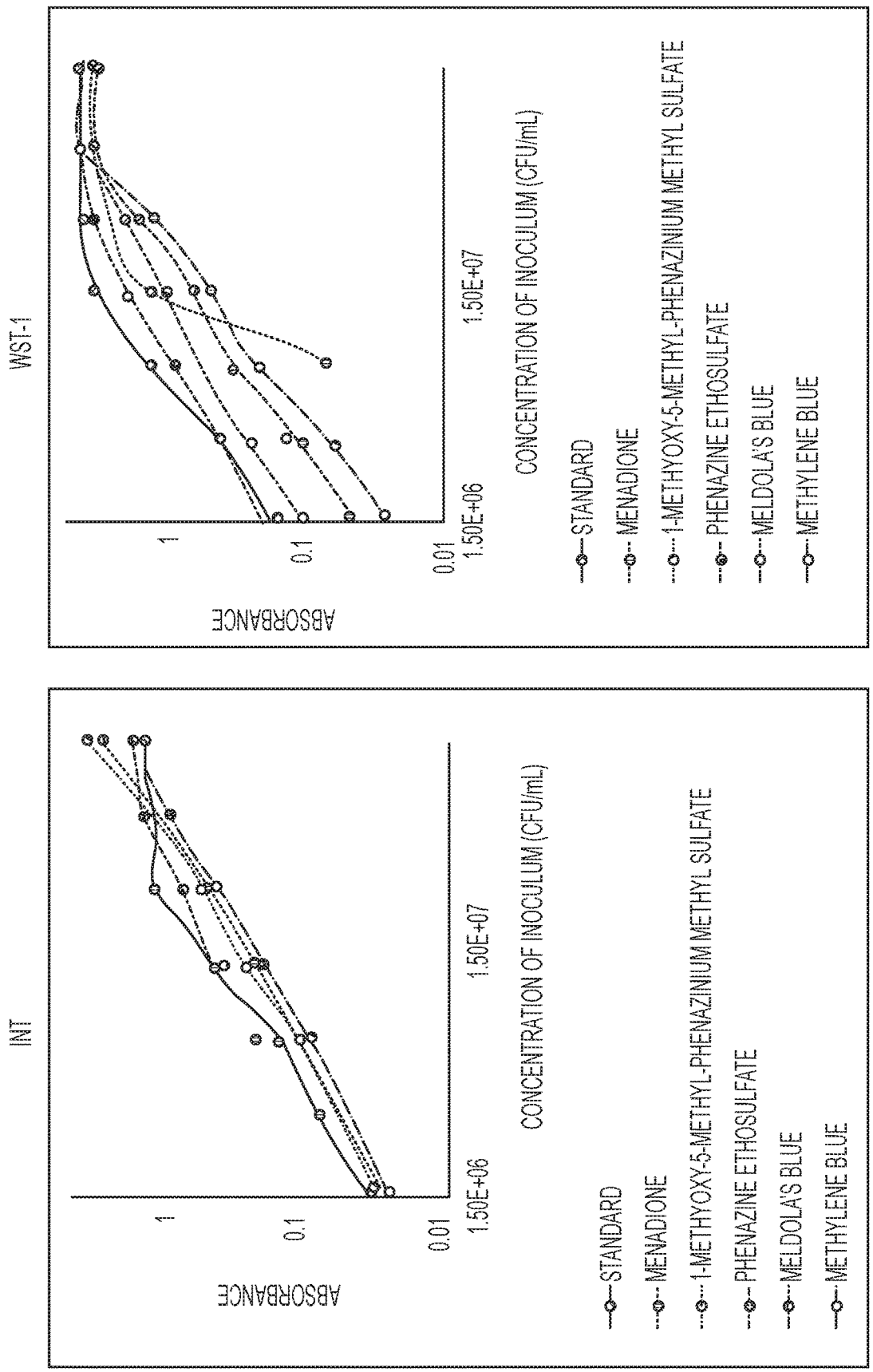
Figure 28:
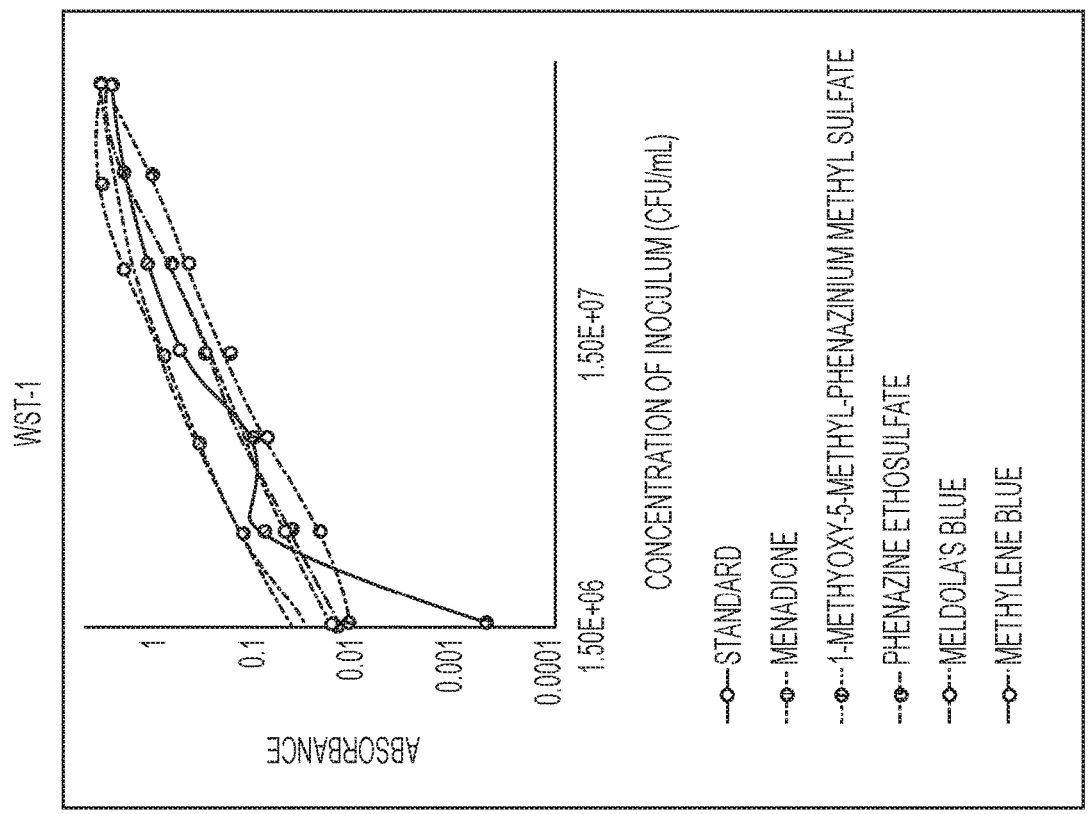
Figure 28:
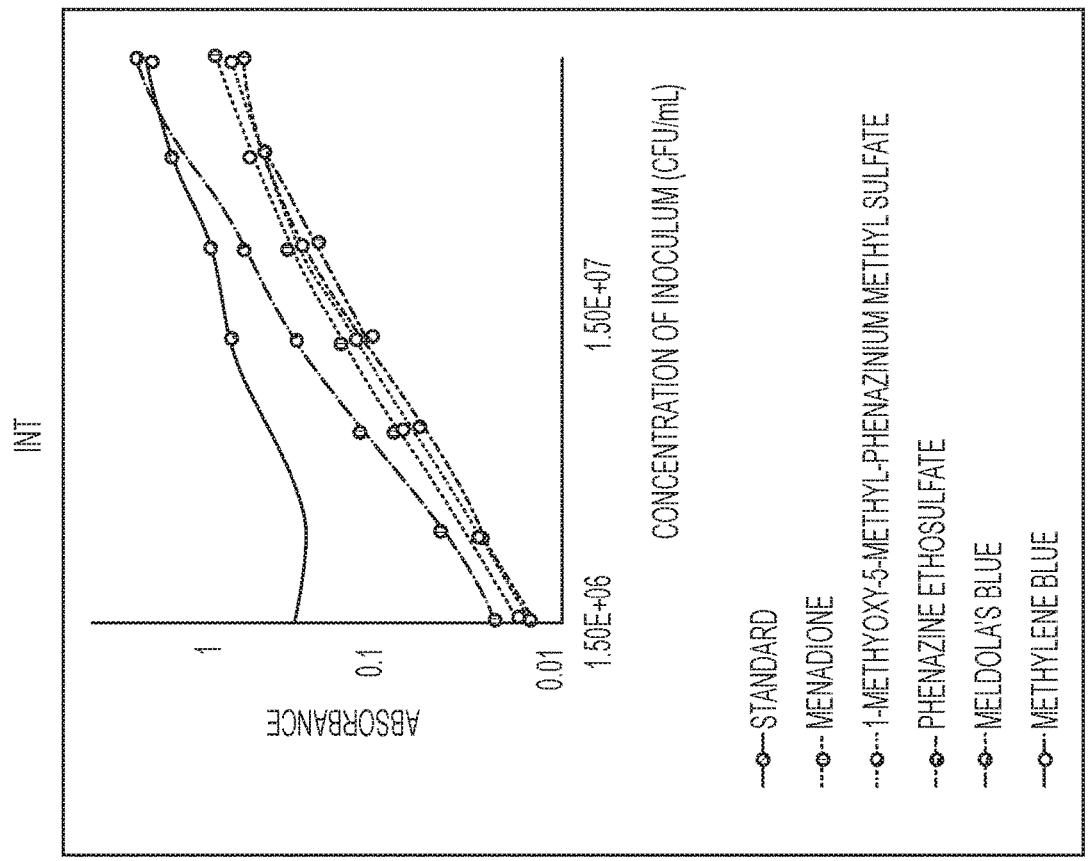
Figure 30:
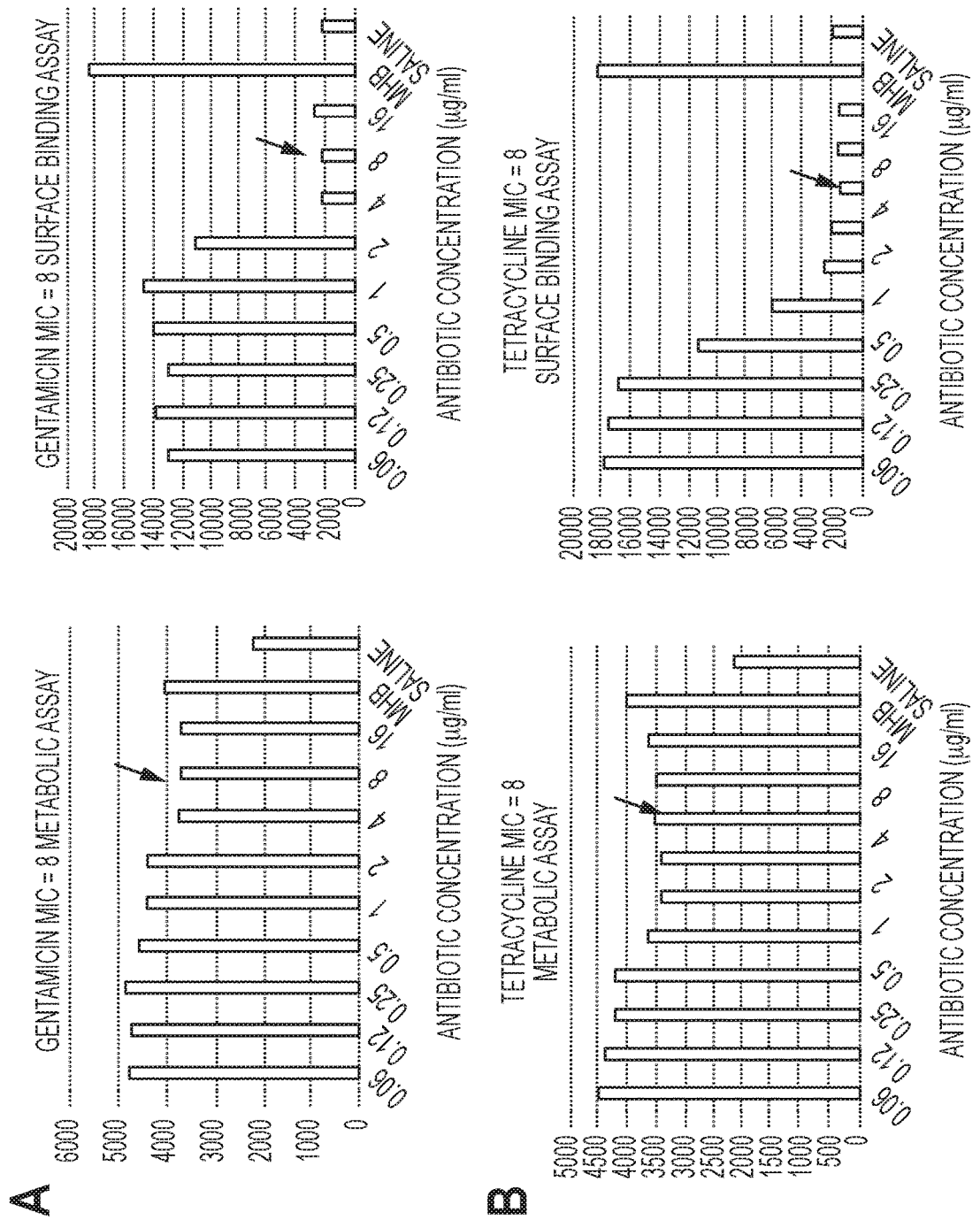
FIGS. 30 A-F depict comparison between two assays (left) metabolic assay and (right) surface binding assay, for a panel of antimicrobials on an exemplary bacterial strain, *Klebsiella pneumoniae*.
Figure 30:
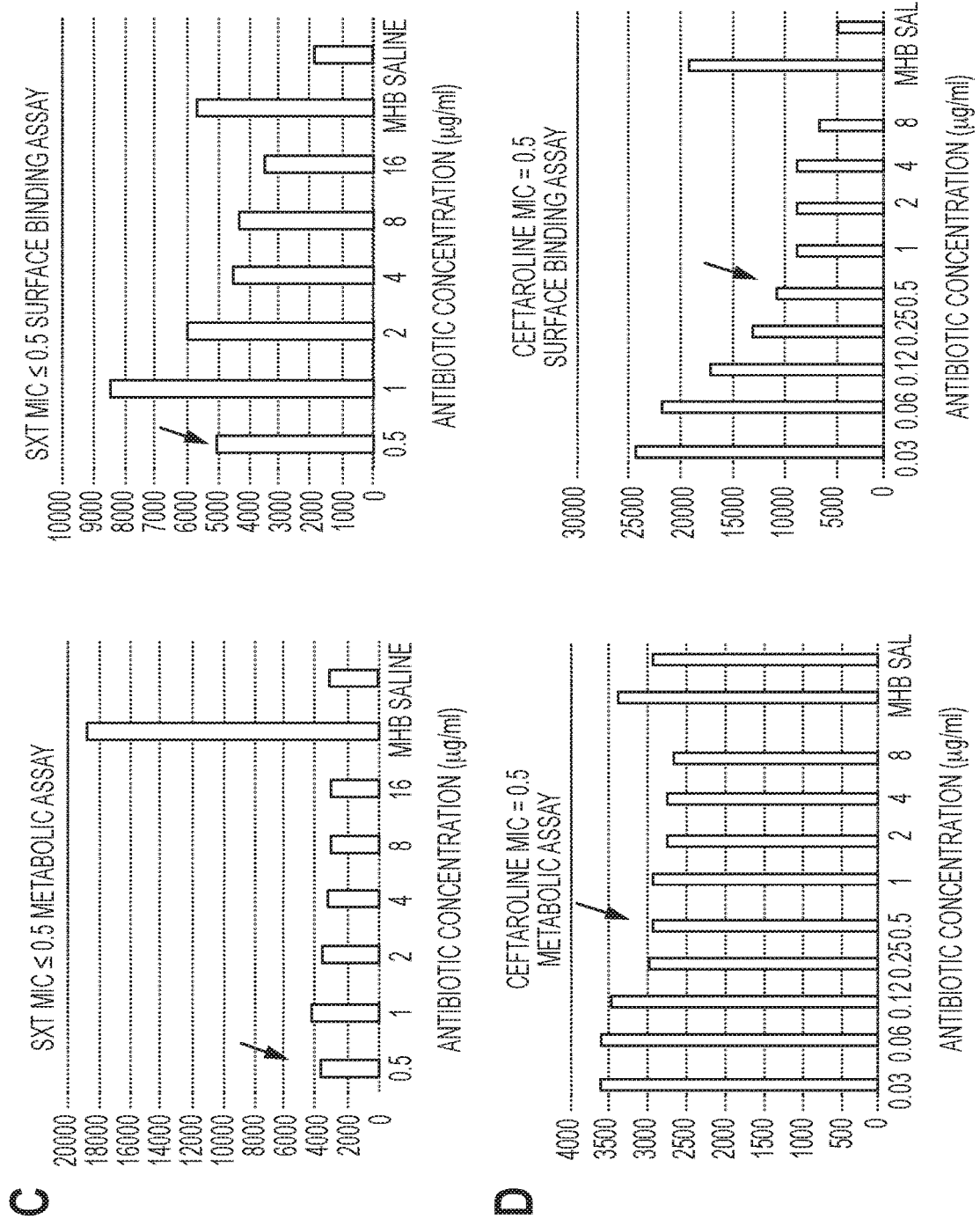
Figure 30:
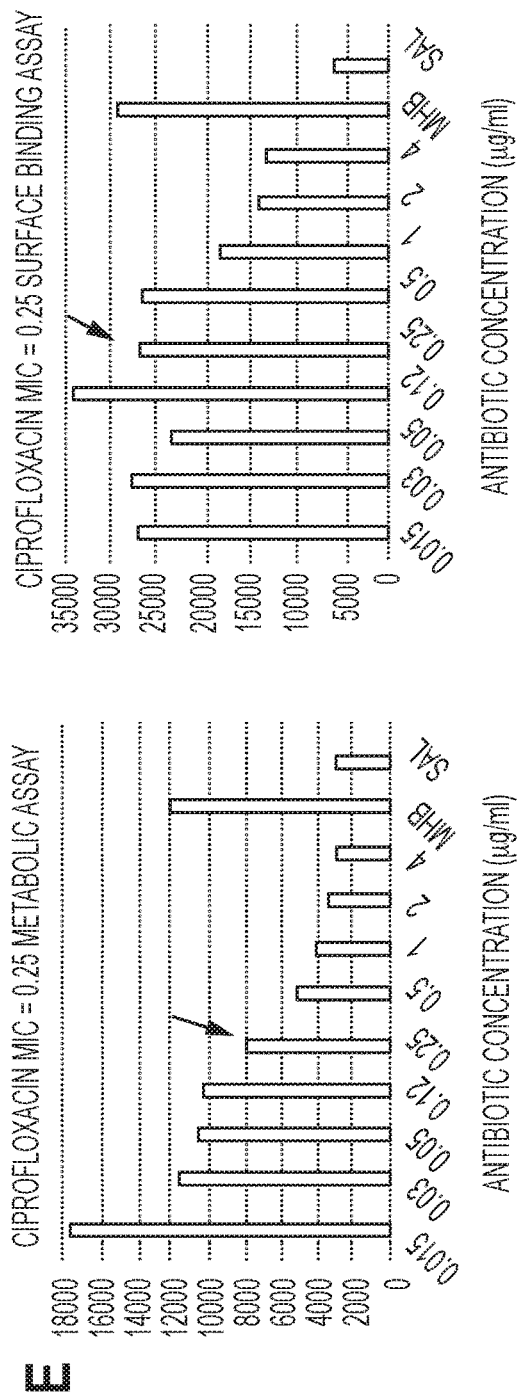
Figure 30:
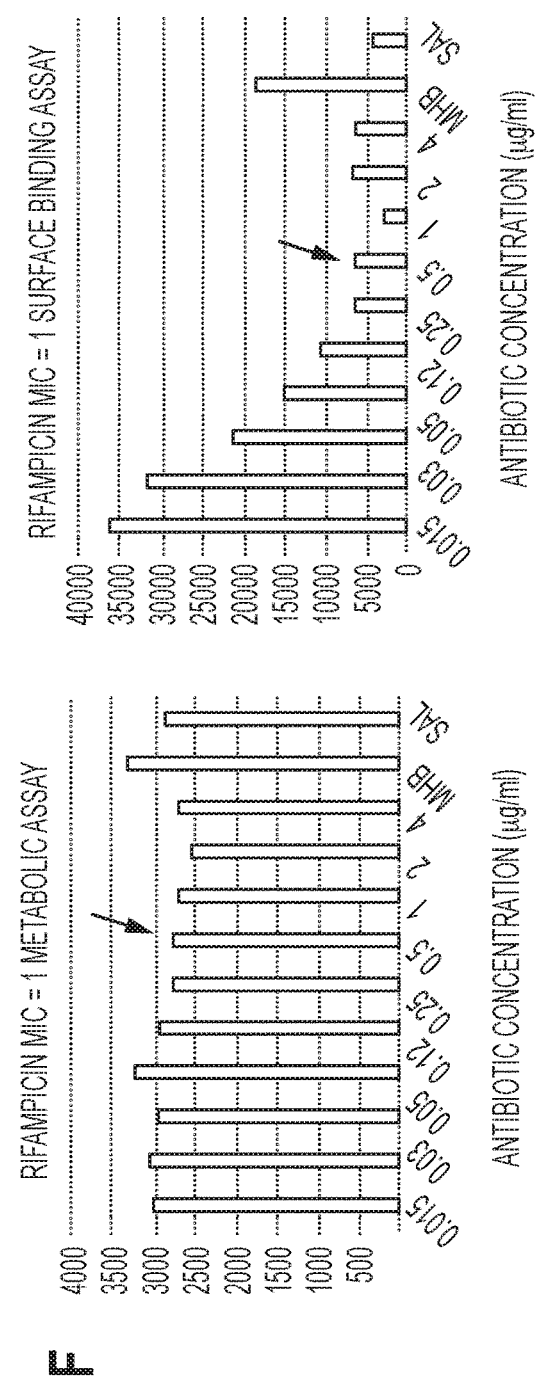

FIGS. 21-24 depict AST results when additional tetrazolium analogues (INT, WST-1, WST-3, and WST-8) were utilized as metabolic probes when combined with *Pseudomonas aeruginosa* and various antibiotics (e.g., Imipinem (FIG. 21), Nitrofurantoin (FIG. 22), Gentamicin (FIG. 23), and Tetracycline (FIG. 24). AST plates were inoculated with a 1:20 dilution of 0.5 MacFarland bacterial standard and incubated for 3.5 hours. To each plate was then added 10 µl of an indicator (metabolic probe) solution—0.5 mM solutions of WST-1, WST-3, or WST-8, the WST-1 cell proliferation solution, a 0.8 mg/mL solution of INT, or alamarBlue®. The plates were allowed to incubate another hour to yield measurable results for viable bacteria and read on a plate reader. Tetrazoliums were read for absorbance at 490 nm and alamarBlue® was read for fluorescence at Ex560/Em590. Additionally, it was found that for certain tetrazolium analogues, intermediate electron carriers were not required in order for the aforementioned AST results to be achieved. To determine if electron carrier molecules had a positive effect on INT reduction, several bacteria and electron carriers were tested. Bacteria solutions of *E. coli, P. aeruginosa, S. aureus*, and *Klebsiella* (100 µl) were inoculated into the top row of four separate 96-well microplates (one microplate per bacteria strain), containing 100 µl of MHB II in each well and serially diluted down the plate, leaving pure MHB in the final row. The plates were then incubated for 1 hour to allow the bacteria to replicate. 10 µL of a 0.8 mg/mL INT solution or the WST-1 cell proliferation solution, was placed into each well followed by the addition of 0.5 mM solutions of menadione, 1-Methyoxy-5-methylphenazinium methyl sulfate, Phenazine Ethosulfate, Meldola's Blue, or Methylene Blue. The plates were then incubated for 1 hour before measuring the absorbance of the tetrazolium at 490 nm for INT and 450 nm for WST-1. FIGS. 25-28 depict the absorbance results of the bacteria dilution curves in the presence of the various electron carriers as compared to a standard reference. FIG. 25 shows dilution curves for *Escherichia coli*; FIG. 26, for *Psuedomonas aeruginosa*; FIG. 27, *Staphylococcus aureus*; FIG. 28, *Klebsiella pneumonia*.

Example 6: Performing Dual Assays for MIC Confirmation

This example shows that AST-based MIC assays using two different assays methods for each sample can provide better confirmation than using any single assay. A percent correct score was prepared for metabolic assay or surface binding assay, based on algorithmically called data of more than 30 strains of each species. In this scoring system, an Essential Agreement was deemed to have been reached when the MIC for the two assays differed from each other by one doubling dilution. FIG. 29 shows the percent correct score for metabolic assay or surface binding assay for two species of bacteria, A, *K. pneumoniae*, and B, *S. aureus*. As seen in the figure, although there was fair amount of agreement between the two assays, the percent correct scores differed among assays based on the antibiotic used, for example, in FIG. 29A, a surface binding assay for Gentamycin (GEN) showed better agreement with the algorithmically called MIC than the metabolic assay for *K. pneumoniae,* 95% versus 83%. In such case a surface binding assay generated a more decisive, clear and convincing result for the MIC of the antimicrobial Gentamycin on the microorganism, *K. pneumoniae*. On the other hand the antimicrobial Ceftriaxone (CRO) showed high degree of accuracy with both the metabolic assay and the surface binding assay, with the metabolic assay achieving 100% agreement with the algorithmically called MIC data.

A further detailed survey of the dual assay was performed with a greater selection of antibiotics on *K. pneumoniae*, and *S. aureus* as shown in FIGS. 30A-F. In this assay, AST plates were inoculated with bacteria based on CLSI guidelines. The bacteria (FIGS. 30 A-C, *Klebsiella* sp., and FIGS. 30 D-F, *Staphylococcus aureus*), were incubated in 35° C. for 3 hours in shaking condition and allowed to grow. Following the incubation, resazurin reagent was added at 1:10 well volume and incubated for another 1 hour. The spectroscopic measurements were obtained at excitation/emission wavelengths of 560/590 nm, which gave the metabolic assay results. 100 microliters of detergent solution containing 1% Tween in PBS was added to each well, and kept in shaking condition for 10 minutes. The culture was centrifuged at 2,500×g for 2.5 minutes to obtain the bacterial pellet. The supernatant was aspirated and the pellet was resuspended in 100 microliters in PBS containing 0.05% Tween per well. 10 microliters of Eu-Cryptate at a concentration of 5 ng/well (*K. pneumoniae*) or 20 ng/well (*S. aureus*) was added along with 10 □l/well 0.0005% glutaraldehyde and shaken in for 10 minutes. The plates were centrifuged for 2.5 minutes at 2,500×g. The supernatant was aspirated and washed 2-3 times with PBS containing 0.05% Tween (200 □l/well). The pellet was resuspended in PBS containing 0.05% Tween (200 □l/well) and fluorescence measurements were taken by time resolved fluorescence for obtaining binding assay results. The data are presented as bars corresponding to relative light units (RLUs).

In FIGS. 30A-F, left panels for each antimicrobial correspond to metabolic assay results and the right panels to surface binding assays. Exemplary disagreements between the two assays for each antimicrobial are pointed out by arrows in each figure. As shown in this figure, the metabolic data and the surface binding data for each antimicrobial are likely to differ depending on the antimicrobial in question, on the microorganism in question. For example, as shown in FIG. 30A, surface binding assay showed a more decisive MIC for Gentamycin on *K. pneumoniae* compared to metabolic assay, where the inhibition of the bacteria with increasing dose was less apparent. As such this shows that it is recommended that at least two assays were performed to make the best judgement on MIC for a particular antimicrobial on a given microorganism.

What is claimed is:

1. A method for determining antimicrobial susceptibility of a microorganism comprising:
    introducing suspensions of one or more microorganisms in a medium to at least a first subset of chambers and a second subset of chambers disposed within a cartridge;
    incubating the cartridge under conditions promoting microorganism growth for an initial incubation period;
    adding one or more antimicrobial agents to the second subset of chambers;
    performing one or more checkpoint assays on the first subset of chambers and a third subset of chambers disposed within the cartridge after the initial incubation period to determine if a measured threshold value indicating microorganism growth has been reached or surpassed by a predetermined threshold value, wherein at least one checkpoint assay comprises a growth indicator, further wherein the measured threshold value is a ratio of a positive control in the first subset of chambers, the first subset of chambers comprising the suspension of microorganisms in the medium and the growth indicator without an antimicrobial to a background control in the third subset of chambers, the third subset of chambers comprising the medium and the growth indicator without the microorganisms; and
    (a) if the measured threshold value has reached or surpassed the predetermined threshold value after performing the one or more checkpoint assays:
        (i) performing one or more growth assays in the second subset of cartridge chambers to determine the microorganism's susceptibility to the one or more antimicrobials; and
        (ii) obtaining a minimum inhibitory concentration (MIC) and/or a qualitative susceptibility result (QSR) for the second subset of cartridge chambers; or
    (b) if the measured threshold value has not reached or surpassed the predetermined threshold value after performing the one or more checkpoint assays, performing one or more additional incubation periods under conditions promoting microorganism growth until
        (i) the measured threshold value has reached or surpassed the predetermined threshold value, and thereafter performing step (a); or
        (ii) a maximum of 18 hours has transpired without the predetermined threshold value being reached or surpassed by the measured threshold value and no further assays are performed, wherein at least one of the growth assays comprises performing a surface-binding probe assay by introducing a surface-binding probe comprising a coordination complex of a lanthanide with diethylenetriaminetetraacetic acid or a cryptate ligand and wherein the coordination complex of the lanthanide with diethylenetriaminetetraacetic acid or the cryptate ligand are used for time-resolved fluorescence (TRF) or time-gated luminescence (TGL).

2. The method of claim 1, comprising a plurality of growth assays comprising the one or more growth assay, wherein at least one growth assay of the plurality of growth assays is selected from the group consisting of: a metabolic probe assay, a chemical probe assay, a biochemical probe assay, an enzymatic biochemical probe assay, an ATP assay, a nucleic acid probe assay, a double-stranded nucleic acid probe assay, an optical density assay, a visual assay, and a pH molecular probe assay.

3. The method of claim 1, comprising a plurality of growth assays comprising the one or more growth assays, wherein each of the growth assays is selected from the group consisting of: a metabolic probe assay, the surface-binding probe assay, a chemical probe assay, a biochemical probe assay, an enzymatic biochemical probe assay, an ATP assay, a nucleic acid probe assay, a double-stranded nucleic acid probe assay, an optical density assay, a visual assay, and a pH molecular probe assay.

4. The method of claim 3, wherein the plurality of growth assays are the metabolic probe assay, and wherein the metabolic probe assay comprises 7-hydroxy-10-oxidophenoxazin-10-ium-3-one (resazurin).

5. The method of claim 1, wherein the surface-binding probe comprises

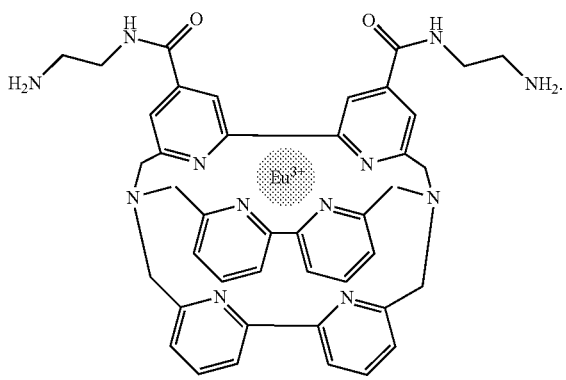

6. The method of claim 1, wherein the surface-binding probe comprises europium, strontium, terbium, samarium, and dysprosium, or a combination thereof.

7. The method of claim 1, wherein the one or more growth assays comprise a secondary growth assay or the one or more checkpoint assays for determining microorganism growth comprises (a) nucleic acid amplification, (b) nucleic acid sequencing, (c) use of adenosine triphosphate, (d) light scattering, (e) optical microscopy, or (f) measuring microorganism mass.

8. The method of claim 1, wherein the one or more growth assays and the one or more checkpoint assays are performed (a) sequentially or (b) concurrently.

9. The method of claim 1, wherein at least one checkpoint assay is performed by absorbance, nephelometry, mass resonance, or acoustically.

10. The method of claim 1, wherein the growth indicator comprises resazurin.

11. The method of claim 1, wherein the cartridge comprises 96, 384, or 1536 chambers.

12. The method of any of claim 1, wherein the one or more microorganisms derive from a clinical sample.

13. The method of claim 12, wherein the clinical sample comprises a microorganism from the group consisting of: *Escherichia* spp., *Enterococcus* spp., *Staphylococcus* spp., *Klebsiella* spp., *Acinetobacter* spp., *Pseudomonas* spp., *Enterobacter* spp., *Streptococcus* spp., *Proteus* spp., *Aerococcus* spp., *Actinomyces* spp., *Bacillus* spp., *Bartonella* spp., *Bordetella* spp., *Brucella* spp., *Campylobacter* spp., *Chlamydia* spp., *Chlamydophila* spp., *Clostridium* spp., *Corynebacterium* spp., *Ehrlichia* spp., *Francisella* spp., *Gardenerella* spp., *Haemophilius* spp., *Helicobacter* spp., *Lactobacillus* spp., *Legionella* spp., *Leptospira* spp., *Listeria* spp., *Mycobacterium* spp., *Mycoplasma* spp., *Neisseria* spp., *Nocardia* spp., *Pasteurella* spp., *Rickettsia* spp., *Salmonella* spp., *Shigella* spp., *Stenotrophomonas* spp., *Treponema* spp., *Ureaplasma* spp., *Vibrio* spp., *Yersinia* spp., *Candida* spp., *Issatchenkia* spp., *Blastomyces* spp., *Coccidioides* spp., *Aspergillus* spp., *Cryptococcus* spp., *Histoplasma* spp., *Pneumocystis* spp., *Stachybotrys* spp., *Sporothrix, Exserohilum, Cladosporium*, ringworm, mucormycetes, and a combination thereof.

14. The method of claim 1, wherein the method is performed in an automated platform for antimicrobial susceptibility testing.

* * * * *